US007598048B2

(12) United States Patent
Zhou et al.

(10) Patent No.: US 7,598,048 B2
(45) Date of Patent: *Oct. 6, 2009

(54) SCREENING METHODS FOR IDENTIFYING AGENTS THAT MODULATE OUTPUT OF A CIRCADIAN PACEMAKER

(75) Inventors: Qun-Yong Zhou, Irvine, CA (US); Clayton M. Bullock, Irvine, CA (US)

(73) Assignee: The Regents of the University of California, Oakland, CA (US)

(*) Notice: Subject to any disclaimer, the term of this patent is extended or adjusted under 35 U.S.C. 154(b) by 156 days.

This patent is subject to a terminal disclaimer.

(21) Appl. No.: 10/417,426

(22) Filed: Apr. 15, 2003

(65) Prior Publication Data

US 2003/0235535 A1 Dec. 25, 2003

Related U.S. Application Data

(60) Provisional application No. 60/372,836, filed on Apr. 15, 2002.

(51) Int. Cl.
*G01N 33/566* (2006.01)
(52) U.S. Cl. ...................... 435/7.21; 436/501
(58) Field of Classification Search .................. None
See application file for complete search history.

(56) References Cited

U.S. PATENT DOCUMENTS

| 5,545,549 | A * | 8/1996 | Gerald et al. ............. 435/365 |
| 5,621,079 | A * | 4/1997 | Cascieri et al. ........... 530/350 |
| 2003/0235535 | A1* | 12/2003 | Zhou et al. ............... 424/9.2 |
| 2004/0241757 | A1* | 12/2004 | Matsumoto et al. | |
| 2006/0172935 | A1* | 8/2006 | Zhou et al. ............... 514/12 |

FOREIGN PATENT DOCUMENTS

| WO | WO 95/35320 A1 | 12/1995 |
| WO | 9846620 | * 10/1998 |
| WO | WO 98/46620 | * 10/1998 |
| WO | WO 02/00711 A2 | 1/2002 |

OTHER PUBLICATIONS

Dunlap 1999. Cell 96:271-290.*
Mintz 1999. Journal of Neuroscience 19:5124-5130.*
Schwartz 1987. Proc Natl Acad Sci USA 84:1694-1698.*
Akiyama 1999. Journal of Neuroscience 19:1115-1121.*
Harrington 1997. Neuroreport 8:2677-2680.*
Huhman 1996. Neuroreport 7:1249-1252.*
Sweetnam 1995. Chapter 17 in Burger's Medicinal Chemictry and Drug Discovery, Fifth Edition, vol. 1, pp. 697-731.*
Lowrey 2000. Science 288:483-491.*
Turek et al. 1995. Frontiers in Neuroendocrinology 16:191-223.*
Edelstein 2001. Brain Research 918:107-112.*
Mrosovsky 1999. Chronobiology International 16:415-429.*
Silver et al. 1996 Nature 382:810-813.*
Reppert 2000. Seminars in Perinatology 24:243-246.*
Jud et al. 2005. Biol. Proced. Online 7:101-116.*
Li et al. 2006. Journal of Neuroscience 26:11615-11623.*
Levine et al. 2002. Signal analysis of behavioral and molecular cycles. BMC Neuroscience 3:1-25.*

Albers et al. 1984 Science 223:833-835.*
Stoynev et al. 1996. Acta Physiol Pharmacol Bulg 22:39-43.*
Harrington, Mary E. and Hoque, Sabina, "NPY Opposes PACAP phase shifts via receptors different from those involved in NPY Phase Shifts", *Neuroreport*, vol. 8, pp. 2677-2680, 1997.
Huhman, Kim L. et al., "Neuropeptide Y phase shifts circadian rhythms in vivo via a $Y_2$ receptor", *Neuroreport*, vol. 7, pp. 1249-1252, 1996.
Lowrey, Phillip L. et al., "Positional Syntenic Cloning and Functional Characterization of the Mammalian Circadian Mutation *tau* ", *Science*, vol. 288, pp. 483-491, 2000.
Sweetnam, Paul M. et al., "Mass Ligand Screening as a Tool for Drug Discovery and Development", *Burger's Medicinal Chemistry and Drug Discovery*, Fifth Edition, vol. 1, Chapter 17, pp. 697-731, 1995.
Boer, G. J. et al., "Vasopressin-Deficient Suprachiasmatic Nucleus Grafts Re-Instate Circadian Rhythmicity in Suprachiasmatic Nucleus-Lesioned Arrhythmic Rats", *Neuroscience*, vol. 89, pp. 375-385, 1999.
Cheng, M. Y. et al., "Prokineticin 2 transmits the behavioural circadian rhythm of the suprachiasmatic nucleus", *Nature*, vol. 417, pp. 405-410, 2002.
Jin, X. et al., "A Molecular Mechanism Regulating Rhythmic Output from the Suprachiasmatic Circadian Clock", *Cell*, vol. 96, pp. 57-68, 1999.
Kalsbeeck, A. et al., "A Diurnal Rhythm of Stimulatory Input to the Hypothamamo-Pituitary-Adrenal System as Revealed by Timed Intrahypothalamic Administration of the Vasopressin V1 Antagonist", *The Journal of Neuroscience*, vol. 17, pp. 5555-5565, 1996.
Kalsbeek, A. et al., "Vasopressin-containing neurons of the suprachiasmatic nuclei inhibit corticosterone release", *Brain Research*, vol. 580, pp. 62-67, 1992.
Li et al., "Identification of Two Prokineticin cDNAs: Recombinant Proteins Potently Contract Gastrointestinal Smooth Muscle", *Molecular Pharmacology*, 59:692-698 (2001).
Lin et al., "Identification and Molecular Characterization of Two Closely Related G Protein-Coupled Receptors Activated by Prokineticins/Endocrine Gland Vascular Endothelial Growth Factor", *The Journal of Biological Chemistry*, 277(22):19276-19280 (2002).
Melchiorri et al., "The Mammalian Homologue of the Novel Peptide Bv8 is Expressed in the Central Nervous System and Supports Neuronal Survival by Activation the Map Kinase/PI-3-Kinase Pathways", *European Journal of Neuroscience*, 13:1694-1702 (2001).
Parker et al., "Y-Receptor-Like Genes GPR72 and GPR73: Molecular Cloning, Genomic Organization and Assignment to Human Chromosome $11_q21.1$ and $2_p14$ and Mouse Chromosome 9 and 6", *Biochimica et Biophysica Acta*, 1491:369-375 (2000).

* cited by examiner

*Primary Examiner*—Daniel E. Kolker
(74) *Attorney, Agent, or Firm*—DLA Piper LLP (US)

(57) ABSTRACT

The invention provides a method for screening for a compound for modulating circadian rhythm. The method involves (a) providing a compound that is a Prokineticin 2 (PK2) receptor antagonist or agonist; and (b) determining the ability of the compound to modulate one or more indicia of circadian rhythm function, wherein a compound that modulates one or more indicia of circadian rhythm function is identified as a compound for modulating circadian rhythm. The invention also provides a mouse PK2 receptor nucleic acid, polypeptide and related compositions. Further provided is a method for modulating circadian rhythm of an animal, which involves administering an effective amount of a PK2 receptor antagonist or agonist to an animal. Also provided is an isolated nucleic acid comprising a PK2 gene promoter operatively linked to a heterologous nucleotide sequence.

14 Claims, 17 Drawing Sheets

| | |
|---|---|
| HUMAN PK2 | AVITGACDKDSQCGGGMCCAVSIWVKSIRICTPMGKLGDSCHPLTRKVPFFGRRMHHTCPCLPG |
| HUMAN PK2v2 | AVITGACDKDSQCGGGMCCAVSIWVKSIRICTPMLGDSCHPLTRKNNFGNGRQERRKRKRSKRK |
| MOUSE PK2 | AVITGACDKDSQCGGGMCCAVSIWVKSIRICTPMGVGDSCHPLTRKVPFWGRRMHHTCPCLPG |
| MOUSE PK2v2 | AVITGACDKDSQCGGGMCCAVSIWVKSIRICTPMGQVGDSCHPLTRKSHVANGRQERRRAKRRK |
| HUMAN PK1 | AVITGACERDVQCGAGTCCAISLWLRGLRMCTPLGREGEECHPGSHKVPFFRKRKHHTCPCLPN |
| MOUSE PK1 | AVITGACERDIQCGAGTCCAISLWLRGLRLCTPLGREGEECHPGSHKIPFLRKRQHHTCPCSPS |
| FROG Bv8 | AVITGACDKDVQCGSGTCCAASAWSRNIRFCIPLGNSGEDCHPASHKVPYDGKRLSSLCPCKSG |
| TOAD Bv8 | AVITGACDKDVQCGSGTCCAASAWSRNIRFCIPLSGEDCHPASHKVPYDGKRLSSLCPCKSGLT |
| SNAKE MIT1 | AVITGACERDLQCGKGTCCAVSLMIKSVRVCTPVGTSGEDCHPASHKIPFSGQRMHHTCPCAPN |
| | |
| HUMAN PK2 | LACLRTSFNRFICLAQK |
| HUMAN PK2v2 | KEVPFFGRRMHHTCPCLPGLACLRTSFNRFICLAQK |
| MOUSE PK2 | LACLRTSFNRFICLARK |
| MOUSE PK2v2 | RKKEVPFWGRRMHHTCPCLPGLACLRTSFNRFICLARK |
| HUMAN PK1 | LLCSRFPDGRYRCSMDLKNINF |
| MOUSE PK1 | LLCSRFPDGRYRCFRDLKNANF |
| FROG Bv8 | LTCSKSGEKFKCS |
| TOAD BV8 | CSKSGEKFKCS |
| Snake MIT1 | LACVQTSPKKFKCLSK |

Figure 10

SEQUENCE LISTING

```
<160> NUMBER OF SEQ ID NOS: 21

<210> SEQ ID NO 1
<211> LENGTH: 2325
<212> TYPE: DNA
<213> ORGANISM: Mus musculus
<220> FEATURE:
<221> NAME/KEY: CDS
<222> LOCATION: (1)...(1146)

<400> SEQUENCE: 1 atg gga ccc cag aac aga aac act agc ttt gca cca gac ttg aat cca      48
Met Gly Pro Gln Asn Arg Asn Thr Ser Phe Ala Pro Asp Leu Asn Pro
 1               5                  10                  15 ccc caa gac cat gtc tcc tta aac tac agt tat ggt gat tat gac ctc      96
Pro Gln Asp His Val Ser Leu Asn Tyr Ser Tyr Gly Asp Tyr Asp Leu
                20                  25                  30 ccc ctg ggt gag gat gag gat gtg acc aag aca cag acc ttc ttt gca     144
Pro Leu Gly Glu Asp Glu Asp Val Thr Lys Thr Gln Thr Phe Phe Ala
            35                  40                  45 gcc aaa att gtc att ggc gtg gca ctg gca ggc atc atg ctg gtc tgc     192
Ala Lys Ile Val Ile Gly Val Ala Leu Ala Gly Ile Met Leu Val Cys
        50                  55                  60 ggc att ggc aac ttt gtc ttc att gct gcc ctc gcc cgc tac aag aag     240
Gly Ile Gly Asn Phe Val Phe Ile Ala Ala Leu Ala Arg Tyr Lys Lys
    65                  70                  75                  80 ctg cgc aac ctt acc aac ctc ctc att gct aac ctg gcc atc tct gac     288
```

-continued

```
                Leu Arg Asn Leu Thr Asn Leu Leu Ile Ala Asn Leu Ala Ile Ser Asp
                             85                  90                  95 ttc ctg gtg gcg atc gtc tgc tgc ccc ttt gag atg gac tat tat gta        336
Phe Leu Val Ala Ile Val Cys Cys Pro Phe Glu Met Asp Tyr Tyr Val
            100                 105                 110 gta cgg cag ctt tcc tgg gcg cat ggt cac gtg ctt tgt gcc tcc gtc        384
Val Arg Gln Leu Ser Trp Ala His Gly His Val Leu Cys Ala Ser Val
        115                 120                 125 aac tac ctt cgt acg gtc tcc ctg tac gtc tcc acc aac gct ctg ctg        432
Asn Tyr Leu Arg Thr Val Ser Leu Tyr Val Ser Thr Asn Ala Leu Leu
    130                 135                 140 gcc atc gct att gac aga tac ctc gct att gtc cac cct ttg aaa cca        480
Ala Ile Ala Ile Asp Arg Tyr Leu Ala Ile Val His Pro Leu Lys Pro
145                 150                 155                 160 cgg atg aat tat cag acc gct tcc ttc ctg atc gct ttg gtc tgg atg        528
Arg Met Asn Tyr Gln Thr Ala Ser Phe Leu Ile Ala Leu Val Trp Met
                165                 170                 175 gtc tcc atc ctc atc gct gtc cca tct gcc tac ttc acc aca gaa acc        576
Val Ser Ile Leu Ile Ala Val Pro Ser Ala Tyr Phe Thr Thr Glu Thr
            180                 185                 190 atc ctc gtt atc gtc aag aat caa gaa aaa atc ttc tgt ggt cag atc        624
Ile Leu Val Ile Val Lys Asn Gln Glu Lys Ile Phe Cys Gly Gln Ile
        195                 200                 205 tgg tcg gtg gac cag cag ctc tac tac aaa tcc tac ttc ctc ttc gtc        672
Trp Ser Val Asp Gln Gln Leu Tyr Tyr Lys Ser Tyr Phe Leu Phe Val
    210                 215                 220 ttc ggg ctt gag ttc gtg ggt ccc gtg gtc act atg acc ctg tgc tat        720
Phe Gly Leu Glu Phe Val Gly Pro Val Val Thr Met Thr Leu Cys Tyr
225                 230                 235                 240 gcc agg atc tcc caa gag ctc tgg ttc aag gct gta cct ggc ttc cag        768
Ala Arg Ile Ser Gln Glu Leu Trp Phe Lys Ala Val Pro Gly Phe Gln
                245                 250                 255 acg gag caa atc cgc aag cgg ctg cgt tgc cgc gcc aag aca gtg cta        816
Thr Glu Gln Ile Arg Lys Arg Leu Arg Cys Arg Arg Lys Thr Val Leu
            260                 265                 270 ctg ctc atg ggc atc ctc aca gcc tac gtg ctg tgc tgg gcg ccg ttc        864
Leu Leu Met Gly Ile Leu Thr Ala Tyr Val Leu Cys Trp Ala Pro Phe
        275                 280                 285 tat ggc ttt acc ata gtg cga gac ttc ttc ccc acg gta gtt gtg aag        912
Tyr Gly Phe Thr Ile Val Arg Asp Phe Phe Pro Thr Val Val Val Lys
    290                 295                 300 gag aag cac tac ctc acc gcc ttc tac gtc gtg gag tgc att gcc atg        960
Glu Lys His Tyr Leu Thr Ala Phe Tyr Val Val Glu Cys Ile Ala Met
305                 310                 315                 320 agc aac agc atg atc aat act ata tgc ttc gtg acg gtc aag aac aac       1008
Ser Asn Ser Met Ile Asn Thr Ile Cys Phe Val Thr Val Lys Asn Asn
                325                 330                 335 acc atg aaa tac ttc aag aag atg ctg cgg ctc cac tgg cgg ccc tct       1056
Thr Met Lys Tyr Phe Lys Lys Met Leu Arg Leu His Trp Arg Pro Ser
            340                 345                 350 cac tac ggg agt aag tcc agc gct gac ctc gac ctc aaa acc agc ggg       1104
His Tyr Gly Ser Lys Ser Ser Ala Asp Leu Asp Leu Lys Thr Ser Gly
        355                 360                 365 gtg cct gcc act gaa gag gtg gat tgt atc aga cta aag tag               1146
Val Pro Ala Thr Glu Glu Val Asp Cys Ile Arg Leu Lys *
370                 375                 380 ccttcaggtg ttgcccaagg aaaaatttaa cattcggtac tcagtaaatc acacaccatc    1206
aaccactcac aagctacatg gaaagatacg gctgtattca cgttctcctg ctctaatgta    1266
```

```
tcaggacgct tctatgtaat aacatacagc acaactgatg tctgcataac atcttagaag   1326
gcagacacaa atagtaacaa gtgatgtgga ctgaatgctt ctgtctgcaa accacaccaa   1386
ccaattattc aaggacaaga gctgacatgt gagaattacc tgctatgtgc aaaaacaagt   1446 tacccccccca aaaatgata gaagctattt ggagttattc agctctatct atctatctat   1506
ctatccatcc atccatccat ccatccaggt cactagaaag aagtcacaaa tgactagcca   1566
gagtcatgct acatattctt tcattctgta tcttttctgc acagaactgt caaaggcaat   1626
agaataaagc acctagacat actagaaatg taaggataac tccatcaata gggagaccaa   1686
ggcctcatag gaagagggtc catatagtat actgactttc cccactccac accagttatc   1746
tccttagata ttctgtactt atctgcaatg ttgtaatttc aaatgaggaa aaataagggg   1806
acaggcttta ccacagatgt atcaaatctc atcaagccca tagggcaaag atgggaggct   1866
cctgacacaa gaaatgtatc cagttctgga taactttaat gccaagcatt tcagggctct   1926
ggggtcttgg aggaagagga cacagaaaga gccgaggttt ccagtggcaa tgagtataat   1986
ctgtccattt gctatgattt ggacaatttt ctagaacata ctccgactta caaaaggaac   2046
tctacttgag atccaaagat ccgggtaaaa gtcctaaccc caggactcat ctctgtgtgt   2106
ctccactgta atgaaatgga aataatgaaa acggatcatt aggaacatca gcccggcgaa   2166
gtcatggtgt ggatgtgatt ttcacctctt cctttgtgaa gaatgaggtc gtgaaaagct   2226
cattagaggg agtttggaat ggagaaacag ctccacactt ttcatccctc ttctttgaat   2286
cggagaccac taaacgcatc tttgaagtag cgtatctat                          2325

<210> SEQ ID NO 2
<211> LENGTH: 381
<212> TYPE: PRT
<213> ORGANISM: Mus musculus

<400> SEQUENCE: 2

Met Gly Pro Gln Asn Arg Asn Thr Ser Phe Ala Pro Asp Leu Asn Pro
 1               5                  10                  15

Pro Gln Asp His Val Ser Leu Asn Tyr Ser Tyr Gly Asp Tyr Asp Leu
             20                  25                  30

Pro Leu Gly Glu Asp Glu Asp Val Thr Lys Thr Gln Thr Phe Phe Ala
         35                  40                  45

Ala Lys Ile Val Ile Gly Val Ala Leu Ala Gly Ile Met Leu Val Cys
     50                  55                  60

Gly Ile Gly Asn Phe Val Phe Ile Ala Ala Leu Ala Arg Tyr Lys Lys
 65                  70                  75                  80

Leu Arg Asn Leu Thr Asn Leu Leu Ile Ala Asn Leu Ala Ile Ser Asp
                 85                  90                  95

Phe Leu Val Ala Ile Val Cys Cys Pro Phe Glu Met Asp Tyr Tyr Val
            100                 105                 110

Val Arg Gln Leu Ser Trp Ala His Gly His Val Leu Cys Ala Ser Val
        115                 120                 125

Asn Tyr Leu Arg Thr Val Ser Leu Tyr Val Ser Thr Asn Ala Leu Leu
    130                 135                 140

Ala Ile Ala Ile Asp Arg Tyr Leu Ala Ile Val His Pro Leu Lys Pro
145                 150                 155                 160

Arg Met Asn Tyr Gln Thr Ala Ser Phe Leu Ile Ala Leu Val Trp Met
                165                 170                 175

Val Ser Ile Leu Ile Ala Val Pro Ser Ala Tyr Phe Thr Thr Glu Thr
            180                 185                 190
```

```
Ile Leu Val Ile Val Lys Asn Gln Glu Lys Ile Phe Cys Gly Gln Ile
        195                 200                 205

Trp Ser Val Asp Gln Gln Leu Tyr Tyr Lys Ser Tyr Phe Leu Phe Val
    210                 215                 220

Phe Gly Leu Glu Phe Val Gly Pro Val Val Thr Met Thr Leu Cys Tyr
225                 230                 235                 240

Ala Arg Ile Ser Gln Glu Leu Trp Phe Lys Ala Val Pro Gly Phe Gln
                245                 250                 255

Thr Glu Gln Ile Arg Lys Arg Leu Arg Cys Arg Arg Lys Thr Val Leu
            260                 265                 270

Leu Leu Met Gly Ile Leu Thr Ala Tyr Val Leu Cys Trp Ala Pro Phe
        275                 280                 285

Tyr Gly Phe Thr Ile Val Arg Asp Phe Phe Pro Thr Val Val Val Lys
    290                 295                 300

Glu Lys His Tyr Leu Thr Ala Phe Tyr Val Val Glu Cys Ile Ala Met
305                 310                 315                 320

Ser Asn Ser Met Ile Asn Thr Ile Cys Phe Val Thr Val Lys Asn Asn
                325                 330                 335

Thr Met Lys Tyr Phe Lys Lys Met Leu Arg Leu His Trp Arg Pro Ser
            340                 345                 350

His Tyr Gly Ser Lys Ser Ser Ala Asp Leu Asp Leu Lys Thr Ser Gly
        355                 360                 365

Val Pro Ala Thr Glu Glu Val Asp Cys Ile Arg Leu Lys
    370                 375                 380

<210> SEQ ID NO 3
<211> LENGTH: 2556
<212> TYPE: DNA
<213> ORGANISM: Mus musculus
<220> FEATURE:
<221> NAME/KEY: CDS
<222> LOCATION: (1)...(1182)
<220> FEATURE:
<221> NAME/KEY: misc_feature
<222> LOCATION: 1308, 1439, 1440
<223> OTHER INFORMATION: n = A,T,C or G

<400> SEQUENCE: 3 atg gag acc act gtc ggg gct ctg ggt gag aat acc aca gac acc ttc        48
Met Glu Thr Thr Val Gly Ala Leu Gly Glu Asn Thr Thr Asp Thr Phe
  1               5                  10                  15 acc gac ttc ttt tct gca ctc gat ggc cat gaa gcc caa acc ggc tcg        96
Thr Asp Phe Phe Ser Ala Leu Asp Gly His Glu Ala Gln Thr Gly Ser
                 20                  25                  30 tta cca ttc act ttc agc tac ggt gac tat gac atg ccc ctg gat gaa       144
Leu Pro Phe Thr Phe Ser Tyr Gly Asp Tyr Asp Met Pro Leu Asp Glu
             35                  40                  45 gag gaa gat gtg acc aat tct cgg act ttc ttt gct gcc aag att gtc       192
Glu Glu Asp Val Thr Asn Ser Arg Thr Phe Phe Ala Ala Lys Ile Val
         50                  55                  60 att ggc atg gct ttg gtg ggt atc atg cta gtg tgt ggc atc ggc aac       240
Ile Gly Met Ala Leu Val Gly Ile Met Leu Val Cys Gly Ile Gly Asn
 65                  70                  75                  80 ttc atc ttt atc act gcc ctg gcc cgc tac aaa aag ctc cgc aac ctc       288
Phe Ile Phe Ile Thr Ala Leu Ala Arg Tyr Lys Lys Leu Arg Asn Leu
                 85                  90                  95 acc aac ctg ctt atc gcc aac ctg gcc att tca gac ttc ctc gtg gcc       336
Thr Asn Leu Leu Ile Ala Asn Leu Ala Ile Ser Asp Phe Leu Val Ala
                100                 105                 110
```

-continued

| | |
|---|---|
| atc gtg tgc tgc ccc ttt gag atg gac tac tat gtg gtg cgc cag ctc<br>Ile Val Cys Cys Pro Phe Glu Met Asp Tyr Tyr Val Val Arg Gln Leu<br>115                    120                    125 | 384 |
| tcc tgg gag cat ggt cat gtc ctg tgc gcc tct gtc aac tac ttg cgt<br>Ser Trp Glu His Gly His Val Leu Cys Ala Ser Val Asn Tyr Leu Arg<br>130                    135                    140 | 432 |
| acc gtc tcc ctc tac gtc tcc act aac gcc cta ctg gcc att gcc att<br>Thr Val Ser Leu Tyr Val Ser Thr Asn Ala Leu Leu Ala Ile Ala Ile<br>145                    150                    155                    160 | 480 |
| gac agg tat ctg gcc att gtg cac ccg ctg aga ccg cgg atg aag tgt<br>Asp Arg Tyr Leu Ala Ile Val His Pro Leu Arg Pro Arg Met Lys Cys<br>                    165                    170                    175 | 528 |
| caa aca gcc gcc ggc ctg atc ttc ctg gtg tgg tca gta tcc atc ctc<br>Gln Thr Ala Ala Gly Leu Ile Phe Leu Val Trp Ser Val Ser Ile Leu<br>180                    185                    190 | 576 |
| atc gcc att cca gct gcc tac ttc acc act gag acc gtg ctg gtc atc<br>Ile Ala Ile Pro Ala Ala Tyr Phe Thr Thr Glu Thr Val Leu Val Ile<br>                    195                    200                    205 | 624 |
| gtg gag aga cag gag aag atc ttc tgt ggt cag atc tgg ccg gtg gat<br>Val Glu Arg Gln Glu Lys Ile Phe Cys Gly Gln Ile Trp Pro Val Asp<br>210                    215                    220 | 672 |
| cag cag ttc tac tac agg tcc tat ttc ctt ttg gtt ttc ggc ctc gag<br>Gln Gln Phe Tyr Tyr Arg Ser Tyr Phe Leu Leu Val Phe Gly Leu Glu<br>225                    230                    235                    240 | 720 |
| ttc gtg ggc ccc gta gtc gcc atg acc ttg tgc tat gcc agg gtg tcc<br>Phe Val Gly Pro Val Val Ala Met Thr Leu Cys Tyr Ala Arg Val Ser<br>                    245                    250                    255 | 768 |
| cgg gag ctc tgg ttc aag gcg gtg cca ggc ttc cag aca gag cag atc<br>Arg Glu Leu Trp Phe Lys Ala Val Pro Gly Phe Gln Thr Glu Gln Ile<br>260                    265                    270 | 816 |
| cgc cgg acg gtg cgc tgc cgc cgc agg acg gtg ctg ggg ctc gtg tgc<br>Arg Arg Thr Val Arg Cys Arg Arg Arg Thr Val Leu Gly Leu Val Cys<br>275                    280                    285 | 864 |
| gtc ctc tct gcc tat gtg ctg tgc tgg gct ccc ttc tat ggc ttc act<br>Val Leu Ser Ala Tyr Val Leu Cys Trp Ala Pro Phe Tyr Gly Phe Thr<br>290                    295                    300 | 912 |
| atc gtg cgt gac ttc ttc ccc tcc gtg ttt gtg aag gag aag cac tac<br>Ile Val Arg Asp Phe Phe Pro Ser Val Phe Val Lys Glu Lys His Tyr<br>305                    310                    315                    320 | 960 |
| ctc acc gcc ttc tat gtg gtg gag tgc atc gcc atg agc aac agc atg<br>Leu Thr Ala Phe Tyr Val Val Glu Cys Ile Ala Met Ser Asn Ser Met<br>                    325                    330                    335 | 1008 |
| atc aat acg ctc tgc ttt gtg act gtc agg aat aac acc agt aag tac<br>Ile Asn Thr Leu Cys Phe Val Thr Val Arg Asn Asn Thr Ser Lys Tyr<br>340                    345                    350 | 1056 |
| ctc aag agg atc ctg cgg ctt cag tgg agg gcc tct ccc agc ggg agc<br>Leu Lys Arg Ile Leu Arg Leu Gln Trp Arg Ala Ser Pro Ser Gly Ser<br>355                    360                    365 | 1104 |
| aag gcc agc gct gac ctc gac ctc agg acc acg gga ata cct gcc acc<br>Lys Ala Ser Ala Asp Leu Asp Leu Arg Thr Thr Gly Ile Pro Ala Thr<br>370                    375                    380 | 1152 |
| gag gag gtg gac tgc atc cga ctg aaa taa gcaaatggt accacagcgc<br>Glu Glu Val Asp Cys Ile Arg Leu Lys *<br>385                    390 | 1202 |
| ccgggtcgca cacagcagcc atgaacttgt ttttctgcgg aaggcagagg aaagagacaa | 1262 |
| ctacttagac acgctattca aggaccactg aagtgtggaa tttctnaaat ggagacctga | 1322 |
| gatactgtca ctagtggtca gggttcaccg aatatctaat ttttgcaaag actagacacc | 1382 |

-continued

```
agtgaaagtc ctttgacaaa gtaaagtggg gattatagca aggaaatatg gattgtnntg    1442
tctggaaaag gctatttcca gagagaaggc agagcaggct atgtaggact ctcctgtctc    1502
tgcttagggt ggagtacagg gctctgtgtg ggcctagctc acctctggca ggactcttgg    1562 gttttttgttt atgtctagca ttagcaagcc cggagcaaga gtatgaaga ggttcccaga    1622 tgtgctgtag tccttttctg cttacctcag aatccccact gagggaatc agaagcatga    1682 gtggacactc caggacccac ggctaagttc tgcgcatcca cccccaacct acggtcagat    1742
cttaggccta gggctctgca cacagacagt gggggagggg acttctttgg agcaccgact    1802
tgagggagga gccacttgga ctctgggtgc catttgcata gggaatttgg ggttctgagt    1862
cataagtttg agttcaggtg agcatgattc ccccactcat ggtctactca ctgcagggga    1922
aaaggaggtg aagaaggga gggtcaggtg ggacccctga aggcatgcgt gcaggttaaa    1982
ggatgctgtt gcttcatctc tcagcatctg tgccctggac cactcgtgct tcttgagact    2042
tcatgcctct gagtttatgg agcatagact catgaaggta aacgtagcac cttgctgtcc    2102
cgttcccact agctcccaaa caccggtgtt ttcatctcag gcagcctatt tgatgggatt    2162
ccctaactgg taagactggg agaaagattt cttaaccagt ggtacctgac tcttgacctg    2222
gtcatggtcc tgggaatgaa gacttgctgc tctttccaaa tgaaggtgac cttggagaaa    2282
tcaccacatt tctgctcttc agcgcacatg aagacttgca catcagggggt gctgcctgga    2342 cactcaggaa accgaagatg accaacagtg agctctaggg accccacaga cttatgaaag    2402
tctcatccca tgtgataact caccttctta gcttggcatt tagaattctg gcctgagaaa    2462
acctgaggcc tagctttgac taagtcatct acacagacct gagataagac tttctaaaga    2522
taaaggtaat acttaagaaa cctgttagaa ttgt                                2556
```

<210> SEQ ID NO 4
<211> LENGTH: 393
<212> TYPE: PRT
<213> ORGANISM: Mus musculus

<400> SEQUENCE: 4

```
Met Glu Thr Thr Val Gly Ala Leu Gly Glu Asn Thr Thr Asp Thr Phe
 1               5                  10                  15

Thr Asp Phe Phe Ser Ala Leu Asp Gly His Glu Ala Gln Thr Gly Ser
            20                  25                  30

Leu Pro Phe Thr Phe Ser Tyr Gly Asp Tyr Asp Met Pro Leu Asp Glu
        35                  40                  45

Glu Glu Asp Val Thr Asn Ser Arg Thr Phe Phe Ala Ala Lys Ile Val
    50                  55                  60

Ile Gly Met Ala Leu Val Gly Ile Met Leu Val Cys Gly Ile Gly Asn
65                  70                  75                  80

Phe Ile Phe Ile Thr Ala Leu Ala Arg Tyr Lys Lys Leu Arg Asn Leu
                85                  90                  95

Thr Asn Leu Leu Ile Ala Asn Leu Ala Ile Ser Asp Phe Leu Val Ala
            100                 105                 110

Ile Val Cys Cys Pro Phe Glu Met Asp Tyr Tyr Val Val Arg Gln Leu
        115                 120                 125

Ser Trp Glu His Gly His Val Leu Cys Ala Ser Val Asn Tyr Leu Arg
    130                 135                 140

Thr Val Ser Leu Tyr Val Ser Thr Asn Ala Leu Leu Ala Ile Ala Ile
145                 150                 155                 160

Asp Arg Tyr Leu Ala Ile Val His Pro Leu Arg Pro Arg Met Lys Cys
```

```
                165                 170                 175
Gln Thr Ala Ala Gly Leu Ile Phe Leu Val Trp Ser Val Ser Ile Leu
            180                 185                 190

Ile Ala Ile Pro Ala Ala Tyr Phe Thr Thr Glu Thr Val Leu Val Ile
            195                 200                 205

Val Glu Arg Gln Glu Lys Ile Phe Cys Gly Gln Ile Trp Pro Val Asp
            210                 215                 220

Gln Gln Phe Tyr Tyr Arg Ser Tyr Phe Leu Leu Val Phe Gly Leu Glu
225                 230                 235                 240

Phe Val Gly Pro Val Val Ala Met Thr Leu Cys Tyr Ala Arg Val Ser
                245                 250                 255

Arg Glu Leu Trp Phe Lys Ala Val Pro Gly Phe Gln Thr Glu Gln Ile
            260                 265                 270

Arg Arg Thr Val Arg Cys Arg Arg Thr Val Leu Gly Leu Val Cys
            275                 280                 285

Val Leu Ser Ala Tyr Val Leu Cys Trp Ala Pro Phe Tyr Gly Phe Thr
            290                 295                 300

Ile Val Arg Asp Phe Phe Pro Ser Val Phe Val Lys Glu Lys His Tyr
305                 310                 315                 320

Leu Thr Ala Phe Tyr Val Val Glu Cys Ile Ala Met Ser Asn Ser Met
                325                 330                 335

Ile Asn Thr Leu Cys Phe Val Thr Val Arg Asn Asn Thr Ser Lys Tyr
            340                 345                 350

Leu Lys Arg Ile Leu Arg Leu Gln Trp Arg Ala Ser Pro Ser Gly Ser
            355                 360                 365

Lys Ala Ser Ala Asp Leu Asp Leu Arg Thr Thr Gly Ile Pro Ala Thr
            370                 375                 380

Glu Glu Val Asp Cys Ile Arg Leu Lys
385                 390

<210> SEQ ID NO 5
<211> LENGTH: 81
<212> TYPE: PRT
<213> ORGANISM: Homo sapiens

<400> SEQUENCE: 5

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Val
        35                  40                  45

Pro Phe Phe Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Gln
65                  70                  75                  80

Lys

<210> SEQ ID NO 6
<211> LENGTH: 100
<212> TYPE: PRT
<213> ORGANISM: Homo sapiens

<400> SEQUENCE: 6

Ala Val Ile Thr Gly Ala Cys Asp Lys Asp Ser Gln Cys Gly Gly Gly
1               5                   10                  15
```

Met Cys Cys Ala Val Ser Ile Trp Val Lys Ser Ile Arg Ile Cys Thr
            20                  25                  30

Pro Met Leu Gly Asp Ser Cys His Pro Leu Thr Arg Lys Asn Asn Phe
        35                  40                  45

Gly Asn Gly Arg Gln Glu Arg Arg Lys Arg Lys Ser Lys Arg Lys
 50                  55                  60

Lys Glu Val Pro Phe Phe Gly Arg Arg Met His His Thr Cys Pro Cys
 65                  70                  75                  80

Leu Pro Gly Leu Ala Cys Leu Arg Thr Ser Phe Asn Arg Phe Ile Cys
                85                  90                  95

Leu Ala Gln Lys
            100

<210> SEQ ID NO 7
<211> LENGTH: 81
<212> TYPE: PRT
<213> ORGANISM: Mus musculus

<400> SEQUENCE: 7

Ala Val Ile Thr Gly Ala Cys Asp Lys Asp Ser Gln Cys Gly Gly Gly
 1               5                  10                  15

Met Cys Cys Ala Val Ser Ile Trp Val Lys Ser Ile Arg Ile Cys Thr
            20                  25                  30

Pro Met Gly Gln Val Gly Asp Ser Cys His Pro Leu Thr Arg Lys Val
        35                  40                  45

Pro Phe Trp Gly Arg Arg Met His His Thr Cys Pro Cys Leu Pro Gly
 50                  55                  60

Leu Ala Cys Leu Arg Thr Ser Phe Asn Arg Phe Ile Cys Leu Ala Arg
 65                  70                  75                  80

Lys

<210> SEQ ID NO 8
<211> LENGTH: 102
<212> TYPE: PRT
<213> ORGANISM: Mus musculus

<400> SEQUENCE: 8

Ala Val Ile Thr Gly Ala Cys Asp Lys Asp Ser Gln Cys Gly Gly Gly
 1               5                  10                  15

Met Cys Cys Ala Val Ser Ile Trp Val Lys Ser Ile Arg Ile Cys Thr
            20                  25                  30

Pro Met Gly Gln Val Gly Asp Ser Cys His Pro Leu Thr Arg Lys Ser
        35                  40                  45

His Val Ala Asn Gly Arg Gln Glu Arg Arg Arg Ala Lys Arg Lys
 50                  55                  60

Arg Lys Lys Glu Val Pro Phe Trp Gly Arg Met His His Thr Cys
 65                  70                  75                  80

Pro Cys Leu Pro Gly Leu Ala Cys Leu Arg Thr Ser Phe Asn Arg Phe
                85                  90                  95

Ile Cys Leu Ala Arg Lys
            100

<210> SEQ ID NO 9
<211> LENGTH: 86
<212> TYPE: PRT
<213> ORGANISM: Homo sapiens

```
<400> SEQUENCE: 9

Ala Val Ile Thr Gly Ala Cys Glu Arg Asp Val Gln Cys Gly Ala Gly
1               5                   10                  15

Thr Cys Cys Ala Ile Ser Leu Trp Leu Arg Gly Leu Arg Met Cys Thr
            20                  25                  30

Pro Leu Gly Arg Glu Gly Glu Glu Cys His Pro Gly Ser His Lys Val
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
                85

<210> SEQ ID NO 10
<211> LENGTH: 86
<212> TYPE: PRT
<213> ORGANISM: Mus musculus

<400> SEQUENCE: 10

Ala Val Ile Thr Gly Ala Cys Glu Arg Asp Ile Gln Cys Gly Ala Gly
1               5                   10                  15

Thr Cys Cys Ala Ile Ser Leu Trp Leu Arg Gly Leu Arg Leu Cys Thr
            20                  25                  30

Pro Leu Gly Arg Glu Gly Glu Glu Cys His Pro Gly Ser His Lys Ile
        35                  40                  45

Pro Phe Leu Arg Lys Arg Gln His His Thr Cys Pro Cys Ser Pro Ser
    50                  55                  60

Leu Leu Cys Ser Arg Phe Pro Asp Gly Arg Tyr Arg Cys Phe Arg Asp
65                  70                  75                  80

Leu Lys Asn Ala Asn Phe
                85

<210> SEQ ID NO 11
<211> LENGTH: 77
<212> TYPE: PRT
<213> ORGANISM: Xenopus laevis

<400> SEQUENCE: 11

Ala Val Ile Thr Gly Ala Cys Asp Lys Asp Val Gln Cys Gly Ser Gly
1               5                   10                  15

Thr Cys Cys Ala Ala Ser Ala Trp Ser Arg Asn Ile Arg Phe Cys Ile
            20                  25                  30

Pro Leu Gly Asn Ser Gly Glu Asp Cys His Pro Ala Ser His Lys Val
        35                  40                  45

Pro Tyr Asp Gly Lys Arg Leu Ser Ser Leu Cys Pro Cys Lys Ser Gly
    50                  55                  60

Leu Thr Cys Ser Lys Ser Gly Glu Lys Phe Leu Cys Ser
65                  70                  75

<210> SEQ ID NO 12
<211> LENGTH: 75
<212> TYPE: PRT
<213> ORGANISM: Bufonidae sp.

<400> SEQUENCE: 12

Ala Val Ile Thr Gly Ala Cys Asp Lys Asp Val Gln Cys Gly Ser Gly
1               5                   10                  15
```

```
Thr Cys Cys Ala Ala Ser Ala Trp Ser Arg Asn Ile Arg Phe Cys Ile
            20                  25                  30

Pro Leu Ser Gly Glu Asp Cys His Pro Ala Ser His Lys Val Pro Tyr
        35                  40                  45

Asp Gly Lys Arg Leu Ser Ser Leu Cys Pro Cys Lys Ser Gly Leu Thr
    50                  55                  60

Cys Ser Lys Ser Gly Lys Phe Lys Cys Ser
65                  70                  75
```

<210> SEQ ID NO 13
<211> LENGTH: 80
<212> TYPE: PRT
<213> ORGANISM: Serpentes sp.

<400> SEQUENCE: 13

```
Ala Val Ile Thr Gly Ala Cys Glu Arg Asp Leu Gln Cys Gly Lys Gly
1               5                   10                  15

Thr Cys Cys Ala Val Ser Leu Trp Ile Lys Ser Val Arg Val Cys Thr
            20                  25                  30

Pro Val Gly Thr Ser Gly Glu Asp Cys His Pro Ala Ser His Lys Ile
        35                  40                  45

Pro Phe Ser Gly Gln Arg Met His His Thr Cys Pro Cys Ala Pro Asn
    50                  55                  60

Leu Ala Cys Val Gln Thr Ser Pro Lys Lys Phe Lys Cys Leu Ser Lys
65                  70                  75                  80
```

<210> SEQ ID NO 14
<211> LENGTH: 4038
<212> TYPE: PRT
<213> ORGANISM: Homo sapiens

<400> SEQUENCE: 14

```
Thr Cys Cys Cys Ala Thr Gly Ala Gly Ala Thr Gly Gly Thr Ala Ala
1               5                   10                  15

Gly Cys Thr Cys Cys Ala Gly Gly Gly Gly Cys Thr Gly Gly
            20                  25                  30

Gly Thr Thr Cys Ala Thr Gly Thr Cys Thr Gly Thr Thr Thr Gly
        35                  40                  45

Cys Thr Cys Ala Cys Cys Thr Gly Thr Ala Cys Cys Cys
    50                  55                  60

Cys Ala Ala Thr Gly Cys Thr Cys Ala Cys Ala Cys Ala Ala Thr
65                  70                  75                  80

Ala Thr Cys Thr Gly Gly Ala Ala Thr Ala Thr Ala Gly Thr Ala Ala
                85                  90                  95

Gly Thr Cys Thr Thr Ala Gly Thr Thr Ala Ala Thr Ala Cys Cys Thr
            100                 105                 110

Gly Thr Gly Ala Ala Thr Ala Ala Ala Ala Ala Thr Thr
        115                 120                 125

Ala Thr Gly Gly Thr Thr Thr Cys Thr Ala Cys Cys Cys Ala Cys
    130                 135                 140

Cys Thr Ala Ala Ala Gly Ala Ala Ala Thr Ala Thr Ala
145                 150                 155                 160

Gly Cys Thr Thr Ala Cys Ala Cys Ala Thr Thr Ala Cys Thr Cys
                165                 170                 175

Ala Cys Thr Thr Cys Ala Gly Ala Gly Thr Cys Thr Thr Gly
            180                 185                 190
```

-continued

```
Thr Ala Thr Ala Ala Thr Thr Cys Thr Gly Gly Thr Ala Thr Ala Ala
        195                 200                 205

Ala Gly Ala Ala Thr Gly Cys Thr Gly Thr Ala Cys Thr Ala Gly Ala
    210                 215                 220

Ala Ala Ala Ala Ala Thr Ala Cys Ala Ala Ala Gly Gly Ala Ala Ala
225                 230                 235                 240

Thr Thr Ala Cys Ala Cys Ala Thr Thr Ala Thr Thr Ala Thr Thr Thr
                245                 250                 255

Ala Thr Ala Ala Thr Ala Gly Cys Ala Ala Thr Thr Ala Cys Thr Ala
            260                 265                 270

Ala Thr Ala Thr Ala Ala Thr Thr Cys Ala Ala Ala Gly Thr Thr Cys
        275                 280                 285

Ala Thr Thr Ala Thr Gly Cys Thr Cys Ala Thr Thr Ala Ala Gly Gly
    290                 295                 300

Ala Gly Thr Cys Cys Ala Ala Gly Cys Cys Ala Thr Gly Ala Ala Thr
305                 310                 315                 320

Gly Ala Thr Thr Cys Ala Thr Thr Thr Cys Cys Thr Gly Thr Ala Gly
                325                 330                 335

Ala Ala Thr Ala Thr Ala Gly Cys Ala Cys Thr Gly Cys Thr Cys Ala
            340                 345                 350

Cys Cys Thr Gly Ala Thr Ala Cys Cys Thr Thr Gly Thr Thr Gly Thr
        355                 360                 365

Cys Thr Thr Cys Ala Gly Ala Ala Ala Cys Cys Ala Gly Thr Gly Ala
    370                 375                 380

Cys Ala Gly Ala Cys Thr Thr Gly Cys Ala Cys Thr Gly Thr Cys Thr
385                 390                 395                 400

Gly Thr Cys Cys Cys Cys Thr Thr Gly Ala Ala Gly Ala Cys Ala Gly
                405                 410                 415

Ala Thr Thr Gly Thr Cys Ala Thr Gly Thr Gly Gly Cys Thr Thr Gly
            420                 425                 430

Thr Thr Thr Thr Gly Gly Thr Cys Ala Cys Thr Ala Ala Ala Ala Ala
        435                 440                 445

Gly Thr Gly Ala Gly Cys Ala Ala Ala Ala Gly Thr Gly Ala Cys Ala
    450                 455                 460

Gly Gly Cys Ala Thr Gly Ala Ala Thr Thr Cys Cys Ala Gly Gly Cys
465                 470                 475                 480

Ala Gly Ala Gly Ala Ala Ala Gly Cys Thr Gly Gly Thr Gly Thr Ala
                485                 490                 495

Cys Ala Ala Cys Cys Cys Thr Cys Thr Gly Gly Cys Thr Gly Cys Ala
            500                 505                 510

Cys Cys Cys Ala Ala Cys Thr Ala Thr Gly Thr Thr Ala Gly Thr Thr
        515                 520                 525

Thr Cys Cys Thr Gly Thr Gly Thr Cys Thr Gly Cys Cys Ala Thr Ala
    530                 535                 540

Ala Thr Gly Ala Ala Ala Thr Cys Ala Cys Cys Ala Cys Ala Ala Cys
545                 550                 555                 560

Thr Gly Gly Gly Thr Gly Gly Cys Thr Thr Ala Ala Ala Ala Cys Ala
                565                 570                 575

Ala Thr Ala Gly Ala Ala Ala Cys Thr Thr Ala Thr Thr Cys Thr Thr
            580                 585                 590

Thr Cys Gly Thr Gly Gly Thr Thr Cys Thr Gly Gly Ala Gly Gly Cys
        595                 600                 605
```

-continued

```
Thr Ala Ala Ala Ala Gly Thr Cys Cys Ala Ala Ala Cys Cys Ala
    610                 615                 620
Ala Gly Gly Gly Cys Thr Gly Ala Cys Ala Ala Gly Gly Cys Cys
625                 630                 635                 640
Gly Thr Gly Cys Thr Cys Cys Cys Thr Gly Thr Gly Ala Ala Gly Gly
                645                 650                 655
Ala Thr Cys Thr Gly Gly Gly Ala Ala Gly Ala Ala Thr Cys Cys
                660                 665                 670
Thr Thr Cys Cys Thr Thr Gly Cys Thr Cys Thr Thr Cys Ala Gly
            675                 680                 685
Ala Thr Cys Cys Thr Gly Ala Thr Gly Gly Cys Thr Gly Cys Thr Gly
    690                 695                 700
Gly Cys Ala Ala Thr Cys Cys Thr Thr Gly Gly Thr Gly Thr Thr Cys
705                 710                 715                 720
Cys Thr Thr Gly Cys Cys Thr Thr Gly Thr Ala Gly Ala Ala Gly Cys
                725                 730                 735
Ala Thr Gly Cys Thr Cys Cys Ala Ala Thr Cys Thr Cys Thr Gly
                740                 745                 750
Cys Cys Cys Cys Cys Ala Thr Cys Thr Thr Cys Ala Cys Thr Thr Gly
            755                 760                 765
Ala Thr Gly Thr Thr Cys Thr Cys Cys Gly Thr Gly Thr Gly Thr
    770                 775                 780
Gly Thr Gly Gly Gly Gly Gly Gly Gly Thr Gly Gly Gly Gly Thr
785                 790                 795                 800
Gly Gly Gly Gly Gly Gly Ala Gly Thr Cys Thr Ala Gly Cys Cys Thr
                805                 810                 815
Gly Thr Gly Thr Cys Thr Cys Thr Gly Thr Ala Thr Cys Cys Ala Gly
                820                 825                 830
Cys Thr Cys Thr Cys Cys Cys Thr Cys Cys Ala Thr Thr Thr Cys
            835                 840                 845
Thr Cys Thr Thr Ala Thr Gly Ala Ala Gly Cys Ala Cys Cys Ala
    850                 855                 860
Gly Cys Cys Ala Thr Thr Gly Ala Ala Thr Thr Ala Gly Ala Ala
865                 870                 875                 880
Cys Cys Cys Ala Cys Cys Thr Ala Ala Thr Ala Thr Ala Gly Cys
                885                 890                 895
Ala Thr Gly Ala Cys Cys Thr Cys Ala Thr Cys Thr Thr Ala Ala Gly
                900                 905                 910
Thr Thr Gly Ala Thr Ala Cys Gly Thr Cys Thr Gly Cys Ala Ala
            915                 920                 925
Ala Ala Ala Cys Cys Cys Thr Ala Thr Thr Cys Cys Ala Ala Ala
    930                 935                 940
Thr Ala Ala Gly Gly Thr Cys Ala Cys Gly Thr Cys Ala Cys Ala
945                 950                 955                 960
Gly Gly Thr Ala Cys Cys Ala Gly Gly Cys Thr Ala Gly Gly
                965                 970                 975
Cys Cys Thr Thr Gly Ala Ala Ala Thr Ala Ala Cys Thr Thr Gly
            980                 985                 990
Cys Thr Ala Gly Gly Gly Thr Cys Ala Cys Ala Gly Thr Ala Thr
    995                 1000                1005
Ala Gly Gly Cys Cys Ala Cys Thr Ala Cys Ala Cys Thr Gly Gly Cys
                1010                1015                1020
Ala Ala Thr Cys Ala Thr Gly Ala Ala Gly Cys Ala Cys Ala Thr Gly
```

-continued

```
                1025                1030                1035                1040
Thr Thr Gly Ala Ala Ala Thr Gly Gly Ala Gly Cys Cys Thr Ala
                1045                1050                1055
Thr Cys Ala Gly Thr Cys Ala Gly Cys Cys Thr Gly Ala Gly Thr Cys
            1060                1065                1070
Cys Cys Ala Ala Ala Thr Thr Gly Ala Cys Thr Gly Cys Cys Gly Thr
        1075                1080                1085
Gly Ala Gly Ala Cys Ala Gly Gly Cys Cys Thr Gly Thr Gly Thr Cys
    1090                1095                1100
Thr Cys Cys Cys Ala Gly Cys Thr Cys Ala Cys Thr Cys Thr Cys Ala Thr
1105                1110                1115                1120
Thr Thr Cys Ala Gly Thr Cys Ala Cys Gly Thr Gly Gly Cys Cys Cys
                1125                1130                1135
Cys Cys Ala Ala Gly Thr Ala Ala Gly Ala Gly Ala Cys Ala Gly
            1140                1145                1150
Gly Cys Thr Gly Ala Ala Thr Cys Ala Thr Cys Thr Gly Cys Ala Cys
        1155                1160                1165
Cys Ala Gly Gly Thr Ala Ala Gly Cys Thr Thr Cys Cys Ala Thr
    1170                1175                1180
Cys Thr Cys Thr Cys Thr Thr Gly Cys Thr Thr Thr Thr Gly Gly
1185                1190                1195                1200
Thr Gly Ala Cys Thr Ala Cys Cys Thr Thr Ala Ala Cys Gly Gly
                1205                1210                1215
Ala Thr Thr Cys Ala Thr Ala Thr Ala Cys Ala Thr Gly Ala Cys Ala
            1220                1225                1230
Thr Gly Ala Gly Thr Cys Thr Gly Thr Ala Cys Thr Gly Thr Ala Thr
        1235                1240                1245
Ala Thr Gly Ala Thr Cys Thr Thr Cys Thr Cys Gly Thr Ala Ala Cys
    1250                1255                1260
Thr Gly Thr Cys Thr Cys Gly Gly Ala Cys Thr Gly Thr Cys Cys
1265                1270                1275                1280
Thr Thr Cys Ala Thr Gly Gly Gly Ala Cys Ala Thr Ala Thr Cys
                1285                1290                1295
Cys Thr Gly Thr Thr Gly Cys Thr Gly Gly Thr Cys Ala Cys Thr Thr
            1300                1305                1310
Ala Cys Thr Gly Ala Ala Thr Gly Cys Cys Thr Gly Cys Cys Ala Thr
        1315                1320                1325
Ala Thr Gly Cys Cys Thr Ala Thr Ala Thr Cys Gly Thr Gly Cys
    1330                1335                1340
Thr Gly Thr Gly Thr Gly Cys Cys Ala Ala Gly Ala Gly Gly Gly Ala
1345                1350                1355                1360
Thr Gly Cys Ala Thr Ala Gly Ala Ala Ala Thr Thr Ala Gly Ala
            1365                1370                1375
Cys Ala Cys Ala Ala Gly Gly Ala Thr Cys Thr Ala Ala Thr Cys
        1380                1385                1390
Ala Thr Gly Ala Ala Ala Gly Thr Gly Thr Ala Cys Ala Ala Thr
    1395                1400                1405
Cys Thr Ala Ala Thr Ala Thr Ala Gly Thr Gly Gly Cys Ala Gly
1410                1415                1420
Gly Ala Cys Ala Gly Ala Ala Ala Gly Ala Cys Thr Thr Ala Thr
            1425                1430                1435                1440
Ala Thr Cys Ala Gly Cys Ala Thr Gly Gly Cys Thr Gly Ala Ala
        1445                1450                1455
```

-continued

```
Ala Thr Thr Gly Thr Cys Ala Gly Gly Gly Ala Gly Ala Cys Cys
            1460                1465                1470

Ala Ala Ala Thr Ala Ala Thr Ala Ala Gly Gly Cys Thr Thr Ala Ala
        1475                1480                1485

Thr Ala Ala Gly Ala Gly Gly Thr Ala Ala Cys Cys Cys Thr Ala Ala
    1490                1495                1500

Cys Ala Gly Ala Gly Cys Thr Cys Cys Ala Gly Thr Cys Thr Gly
1505                1510                1515                1520

Thr Thr Cys Cys Ala Gly Gly Cys Ala Cys Thr Gly Thr Gly Ala Thr
        1525                1530                1535

Ala Ala Gly Cys Ala Thr Thr Thr Gly Cys Ala Gly Gly Thr Ala
            1540                1545                1550

Thr Thr Ala Thr Thr Ala Ala Ala Thr Thr Cys Cys Ala Thr Ala Gly
        1555                1560                1565

Gly Gly Gly Thr Thr Gly Thr Ala Cys Cys Cys Ala Thr Gly Ala
            1570                1575                1580

Gly Gly Thr Thr Gly Gly Thr Ala Thr Thr Thr Ala Thr Ala Ala
1585                1590                1595                1600

Cys Cys Ala Thr Thr Thr Ala Cys Ala Ala Gly Ala Cys Cys Gly
            1605                1610                1615

Gly Ala Ala Ala Cys Ala Gly Ala Gly Gly Cys Thr Thr Cys Ala Ala
        1620                1625                1630

Ala Ala Gly Gly Thr Thr Gly Thr Gly Thr Ala Ala Cys Thr Thr Gly
        1635                1640                1645

Cys Cys Cys Ala Gly Thr Gly Gly Thr Cys Ala Cys Ala Cys Ala Gly
            1650                1655                1660

Gly Ala Thr Thr Cys Cys Ala Ala Thr Cys Cys Thr Gly Ala Thr Cys
1665                1670                1675                1680

Ala Gly Cys Cys Thr Gly Thr Cys Thr Ala Cys Ala Ala Ala Cys
        1685                1690                1695

Ala Thr Thr Gly Gly Gly Thr Thr Cys Thr Ala Thr Ala Gly Ala Cys
            1700                1705                1710

Gly Cys Thr Cys Cys Thr Ala Gly Ala Thr Thr Gly Cys Ala Thr Thr
        1715                1720                1725

Thr Thr Cys Gly Thr Thr Thr Ala Ala Gly Cys Thr Gly Ala Gly Cys
        1730                1735                1740

Cys Thr Thr Gly Ala Thr Gly Gly Thr Cys Thr Gly Cys Thr Gly Gly
1745                1750                1755                1760

Ala Ala Thr Ala Thr Gly Gly Thr Ala Gly Gly Cys Thr Ala Cys Ala
        1765                1770                1775

Cys Thr Thr Thr Ala Cys Ala Cys Ala Cys Ala Cys Ala Ala Gly Gly
        1780                1785                1790

Cys Thr Cys Ala Thr Thr Thr Cys Ala Cys Cys Thr Ala Ala Thr Ala
        1795                1800                1805

Cys Ala Gly Thr Thr Ala Thr Gly Cys Cys Thr Gly Gly Gly Cys Ala
        1810                1815                1820

Gly Ala Ala Gly Thr Gly Ala Thr Cys Ala Thr Gly Thr Gly Gly Cys
1825                1830                1835                1840

Ala Ala Thr Ala Thr Cys Ala Ala Cys Ala Gly Gly Thr Thr Ala Cys
            1845                1850                1855

Ala Gly Thr Ala Ala Thr Ala Gly Ala Ala Ala Gly Ala Ala Thr
        1860                1865                1870
```

-continued

```
Cys Ala Ala Thr Ala Ala Ala Cys Thr Ala Cys Thr Gly Thr Thr Thr
        1875                1880                1885

Cys Ala Thr Thr Thr Cys Thr Ala Thr Gly Thr Cys Ala Thr Thr Gly
    1890                1895                1900

Thr Thr Gly Cys Thr Ala Ala Gly Thr Thr Gly Thr Cys Cys Cys Ala
1905                1910                1915                1920

Ala Cys Thr Ala Cys Cys Thr Thr Thr Thr Thr Thr Ala Ala Thr Gly
                1925                1930                1935

Gly Ala Cys Thr Ala Ala Thr Cys Cys Ala Ala Ala Cys Thr Cys Thr
            1940                1945                1950

Thr Thr Thr Thr Thr Thr Thr Thr Thr Thr Cys Ala Thr Thr Thr Thr
        1955                1960                1965

Thr Cys Cys Cys Thr Thr Thr Ala Thr Ala Ala Cys Ala Ala Thr Thr
    1970                1975                1980

Gly Ala Ala Gly Thr Cys Ala Gly Ala Cys Thr Thr Cys Ala Thr Thr
1985                1990                1995                2000

Thr Thr Thr Cys Ala Ala Ala Cys Thr Thr Gly Gly Cys Cys Thr Cys
                2005                2010                2015

Ala Gly Ala Thr Ala Cys Ala Ala Ala Gly Ala Thr Gly Ala Cys Ala
            2020                2025                2030

Thr Ala Thr Cys Ala Ala Gly Ala Gly Cys Cys Thr Thr Cys Ala Thr
        2035                2040                2045

Thr Thr Cys Thr Cys Thr Cys Cys Thr Ala Ala Ala Gly Cys Ala Thr
    2050                2055                2060

Thr Ala Ala Ala Gly Cys Ala Ala Thr Thr Ala Ala Ala Ala Thr Thr
2065                2070                2075                2080

Thr Cys Cys Ala Ala Ala Ala Gly Ala Ala Cys Ala Thr Gly Ala Ala
                2085                2090                2095

Ala Cys Thr Ala Ala Ala Cys Ala Ala Cys Cys Cys Thr Ala Thr Thr
            2100                2105                2110

Thr Thr Thr Ala Ala Gly Thr Gly Thr Thr Thr Cys Cys Ala Ala Ala
        2115                2120                2125

Cys Thr Thr Ala Thr Thr Thr Cys Thr Thr Thr Thr Thr Thr Thr Thr
    2130                2135                2140

Ala Ala Ala Cys Thr Thr Gly Thr Thr Thr Cys Ala Ala Ala Ala Cys
2145                2150                2155                2160

Ala Gly Cys Cys Thr Thr Ala Thr Gly Ala Gly Gly Ala Cys Thr Gly
                2165                2170                2175

Thr Thr Thr Thr Cys Cys Ala Ala Ala Cys Ala Gly Cys Thr Gly Thr
            2180                2185                2190

Gly Thr Ala Ala Gly Ala Ala Gly Cys Cys Ala Gly Cys Cys Ala Cys
        2195                2200                2205

Thr Thr Thr Thr Gly Ala Ala Ala Thr Cys Thr Gly Ala Thr Thr Thr
    2210                2215                2220

Thr Thr Cys Cys Thr Gly Thr Gly Thr Ala Gly Ala Cys Ala Thr Ala
2225                2230                2235                2240

Thr Cys Ala Thr Ala Thr Thr Thr Thr Cys Thr Ala Thr Gly Cys Thr
                2245                2250                2255

Thr Gly Ala Ala Gly Ala Ala Gly Cys Ala Gly Gly Gly Ala Ala Thr
            2260                2265                2270

Ala Cys Cys Cys Ala Ala Gly Cys Thr Gly Gly Cys Ala Thr Thr Cys
        2275                2280                2285

Ala Ala Thr Ala Gly Thr Ala Gly Cys Gly Ala Ala Thr Ala Thr Gly
```

-continued

```
             2290                2295                2300
Ala Ala Ala Thr Ala Gly Ala Cys Cys Ala Thr Ala Ala Ala
2305                2310                2315                2320
Gly Ala Ala Ala Gly Thr Cys Ala Thr Ala Gly Gly Ala Ala Thr Gly
            2325                2330                2335
Thr Thr Ala Ala Ala Ala Thr Cys Cys Ala Thr Gly Thr Thr Gly Ala
            2340                2345                2350
Cys Thr Gly Gly Thr Thr Thr Thr Ala Cys Ala Thr Thr Thr Ala
            2355                2360                2365
Cys Cys Cys Gly Gly Cys Ala Gly Cys Ala Thr Cys Cys Cys Gly
            2370                2375                2380
Ala Gly Cys Thr Ala Gly Cys Gly Thr Thr Gly Gly Cys Ala Thr Gly
2385                2390                2395                2400
Gly Ala Gly Ala Cys Thr Gly Gly Ala Ala Ala Ala Gly Gly Ala Ala
            2405                2410                2415
Ala Cys Thr Thr Thr Cys Cys Ala Cys Ala Ala Gly Thr Cys Thr Gly
            2420                2425                2430
Thr Cys Ala Cys Thr Thr Gly Cys Thr Ala Cys Thr Gly Thr Thr Thr
            2435                2440                2445
Cys Thr Ala Cys Thr Thr Ala Cys Thr Cys Ala Cys Thr Gly Thr
            2450                2455                2460
Gly Ala Gly Thr Cys Cys Ala Ala Thr Thr Thr Thr Ala Ala Cys Ala
2465                2470                2475                2480
Thr Thr Thr Thr Thr Thr Thr Ala Ala Gly Thr Thr Gly Ala Ala Ala
            2485                2490                2495
Ala Ala Ala Gly Gly Gly Thr Thr Thr Gly Ala Cys Thr Cys Cys Thr
            2500                2505                2510
Thr Thr Thr Gly Thr Gly Thr Thr Thr Thr Cys Thr Gly Thr Thr Cys
            2515                2520                2525
Ala Ala Gly Gly Cys Gly Thr Thr Thr Thr Thr Ala Ala Ala Cys
            2530                2535                2540
Ala Thr Gly Ala Gly Ala Ala Cys Ala Cys Gly Thr Gly Thr Gly Ala
2545                2550                2555                2560
Ala Ala Ala Ala Gly Gly Thr Thr Thr Thr Ala Ala Ala Ala
            2565                2570                2575
Thr Cys Ala Gly Cys Cys Ala Ala Ala Gly Ala Thr Gly Gly Gly
            2580                2585                2590
Gly Thr Thr Thr Cys Cys Ala Ala Ala Thr Ala Thr Cys Ala Gly
            2595                2600                2605
Cys Thr Gly Thr Thr Thr Ala Ala Cys Ala Thr Cys Ala Gly Ala
            2610                2615                2620
Thr Ala Ala Thr Thr Gly Cys Cys Thr Gly Cys Cys Thr Thr Cys Cys
2625                2630                2635                2640
Cys Cys Cys Cys Gly Cys Thr Ala Thr Cys Cys Cys Cys Ala Cys
            2645                2650                2655
Ala Thr Thr Thr Cys Gly Thr Cys Thr Gly Ala Ala Thr Gly Cys Thr
            2660                2665                2670
Thr Thr Gly Gly Cys Ala Cys Gly Gly Gly Gly Gly Ala Gly Cys Cys
            2675                2680                2685
Cys Cys Ala Cys Ala Gly Thr Cys Thr Gly Ala Ala Ala Gly Thr Ala
            2690                2695                2700
Ala Cys Thr Cys Thr Gly Thr Cys Cys Cys Ala Ala Cys Thr Cys Thr
2705                2710                2715                2720
```

-continued

```
Cys Cys Thr Thr Ala Cys Thr Gly Cys Ala Thr Thr Thr Ala Thr Thr
                2725                2730                2735
Ala Ala Ala Gly Ala Gly Gly Cys Thr Gly Ala Ala Ala Gly Ala Cys
            2740                2745                2750

Gly Cys Ala Thr Cys Thr Gly Cys Thr Thr Thr Thr Cys Ala Ala Thr
        2755                2760                2765

Ala Gly Thr Thr Thr Gly Cys Gly Gly Thr Thr Cys Thr Thr Ala Ala
    2770                2775                2780

Gly Ala Gly Ala Cys Cys Ala Gly Gly Ala Ala Ala Gly Cys Cys Ala
2785                2790                2795                2800

Gly Ala Gly Gly Thr Thr Cys Thr Gly Ala Cys Thr Ala Thr Thr Cys
                2805                2810                2815

Ala Gly Gly Ala Ala Gly Ala Ala Ala Gly Thr Thr Gly Gly Gly Thr
            2820                2825                2830

Thr Thr Cys Cys Cys Ala Ala Ala Ala Cys Gly Gly Gly Cys Ala Ala
        2835                2840                2845

Gly Cys Ala Ala Gly Thr Thr Cys Gly Gly Thr Gly Thr Gly Gly Thr
    2850                2855                2860

Cys Ala Cys Ala Thr Cys Thr Ala Gly Gly Thr Ala Thr Thr Cys Thr
2865                2870                2875                2880

Thr Gly Ala Cys Gly Thr Cys Ala Thr Thr Thr Thr Thr Gly Thr Thr
                2885                2890                2895
Gly Ala Gly Gly Gly Ala Ala Ala Cys Ala Gly Gly Cys Thr Gly Cys
            2900                2905                2910

Ala Gly Thr Thr Thr Thr Thr Gly Gly Ala Gly Cys Cys Ala Gly Gly
        2915                2920                2925

Cys Thr Ala Gly Gly Ala Thr Gly Ala Gly Ala Gly Ala Thr Gly Gly
    2930                2935                2940
Ala Gly Gly Gly Cys Ala Ala Ala Thr Cys Thr Gly Thr Cys Ala Cys
2945                2950                2955                2960
Thr Thr Ala Thr Thr Cys Thr Thr Thr Cys Cys Thr Gly Gly Thr Gly
                2965                2970                2975

Thr Gly Cys Cys Thr Gly Gly Ala Ala Cys Cys Cys Ala Cys Thr Ala
            2980                2985                2990

Gly Ala Cys Ala Cys Thr Cys Ala Ala Thr Thr Cys Ala Thr Gly Thr
        2995                3000                3005

Thr Thr Ala Cys Gly Thr Gly Ala Ala Thr Gly Ala Ala Gly Gly Ala
    3010                3015                3020

Ala Thr Cys Ala Cys Ala Ala Thr Ala Ala Cys Gly Cys Cys Cys Thr
3025                3030                3035                3040
Ala Thr Cys Gly Cys Ala Thr Cys Thr Gly Thr Ala Ala Ala Ala Cys
                3045                3050                3055
Cys Gly Ala Ala Gly Gly Gly Thr Gly Ala Thr Thr Thr Thr Cys Cys
            3060                3065                3070

Thr Gly Gly Gly Cys Thr Gly Gly Ala Ala Ala Gly Thr Thr Thr Ala
        3075                3080                3085

Ala Gly Ala Ala Ala Gly Ala Ala Gly Ala Gly Ala Gly Ala Gly Cys
    3090                3095                3100

Thr Gly Cys Gly Thr Ala Cys Cys Thr Ala Gly Gly Gly Cys Thr Thr
3105                3110                3115                3120

Ala Ala Gly Gly Gly Gly Cys Cys Thr Cys Ala Gly Gly Cys Thr Gly
                3125                3130                3135
```

-continued

```
Gly Cys Ala Cys Thr Cys Gly Ala Ala Cys Cys Ala Gly Gly Cys
        3140                3145                3150
Gly Thr Thr Cys Thr Cys Ala Thr Thr Cys Cys Cys Thr Thr Thr
        3155                3160                3165
Gly Gly Cys Ala Thr Cys Ala Cys Cys Thr Gly Ala Ala Cys Gly
        3170                3175                3180
Gly Cys Thr Gly Thr Gly Cys Thr Gly Gly Ala Gly Cys Thr Gly
3185                3190                3195                3200
Gly Cys Gly Cys Gly Gly Gly Cys Thr Gly Ala Ala Gly Ala Gly
        3205                3210                3215
Gly Gly Gly Ala Gly Gly Ala Ala Thr Ala Cys Ala Thr Gly Thr
        3220                3225                3230
Gly Ala Gly Gly Ala Ala Ala Thr Cys Ala Gly Ala Gly Gly Ala
        3235                3240                3245
Gly Ala Gly Gly Gly Thr Cys Gly Gly Ala Ala Cys Ala Gly Ala
        3250                3255                3260
Thr Gly Thr Gly Gly Gly Cys Ala Thr Ala Ala Ala Gly Gly Ala
3265                3270                3275                3280
Ala Gly Gly Cys Cys Thr Cys Thr Gly Ala Cys Thr Thr Gly Ala
        3285                3290                3295
Ala Thr Ala Ala Ala Cys Ala Ala Ala Thr Ala Gly Gly Ala Gly Thr
        3300                3305                3310
Cys Cys Cys Gly Cys Ala Gly Cys Thr Gly Gly Ala Ala Gly Gly Ala
        3315                3320                3325
Cys Ala Ala Ala Thr Cys Cys Thr Thr Thr Cys Ala Cys Gly Thr Cys
        3330                3335                3340
Gly Cys Gly Gly Gly Thr Gly Ala Thr Gly Thr Gly Gly Gly Ala Thr
3345                3350                3355                3360
Thr Gly Gly Gly Gly Cys Gly Ala Thr Thr Thr Thr Gly Cys Thr Cys
        3365                3370                3375
Thr Cys Cys Cys Thr Thr Thr Gly Thr Thr Cys Thr Thr Thr Cys Cys
        3380                3385                3390
Cys Cys Thr Gly Cys Cys Thr Thr Cys Cys Ala Cys Gly Thr Thr Thr
        3395                3400                3405
Cys Cys Ala Gly Gly Gly Thr Ala Thr Thr Thr Gly Ala Thr Thr Gly
        3410                3415                3420
Ala Thr Gly Thr Cys Thr Gly Thr Cys Thr Cys Thr Cys Thr Gly
3425                3430                3435                3440
Thr Thr Ala Ala Gly Thr Thr Ala Thr Thr Cys Cys Ala Cys Cys Gly
        3445                3450                3455
Thr Gly Ala Gly Gly Ala Gly Ala Gly Cys Cys Gly Gly Thr
        3460                3465                3470
Gly Gly Cys Ala Gly Thr Ala Cys Cys Thr Gly Gly Cys Ala Cys Gly
        3475                3480                3485
Cys Ala Gly Cys Gly Gly Gly Cys Gly Cys Cys Ala Gly Thr Ala
        3490                3495                3500
Thr Ala Gly Ala Cys Cys Thr Gly Cys Thr Gly Ala Ala Cys Ala Ala
3505                3510                3515                3520
Ala Cys Gly Ala Ala Thr Gly Gly Ala Thr Thr Cys Ala Gly Gly Gly
        3525                3530                3535
Gly Cys Thr Gly Cys Thr Gly Thr Gly Thr Cys Cys Cys Cys Thr
        3540                3545                3550
Cys Ala Cys Cys Cys Ala Cys Cys Cys Cys Cys Gly Cys Cys Cys
```

-continued

```
             3555                3560                3565
Cys Cys Thr Ala Thr Gly Thr Gly Thr Cys Cys Ala Cys Ala Gly Cys
         3570                3575                3580
Gly Cys Cys Cys Gly Cys Ala Cys Gly Thr Ala Gly Thr Ala Gly
3585                3590                3595                3600
Gly Cys Gly Ala Cys Cys Cys Thr Ala Ala Cys Ala Thr Cys
         3605                3610                3615
Thr Gly Thr Ala Cys Ala Gly Cys Ala Ala Thr Gly Ala Thr Thr
         3620                3625                3630
Thr Gly Cys Ala Ala Gly Thr Thr Thr Cys Gly Gly Cys Gly Cys
         3635                3640                3645
Thr Gly Ala Gly Cys Ala Cys Gly Thr Gly Ala Gly Cys Thr Thr
         3650                3655                3660
Thr Gly Gly Ala Ala Cys Cys Ala Gly Gly Ala Cys Ala Gly Cys
3665                3670                3675                3680
Ala Ala Ala Thr Gly Ala Gly Thr Gly Thr Cys Gly Gly Ala
         3685                3690                3695
Gly Ala Cys Cys Ala Cys Ala Ala Ala Gly Cys Gly Gly Thr Thr
         3700                3705                3710
Cys Cys Gly Gly Cys Gly Cys Gly Thr Gly Cys Gly Ala Ala Gly
         3715                3720                3725
Gly Cys Gly Gly Thr Gly Gly Cys Thr Gly Gly Cys Gly Ala Cys
         3730                3735                3740
Gly Gly Cys Gly Gly Ala Gly Gly Ala Ala Cys Gly Gly Cys Gly
3745                3750                3755                3760
Cys Ala Gly Ala Gly Cys Gly Gly Gly Cys Gly Cys Cys Cys
         3765                3770                3775
Gly Cys Cys Gly Gly Ala Gly Cys Gly Cys Thr Gly Cys Cys Thr
         3780                3785                3790
Gly Cys Gly Thr Gly Cys Gly Cys Cys Gly Ala Gly Gly Cys
         3795                3800                3805
Gly Gly Gly Gly Gly Cys Gly Cys Gly Gly Gly Gly Cys Cys
         3810                3815                3820
Gly Cys Gly Cys Ala Thr Ala Gly Cys Ala Cys Gly Thr Gly Thr
3825                3830                3835                3840
Cys Gly Thr Cys Thr Gly Gly Ala Gly Cys Cys Gly Cys Cys
         3845                3850                3855
Gly Gly Gly Cys Cys Gly Ala Gly Cys Gly Gly Cys Gly Cys
         3860                3865                3870
Gly Cys Gly Thr Gly Thr Gly Cys Gly Cys Gly Thr Gly Gly Gly
         3875                3880                3885
Cys Gly Thr Gly Gly Gly Gly Thr Gly Thr Gly Thr Gly Cys Cys Cys
         3890                3895                3900
Gly Gly Gly Cys Cys Gly Thr Gly Cys Cys Cys Cys Gly Gly Cys
3905                3910                3915                3920
Gly Thr Gly Thr Gly Cys Thr Gly Cys Cys Gly Gly Gly Cys Gly Gly
         3925                3930                3935
Gly Cys Gly Cys Cys Gly Gly Cys Gly Thr Gly Ala Gly Thr Cys Ala
         3940                3945                3950
Cys Gly Gly Cys Gly Gly Gly Gly Cys Thr Ala Gly Cys Cys Thr Thr
         3955                3960                3965
Thr Ala Thr Ala Ala Cys Gly Gly Cys Cys Cys Gly Gly Ala Gly Gly
         3970                3975                3980
```

```
Cys Thr Cys Gly Cys Gly Gly Ala Gly Cys Cys Gly Cys Gly
3985                3990                3995                4000

Cys Gly Cys Cys Gly Thr Cys Cys Gly Cys Cys Cys Gly Cys Cys
            4005                4010                4015

Gly Cys Thr Cys Cys Gly Cys Gly Cys Thr Cys Cys Ala Cys Cys Cys
            4020                4025                4030

Ala Gly Cys Gly Cys Ala
        4035

<210> SEQ ID NO 15
<211> LENGTH: 2800
<212> TYPE: PRT
<213> ORGANISM: Homo sapiens

<400> SEQUENCE: 15

Thr Gly Thr Ala Cys Thr Gly Thr Ala Thr Gly Ala Thr Cys
 1                5                  10                  15

Thr Thr Cys Thr Cys Gly Thr Ala Ala Cys Thr Gly Thr Cys Thr Cys
                20                  25                  30

Thr Gly Gly Ala Cys Thr Gly Thr Cys Cys Thr Cys Ala Thr Gly
            35                  40                  45

Gly Gly Ala Cys Ala Thr Ala Thr Thr Cys Cys Thr Gly Thr Thr Gly
 50                  55                  60

Cys Thr Gly Gly Thr Cys Ala Cys Thr Thr Ala Cys Thr Gly Ala Ala
 65                  70                  75                  80

Thr Gly Cys Cys Thr Gly Cys Cys Ala Thr Ala Thr Gly Cys Cys Thr
                85                  90                  95

Ala Thr Thr Ala Thr Cys Gly Thr Gly Cys Thr Gly Thr Gly Thr Gly
                100                 105                 110

Cys Cys Ala Ala Gly Ala Gly Gly Ala Thr Gly Cys Ala Thr Ala
            115                 120                 125

Gly Ala Ala Ala Thr Thr Ala Gly Ala Cys Ala Cys Ala Ala Gly
        130                 135                 140

Gly Ala Thr Cys Cys Thr Ala Ala Thr Cys Ala Thr Gly Ala Ala Ala
145                 150                 155                 160

Ala Gly Thr Gly Thr Ala Cys Ala Ala Thr Cys Thr Ala Ala Thr Ala
                165                 170                 175

Thr Ala Gly Thr Gly Gly Cys Ala Gly Gly Ala Cys Ala Gly Ala
            180                 185                 190

Ala Ala Ala Gly Ala Cys Thr Thr Ala Thr Ala Thr Cys Ala Gly Cys
        195                 200                 205

Ala Thr Thr Gly Gly Cys Thr Gly Ala Ala Ala Thr Thr Gly Thr Cys
    210                 215                 220

Ala Gly Gly Gly Ala Gly Ala Cys Cys Ala Ala Ala Thr Ala Ala
225                 230                 235                 240

Thr Ala Ala Gly Gly Cys Thr Ala Ala Thr Ala Ala Gly Ala Gly
                245                 250                 255

Gly Thr Ala Ala Cys Cys Cys Thr Ala Ala Cys Ala Gly Ala Gly Cys
            260                 265                 270

Thr Cys Cys Cys Ala Gly Thr Cys Gly Thr Thr Cys Cys Ala Gly
        275                 280                 285

Gly Cys Ala Cys Thr Gly Thr Ala Thr Ala Ala Gly Cys Ala Thr
    290                 295                 300

Thr Thr Thr Gly Cys Ala Gly Gly Thr Ala Thr Thr Ala Thr Thr Ala
```

-continued

```
305                 310                 315                 320

Ala Ala Thr Thr Cys Cys Ala Thr Ala Gly Gly Gly Gly Thr Thr Gly
                325                 330                 335

Thr Ala Cys Cys Cys Cys Ala Thr Gly Ala Gly Gly Thr Thr Gly Gly
            340                 345                 350

Thr Ala Thr Thr Thr Thr Ala Thr Ala Ala Cys Cys Ala Thr Thr Thr
        355                 360                 365

Thr Ala Cys Ala Ala Gly Ala Cys Cys Gly Gly Ala Ala Ala Cys Ala
    370                 375                 380

Gly Ala Gly Gly Cys Thr Thr Cys Ala Ala Ala Ala Gly Gly Thr Thr
385                 390                 395                 400

Gly Thr Gly Thr Ala Ala Cys Thr Thr Gly Cys Cys Cys Ala Gly Thr
                405                 410                 415

Gly Gly Thr Cys Ala Cys Ala Cys Ala Gly Gly Ala Thr Thr Cys Cys
            420                 425                 430

Ala Ala Thr Cys Cys Thr Gly Ala Thr Cys Ala Gly Cys Cys Thr Gly
        435                 440                 445

Thr Cys Thr Cys Ala Cys Ala Ala Ala Cys Ala Thr Thr Gly Gly Gly
    450                 455                 460

Thr Thr Cys Thr Ala Thr Ala Gly Ala Cys Gly Cys Thr Cys Cys Thr
465                 470                 475                 480

Ala Gly Ala Thr Thr Gly Cys Ala Thr Thr Thr Thr Cys Gly Thr Thr
                485                 490                 495

Thr Ala Ala Gly Cys Thr Gly Ala Gly Cys Cys Thr Thr Gly Ala Thr
            500                 505                 510

Gly Gly Thr Cys Thr Gly Cys Thr Gly Gly Ala Ala Thr Ala Thr Gly
        515                 520                 525

Gly Thr Ala Gly Gly Cys Thr Ala Cys Ala Cys Thr Thr Thr Ala Cys
    530                 535                 540

Ala Cys Ala Cys Ala Cys Ala Ala Gly Gly Cys Thr Cys Ala Thr Thr
545                 550                 555                 560

Thr Cys Ala Cys Cys Thr Ala Ala Thr Ala Cys Ala Gly Thr Thr Ala
                565                 570                 575

Thr Gly Cys Cys Thr Gly Gly Gly Cys Ala Gly Ala Ala Gly Thr Gly
            580                 585                 590

Ala Thr Cys Ala Thr Gly Thr Gly Gly Cys Ala Ala Thr Ala Thr Cys
        595                 600                 605

Ala Ala Cys Ala Gly Gly Thr Thr Ala Cys Ala Gly Thr Ala Ala Thr
    610                 615                 620

Ala Gly Ala Ala Ala Ala Gly Ala Ala Thr Cys Ala Ala Thr Ala Ala
625                 630                 635                 640

Ala Cys Thr Ala Cys Thr Gly Thr Thr Thr Cys Ala Thr Thr Thr Cys
                645                 650                 655

Thr Ala Thr Gly Thr Cys Ala Thr Thr Gly Thr Thr Gly Cys Thr Ala
            660                 665                 670

Ala Gly Thr Thr Gly Thr Cys Cys Cys Ala Ala Cys Thr Ala Cys Cys
        675                 680                 685

Thr Thr Thr Thr Thr Thr Ala Ala Thr Gly Gly Ala Cys Thr Ala Ala
    690                 695                 700

Thr Cys Cys Ala Ala Ala Cys Thr Cys Thr Thr Thr Thr Thr Thr Thr
705                 710                 715                 720

Thr Thr Thr Thr Cys Ala Thr Thr Thr Thr Thr Cys Cys Cys Thr Thr
                725                 730                 735
```

```
Thr Ala Thr Ala Ala Cys Ala Ala Thr Thr Gly Ala Ala Gly Thr Cys
            740                 745                 750

Ala Gly Ala Cys Thr Thr Cys Ala Thr Thr Thr Thr Cys Ala Ala
            755                 760             765

Ala Cys Thr Thr Gly Gly Cys Cys Thr Cys Ala Gly Ala Thr Ala Cys
770             775                 780

Ala Ala Ala Gly Ala Thr Gly Ala Cys Ala Thr Ala Thr Cys Ala Ala
785                 790                 795                 800

Gly Ala Gly Cys Cys Thr Thr Cys Ala Thr Thr Thr Cys Thr Cys Thr
            805                 810                 815

Cys Cys Thr Ala Ala Ala Gly Cys Ala Thr Ala Ala Ala Gly Cys
            820                 825                 830

Ala Ala Thr Thr Ala Ala Ala Thr Thr Cys Cys Ala Ala Ala
            835                 840             845

Ala Gly Ala Ala Cys Ala Thr Gly Ala Ala Cys Thr Ala Ala Ala
            850                 855             860

Cys Ala Ala Cys Cys Cys Thr Ala Thr Thr Thr Thr Ala Ala Gly
865                 870                 875                 880

Thr Gly Thr Thr Thr Cys Cys Ala Ala Ala Cys Thr Ala Thr Thr
                885                 890                 895

Thr Cys Thr Thr Thr Thr Thr Thr Thr Ala Ala Cys Thr Thr
            900                 905                 910

Gly Thr Thr Thr Cys Ala Ala Ala Cys Ala Gly Cys Cys Thr Thr
            915                 920                 925

Ala Thr Gly Ala Gly Gly Ala Cys Thr Gly Thr Thr Thr Cys Cys
    930                 935                 940

Ala Ala Ala Cys Ala Gly Cys Thr Gly Thr Gly Ala Ala Gly Ala
945                 950                 955                 960

Ala Gly Cys Cys Ala Gly Cys Cys Ala Cys Thr Thr Thr Thr Gly Ala
            965                 970                 975

Ala Ala Thr Cys Thr Gly Ala Thr Thr Thr Thr Cys Cys Thr Gly
                980                 985                 990

Thr Gly Thr Ala Gly Ala Cys Ala Thr Ala Thr Cys Ala Thr Ala Thr
            995                 1000                1005

Thr Thr Thr Cys Thr Ala Thr Gly Cys Thr Thr Gly Ala Ala Gly Ala
    1010                1015                1020

Ala Gly Cys Ala Gly Gly Gly Ala Ala Thr Ala Cys Cys Cys Ala Ala
1025                1030                1035                1040

Gly Cys Thr Gly Gly Cys Ala Thr Thr Cys Ala Ala Thr Ala Gly Thr
            1045                1050                1055

Ala Gly Cys Gly Ala Ala Thr Ala Thr Gly Ala Ala Ala Thr Ala Gly
            1060                1065                1070

Ala Cys Cys Ala Thr Thr Ala Ala Ala Gly Ala Ala Ala Gly Thr
            1075                1080                1085

Cys Ala Thr Ala Gly Gly Ala Ala Thr Gly Thr Thr Ala Ala Ala Ala
            1090                1095                1100

Thr Cys Cys Ala Thr Gly Thr Thr Gly Ala Cys Thr Gly Gly Thr Thr
1105                1110                1115                1120

Thr Thr Thr Ala Cys Ala Thr Thr Thr Ala Cys Cys Cys Gly Gly Cys
                1125                1130                1135

Ala Gly Cys Ala Thr Thr Cys Cys Cys Gly Ala Gly Cys Thr Ala Gly
            1140                1145                1150
```

```
Cys Gly Thr Thr Gly Gly Cys Ala Thr Gly Ala Gly Ala Cys Thr
        1155                1160                1165
Gly Gly Ala Ala Ala Ala Gly Gly Ala Ala Cys Thr Thr Thr Cys
        1170                1175                1180
Cys Ala Cys Ala Ala Gly Thr Cys Thr Gly Thr Cys Ala Cys Thr
1185                1190                1195                1200
Gly Cys Thr Ala Cys Thr Gly Thr Thr Cys Thr Ala Cys Thr Thr
        1205                1210                1215
Ala Cys Thr Cys Cys Ala Cys Thr Gly Thr Ala Gly Thr Cys Cys
        1220                1225                1230
Ala Ala Thr Thr Thr Thr Ala Ala Cys Ala Thr Thr Thr Thr Thr
        1235                1240                1245
Thr Ala Ala Gly Thr Thr Gly Ala Ala Ala Ala Gly Gly Gly
        1250                1255                1260
Thr Thr Thr Gly Ala Cys Thr Cys Cys Thr Thr Thr Gly Thr Gly
1265                1270                1275                1280
Thr Thr Thr Thr Cys Thr Gly Thr Thr Cys Ala Ala Gly Cys Gly
        1285                1290                1295
Thr Thr Thr Thr Thr Thr Ala Ala Ala Cys Ala Thr Gly Ala Gly Ala
        1300                1305                1310
Ala Cys Ala Cys Gly Thr Gly Thr Gly Ala Ala Ala Ala Gly Gly
        1315                1320                1325
Thr Thr Thr Thr Ala Ala Ala Ala Ala Thr Cys Ala Gly Cys Cys
        1330                1335                1340
Ala Ala Ala Gly Ala Thr Thr Gly Gly Gly Gly Thr Thr Cys Cys
1345                1350                1355                1360
Ala Ala Ala Thr Ala Thr Thr Cys Ala Gly Cys Thr Gly Thr Thr Thr
        1365                1370                1375
Ala Ala Cys Ala Thr Thr Cys Ala Gly Ala Thr Ala Thr Thr Gly
        1380                1385                1390
Cys Cys Thr Gly Cys Cys Thr Thr Cys Cys Cys Cys Cys Gly Cys
        1395                1400                1405
Thr Ala Thr Cys Cys Cys Cys Ala Cys Ala Thr Thr Thr Cys Gly
        1410                1415                1420
Thr Cys Thr Gly Ala Ala Thr Gly Cys Thr Thr Thr Gly Gly Cys Ala
1425                1430                1435                1440
Cys Gly Gly Gly Gly Gly Ala Gly Cys Cys Cys Cys Ala Cys Ala Gly
        1445                1450                1455
Thr Cys Thr Gly Ala Ala Ala Gly Thr Ala Ala Cys Thr Cys Thr Gly
        1460                1465                1470
Thr Cys Cys Cys Ala Ala Cys Thr Cys Thr Cys Cys Thr Ala Cys
        1475                1480                1485
Thr Gly Cys Ala Thr Thr Thr Ala Thr Ala Ala Gly Ala Gly
        1490                1495                1500
Gly Cys Thr Gly Ala Ala Ala Gly Ala Cys Gly Cys Ala Cys Thr
1505                1510                1515                1520
Gly Cys Thr Thr Thr Thr Cys Ala Ala Thr Ala Gly Thr Thr Thr Gly
        1525                1530                1535
Cys Gly Gly Thr Thr Cys Thr Ala Ala Gly Ala Gly Ala Cys Cys
        1540                1545                1550
Ala Gly Gly Ala Ala Ala Gly Cys Cys Ala Gly Ala Gly Thr Thr
        1555                1560                1565
Cys Thr Gly Ala Cys Thr Ala Thr Thr Cys Ala Gly Gly Ala Ala Gly
```

-continued

```
            1570                1575                1580

Ala Ala Ala Gly Thr Thr Gly Gly Thr Thr Thr Cys Cys Cys Ala
1585                1590                1595                1600

Ala Ala Ala Cys Gly Gly Gly Cys Ala Ala Gly Cys Ala Ala Gly Thr
            1605                1610                1615

Thr Cys Gly Gly Thr Gly Thr Gly Gly Thr Cys Ala Cys Ala Thr Cys
                1620                1625                1630

Thr Ala Gly Gly Thr Ala Thr Cys Thr Gly Ala Cys Gly Thr
            1635                1640                1645

Cys Ala Thr Thr Thr Thr Thr Gly Thr Thr Gly Ala Gly Gly Ala
            1650                1655                1660

Ala Ala Cys Ala Gly Gly Cys Thr Gly Cys Ala Gly Thr Thr Thr Thr
1665                1670                1675                1680

Thr Gly Gly Ala Gly Cys Cys Ala Gly Cys Thr Ala Gly Gly Ala
                1685                1690                1695

Thr Gly Ala Gly Ala Gly Ala Thr Gly Gly Ala Gly Gly Cys Ala
                1700                1705                1710

Ala Ala Thr Cys Thr Gly Thr Cys Ala Cys Thr Thr Ala Thr Thr Cys
            1715                1720                1725

Thr Thr Thr Cys Cys Thr Gly Gly Thr Gly Gly Cys Cys Thr Gly
                1730                1735                1740

Gly Ala Ala Cys Cys Cys Ala Cys Thr Ala Gly Ala Cys Ala Cys Thr
1745                1750                1755                1760

Cys Ala Ala Thr Thr Cys Ala Thr Gly Thr Thr Thr Ala Cys Gly Thr
                1765                1770                1775

Gly Ala Ala Thr Gly Ala Ala Gly Gly Ala Ala Thr Cys Ala Cys Ala
                1780                1785                1790

Ala Thr Ala Ala Cys Gly Cys Cys Cys Thr Ala Thr Cys Gly Cys Ala
                1795                1800                1805

Thr Cys Thr Gly Thr Ala Ala Ala Cys Cys Gly Ala Ala Gly Gly
                1810                1815                1820

Gly Thr Gly Ala Thr Thr Thr Thr Cys Cys Thr Gly Gly Gly Cys Thr
1825                1830                1835                1840

Gly Gly Ala Ala Ala Gly Thr Thr Thr Ala Ala Gly Ala Ala Ala Gly
                1845                1850                1855

Ala Ala Gly Ala Gly Ala Gly Ala Gly Cys Thr Gly Cys Gly Thr Ala
                1860                1865                1870

Cys Cys Thr Ala Gly Gly Gly Cys Thr Thr Ala Ala Gly Gly Gly Gly
                1875                1880                1885

Cys Cys Thr Cys Ala Gly Gly Cys Thr Gly Gly Cys Ala Cys Thr Cys
                1890                1895                1900

Gly Ala Ala Cys Cys Ala Gly Gly Cys Gly Thr Thr Cys Thr Cys
1905                1910                1915                1920

Ala Thr Thr Thr Cys Cys Cys Thr Thr Thr Gly Gly Cys Ala Thr Cys
                1925                1930                1935

Ala Cys Cys Cys Thr Gly Ala Ala Cys Gly Gly Cys Thr Gly Thr Gly
                1940                1945                1950

Cys Cys Thr Gly Gly Ala Gly Cys Thr Gly Gly Cys Gly Gly Gly Gly
                1955                1960                1965

Gly Gly Cys Thr Gly Ala Ala Gly Ala Gly Gly Gly Ala Gly Gly
                1970                1975                1980

Ala Ala Ala Thr Ala Cys Ala Thr Gly Thr Gly Ala Gly Gly Ala Ala
1985                1990                1995                2000
```

-continued

```
Ala Ala Thr Cys Ala Gly Ala Gly Gly Ala Gly Gly Gly Thr
            2005                2010                2015

Cys Gly Gly Gly Ala Ala Cys Ala Gly Ala Thr Gly Thr Gly Gly Gly
            2020                2025                2030

Cys Ala Thr Ala Ala Gly Gly Gly Ala Ala Gly Gly Cys Cys Thr
            2035                2040                2045

Cys Thr Gly Ala Cys Thr Thr Gly Ala Ala Thr Ala Ala Ala Cys
            2050                2055                2060

Ala Ala Ala Thr Ala Gly Gly Ala Gly Thr Cys Cys Gly Cys Ala
2065                2070                2075                2080

Gly Cys Thr Gly Gly Ala Ala Gly Gly Ala Cys Ala Ala Thr Cys
            2085                2090                2095

Cys Thr Thr Thr Cys Ala Cys Gly Thr Cys Gly Cys Gly Gly Thr
            2100                2105                2110

Gly Ala Thr Gly Thr Gly Gly Gly Ala Thr Thr Gly Gly Gly Cys
            2115                2120                2125

Gly Ala Thr Thr Thr Thr Gly Cys Thr Cys Thr Cys Cys Thr Thr
            2130                2135                2140

Thr Gly Thr Thr Cys Thr Thr Thr Cys Cys Cys Cys Thr Gly Cys Cys
2145                2150                2155                2160

Thr Thr Cys Cys Ala Cys Gly Thr Thr Cys Cys Ala Gly Gly Gly
            2165                2170                2175

Thr Ala Thr Thr Thr Gly Ala Thr Thr Gly Ala Thr Gly Thr Cys Thr
            2180                2185                2190

Gly Thr Cys Thr Thr Cys Thr Cys Thr Gly Thr Thr Ala Ala Gly Thr
            2195                2200                2205

Thr Ala Thr Thr Cys Cys Ala Cys Cys Gly Thr Gly Ala Gly Gly Ala
            2210                2215                2220

Gly Ala Gly Ala Gly Cys Cys Gly Gly Thr Gly Gly Cys Ala Gly Thr
2225                2230                2235                2240

Ala Cys Cys Thr Gly Gly Cys Ala Cys Gly Cys Ala Gly Cys Gly Gly
            2245                2250                2255

Gly Cys Gly Cys Cys Cys Ala Gly Thr Ala Thr Ala Gly Ala Cys Cys
            2260                2265                2270

Thr Gly Cys Thr Gly Ala Ala Cys Ala Ala Ala Cys Gly Ala Ala Thr
            2275                2280                2285

Gly Gly Ala Thr Thr Cys Ala Gly Gly Gly Cys Thr Gly Cys Thr
            2290                2295                2300

Gly Thr Gly Thr Cys Cys Cys Cys Thr Cys Ala Cys Cys Cys Ala
2305                2310                2315                2320

Cys Cys Cys Cys Cys Cys Gly Cys Cys Cys Cys Thr Ala Thr Gly
            2325                2330                2335

Thr Gly Thr Cys Cys Ala Cys Ala Gly Cys Gly Cys Cys Cys Gly
            2340                2345                2350

Cys Ala Cys Gly Thr Ala Gly Thr Ala Gly Gly Cys Gly Ala Cys Cys
            2355                2360                2365

Cys Cys Thr Ala Ala Ala Cys Ala Thr Cys Thr Gly Thr Ala Cys Ala
            2370                2375                2380

Gly Cys Ala Ala Ala Thr Gly Ala Thr Thr Gly Cys Ala Ala Gly
2385                2390                2395                2400

Thr Thr Thr Thr Cys Gly Gly Cys Gly Cys Thr Gly Ala Gly Cys Ala
            2405                2410                2415
```

Cys Gly Thr Gly Gly Ala Gly Cys Thr Thr Gly Ala Ala Ala
                2420                2425                2430

Cys Cys Ala Gly Gly Ala Cys Ala Gly Cys Ala Ala Thr Gly Ala
2435                2440                2445

Gly Thr Gly Thr Cys Thr Cys Gly Gly Ala Gly Cys Cys Ala Cys
                2450                2455                2460

Ala Ala Ala Ala Gly Cys Gly Gly Thr Thr Cys Cys Gly Gly Cys Gly
2465                2470                2475                2480

Cys Gly Thr Gly Cys Gly Ala Ala Gly Gly Cys Gly Gly Thr Gly
                2485                2490                2495

Gly Cys Thr Gly Gly Cys Gly Ala Cys Gly Gly Cys Gly Gly Ala
                2500                2505                2510

Gly Gly Gly Ala Ala Cys Gly Gly Cys Gly Cys Ala Gly Ala Gly Cys
2515                2520                2525

Gly Gly Gly Gly Cys Gly Cys Cys Cys Cys Gly Cys Gly Gly Gly
                2530                2535                2540

Ala Gly Cys Gly Cys Thr Gly Cys Cys Thr Gly Cys Gly Thr Gly Gly
2545                2550                2555                2560

Cys Gly Cys Cys Cys Gly Ala Gly Gly Cys Gly Gly Gly Gly Cys
                2565                2570                2575

Gly Cys Gly Gly Gly Gly Gly Cys Cys Gly Cys Gly Cys Ala Thr
                2580                2585                2590

Ala Gly Cys Ala Cys Gly Thr Gly Cys Thr Cys Gly Thr Cys Thr Gly
2595                2600                2605

Gly Gly Ala Gly Cys Cys Gly Cys Cys Gly Cys Gly Cys Cys Gly
                2610                2615                2620

Ala Gly Gly Cys Gly Gly Gly Cys Gly Cys Gly Cys Thr Gly Thr
2625                2630                2635                2640

Gly Cys Gly Cys Gly Thr Gly Gly Gly Cys Gly Thr Gly Gly Gly
                2645                2650                2655

Gly Thr Gly Thr Gly Thr Gly Cys Cys Cys Gly Cys Gly Cys Cys Gly
2660                2665                2670

Thr Gly Cys Cys Cys Cys Cys Gly Cys Gly Thr Gly Thr Gly Cys
                2675                2680                2685

Thr Gly Cys Cys Gly Gly Gly Cys Gly Gly Gly Cys Gly Cys Cys Gly
2690                2695                2700

Gly Cys Gly Thr Gly Ala Gly Thr Cys Ala Cys Gly Gly Cys Gly Gly
2705                2710                2715                2720

Gly Gly Cys Thr Ala Gly Cys Cys Thr Thr Ala Thr Ala Ala Cys
                2725                2730                2735

Gly Gly Cys Cys Cys Gly Gly Ala Gly Gly Cys Thr Cys Gly Cys Gly
2740                2745                2750

Gly Gly Ala Gly Cys Cys Gly Cys Cys Gly Gly Cys Cys Cys Gly
                2755                2760                2765

Thr Cys Cys Gly Cys Cys Cys Gly Cys Gly Cys Thr Cys Cys Gly
                2770                2775                2780

Cys Gly Cys Thr Cys Cys Ala Cys Cys Cys Ala Gly Cys Gly Cys Ala
2785                2790                2795                2800

<210> SEQ ID NO 16
<211> LENGTH: 7349
<212> TYPE: DNA
<213> ORGANISM: Mus musculus

<400> SEQUENCE: 16

```
acacaagaaa gaagagggaa gagtgttcta gaccatcctg aaagtagata gccatagatc    60
agtggcccag gctctgcact actgttctct ggcaagtcac atgtggaggc tcagaaacat   120
ctgagatttg tggaaacaag tttaaagatt gagtatatgg aatactccca ccaaattgct   180
gtgtcttact tctagttatt ggccacccaa ggttttatg gcaatgttat aaatttgaag    240
agaaactcta acagttaaaa gcttggcacc agagcacact gggtttaaat ctagtttctt   300
tccttagcaa ttaccctggc ttgagatggc atggttgacc tttctaaatt ccactttgct   360
cttccataat ggccaagagt tctacccaga gggtccctgg ggttttata gaagatgtac    420
tggaattcac aaagtactta ctgtgtgcaa cgcatagctc tgcacttttg aaatgaaaac   480
accacaattg gcttgtgccc caaaacaaag aaacaaaaca aaataaagct aggagtcata   540
atgtgaaccc tagttcccta gcaagcctcc tgcctcagct tcctgaatgc tgggatttca   600
agctaagagc caccacatct ggttataaaa gttttgtacc tattatttca tatgtatatg   660
aatatgtctt gttacttctt ctaggtcctt tccttcttta aatgttgctg aatgaggttt   720
atttcgctgt gatagatagt tcctgttgac ctgaaaggat gataaagtaa ctacctagtc   780
atggttttta atcttaagaa acccctttc ttaggtgaga cttcttttt ttccatctgg     840
aaagttacca aatacgccac acatttgcat aacaatctct ttgaatgaag acagcagcgc   900
acgcagcacc agcttttgcc tttagggcca tcttcaatag aaaaaaata aaaaaataa     960
aaaagctgac agagaagagc agcgaacgtt ataatgagaa catctgaatc ttttagaacc  1020
aaatgttctt cggtgaccct tcatattatc tcaaagtcac ggtgtgctaa ttgcttgaag  1080
aaaacccttt ctccgggatt aatacttcag ctatttaaaa atagataaac tttactgtac  1140
attatcactt gaatgaaaca aatgcttttc agtgcctccg tagacaattg gcgttcacat  1200
tgaatcctgg tgatttatta ttttttttta aataaagaga aaatcatcag cattgaacta  1260
gattaaaata gacatcttat ttagaattat aaaagccatt ccttttcat gtcacattta   1320
aaatacggtt attatttag aatgatagca cagatgatat tataggttta acaagaagag   1380
ccacgtggaa cagtgcctca ataaaggatg aaggcaaagt agaaaggaga atatccatct  1440
tatttcattt gactttttt ttggaacaaa tctaaatgaa aagtcattta cacaaaggca   1500
aataaaaccc agtaatgaaa ttaccgggcc cacctattgt gttaccataa taagccataa  1560
gaaaaagacg catgcaaagt aaggtttcag caaagccaga gtcactctta acaacagagc  1620
catgtgagga agcgtctgga acagtttcct cttctgtggc tgagaaaatg cctgacactt  1680
tccgtgcaag atggagagca aggcctgtgt ttcttgatct ttctttgata acctcatcac  1740
tcttgatgaa gcatctactg tgtgctggat cattggaatc agttatagta aggttaatat  1800
gcaaaatagc aatcagtaag ccagaacttt gggcaatatc cgaaagtcca aaagaatgtg  1860
gattacatca gtgagttgga gtctgcgcag tacatctcac aggaagttca agcaaagaca  1920
gtggaggcaa gatcagtaag agtttgtaaa actgcagtat gagacagtac agagactcta  1980
ggctcttttt tttttttaa acacatgaat ctagaaacaa cagagctgga aaatagccca   2040
gtcataagca caacaaacta atttgctcac taggacccaa tgtgaagcaa gccagactga  2100
tgggtggtat acacacatca tccactgtgt ttgttcacaa gaacccgtgc aaaataagct  2160
ggaccagcga tggtatagta tacacatatc atctcaggca gagacaggca gatctctggg  2220
gctcgctggc cagccaacct agcttacccg gtgagtccca ggcctagtga aagaccctat  2280
ctcagaaaag aaggtagaag gctcttgaag aatgtcagct ggggctgtcc cctggcctcc  2340
```

```
acatgcaaag acgcagtgtg tgcccacgaa tgcgcacaca cacacacaca caacgaggaa    2400
tcagcaagct ttctctacac tagcagatag aagatatttt ttggcttttc caatcatgtg    2460
gtctcacaag tactcagtaa aaagcagaca cgggcaatac agaaacaggc atggctagat    2520
agaacataaa aaataaataa tagatagata gatagataga tagatagata gatagataga    2580
tagatagata gaatactggc tagttttgtg tcaacttgac acagctggag ttatcacaga    2640
gaggggagct tcagttgggg aaatgcctcc atgagataca actgtaaggc attttctcaa    2700
ttagtgatca agagggaaag gccccttgtg ggtgggacca tctctgggct ggtagtcttg    2760
ggttctataa gagagcaggc tgagcaagcc aggggaagga agacagtaag taacatccct    2820
ccatggcctc tgcattagct tctgcttcct gacctgcttg agttccagtc ctgacttcct    2880
ttggtgatga agagcagtat ggaagtgtaa gccgaataaa ccctttcctc cccaacttgc    2940
ttcttggtca tcatgtttgt acaagaatag aaaccctgac taagacagat agatagacaa    3000 caaaagcaa tgtgtcaacg ttttcccagt ttctactaaa tcctagtcat tgtggctaca    3060
ttctatgaaa tgaaaaaatt ttaaagtcca acaagaagcc actggttggc catttctttc    3120
tttagctcag ctgctccccc tcgcctgcc tgcctttgtc caatcccatg taagcaccag    3180
agtccctcct gcgagccagt taccacagtg aggttcctcc ttcctcccca ctcccaatag    3240
ttcctgccct tctttctctt gactgcccac aaggattctg cagtgctctg ccttcaggag    3300
atggatggtg acttctctca gtcctccatc atgctcttct ccacattcct agtgatttgg    3360
tcagccaaaa tcgagtgctt tgttcaattc ttggtacata gcttgtgctt agtaagtacc    3420
tgctgaatga gtgaatgaat gatggtctat tagttaaaac aaagcactct cagcttgcac    3480
atttgtactc tttcaccatg tatcacttga aggactaaac aaacaaatac agacacacat    3540
tatcctttgg agtaagaatt actaaggttg gccaaagtac agtggctcct ttcctgtagc    3600
actgcttacc agatttctgg tcttagcagc aactacattt gcactgctgt ctttagcaag    3660
gtgaactgtc acgtgacccg tttccgtcac tgtggcacag tcaggcttga gttccaggca    3720
gaggcagcag aaagctgaat tgcaaccctc cagccccacc cttccttta gtttcccaga    3780 ggttctagga gaagtgagca gaactaggtg gcatcgcaca tcagaggtta ttttcttgta    3840
gctctggatg ttagaagtcc aaaatcaagg atgctttccc cagctcttct gaattctgaa    3900
agccagctgt gggggaggag gtgtgtcata tcagtctcta tatccaaaga tcttgcatct    3960
gttataaaaa gatgggaaaa tagcttagtc agcaaagggc ttgcctcgaa aacattgatg    4020
tcctgagttc agtctccaga actcaaaaaa gccaggtgcg gtgacttgag tctgtggcta    4080
cctgagtctg taatcccaac aatggtaaaa tgggaggccg aggcaggcag atttcctgag    4140
gctcacagga cagtgaggct gacctacatg tcaaagttcc agtctagtga gagaccctgt    4200
cccaaacaaa aggtagaagc cgtctggtac tcaaggttgt ctgacctgca catatgctgt    4260
gtgtagaggt gcccacacat acacaaatgc atactcatgc atgcacagac acacacacac    4320
acaaaaccac acttttttaaa aaaaatgaca aagatatcag ttgttgggtt tagggcatac    4380
tctcatccag tatgacttca agtttggttg atcatatcag caaggaccct acttccaaat    4440
aaagacacag gaaccaggag ctagagtttc aacataactt tctaggtgag acttagtata    4500
accctagtct ggaatcatca taaatcatca gttcaaataa agtcccctc agctgagctc    4560 ccagagtgcc tgctgtagct tgaatgtgtg acagctgtaa gacatgtctc caggggcccc    4620
tcattccagt cccatattct tggaggaaac agcaggcgaa tccctgcac caggtctctc    4680 tttccctcta agcttttgct gcctgcattc gtgatccatg tagattaagt aagtgcatct    4740
```

```
acactgtgtg attcttgctt ctaacctctc tctgtccctg atcacaaaat ccactcctgg    4800
tgctcatcaa tcattgtctg agtgctggct aatgccacat gcaagaagga ttttcaggag    4860
aaatggactc ctagccagca cgtgtatgcg atctaattag gtgggcagga cagaaaacag    4920
ccgtatcagt gttcaatgaa cctatcaggg aaaagcacat gataagattt aactagagtg    4980
cacccccttg caggacttcc aggctatcac agacttggtg cttagcactt tcaaaggtgt    5040
tctctttgag cttcatggtg gctggaccag gaagttggta ttttatgccc acagggagcc    5100
agagacctta agaggtcaaa ggttcagttg ccacaaaaga ctccaatcca ggtcactcta    5160
actttcaaat gtagggttct tcgtatcaca ctgtcaaacc agctgagagg tggtagtcat    5220
gcaagactgc cagctatata tactctgaac ccacgaagtt ttggtcctca cccaaaggtt    5280
gttcctggct aatttgacca caatgactga tcgaaccaac aggttgcagt aacaaaacag    5340
aacttgaatt tcattattgt tttatcgttg tcttacggtg gggaggagtg taattcaaac    5400
agtgtctttc catttctaat aaatgaaatc agacttgatc taacttacct gtggggtcca    5460
aagaagttct gttgaagagt tttcatttct tctatcaagt attaaagcca ttaaacccctt    5520 ccaaagaggt ttagggggta gccgagcagt agaattgacc caggatgtcc atgcccttgg    5580
ttgcaacctc agcacaggaa acagaagag ccttaaaacca gtcttatgtt taagcatctc    5640
taaccttgat tcaaaagtct taggagactg ttttgggaac agtcaatctc aatggaaggt    5700
tagcatttcc ctgggtagag atggcctgtt ttctacgctc tgagaagtag ggaatacccca    5760 gttggcattt gatagtaaca aatatgaaac cgaccattta agaaaagaat taaaagagtg    5820
tcaggaatgt taaagttcat gttgactggt ttttacatt cccccgggct gcactcccat    5880
gccttcgttg gcatggagac tggaaaggaa actttccacc agtctgtcac ttgctactgt    5940
ttccacttag tttactgtga atccactttt aacagttttc tcaaagttaa aaaggagttt    6000
gatcccgggt gtgttttcgg tctcaggatg cttcttgaac tcaaaaacat ggtacaaaaa    6060
ggctttaaaa ctcagccaaa gatctagggt ttgaaacgcc cagctgttta acattcaaat    6120
aattccctgg cccctttgttc attttttttc ccctctacat ttcgtctgaa tgctttggca    6180
tgagggagcc cacagactga agtaactgt ggcccagctc tccttactgt attgattaaa    6240
gtggctgaaa aggcccatct gccttcagc agtctgtggt cctatgggac atgggaaagt    6300
ctaaggtccc tagctgtcta ggagtgaggt gggctccccc aaacctcaga aaaagtcaaa    6360
ttgatcatcc ttgtagaagc aagcaagatg agattattgg agccaaatta ggaacacaga    6420
gagggttgtc tcttgtctca tgggatgaat gcctagagtc cagcagacac acctaagtga    6480
ttgatcagaa cccccaccac caccaccaaa aaaaaatata tatatatgta taagacttgg    6540
agtttcctag gctggagaac cgagctggga gagagccacc ttcccagggc tcaggctgg    6600 cagagcaagc tgggagttct cctttttttcc cccctttggca acatcctgtt ctgcctgaag    6660
caggctggaa gctgcagagg ggagggaacg cacgtgagag aaatcagggc agaaagggtc    6720
aggaacagat gtgggcaccg gagaagtcat ttccaaaaag gaaaggagac tcccacagct    6780
ggaggggcag ccgagtccct ccaacttctt aagagatgtg ggacggggtg tgctggcgct    6840
ttgttcttcc agcctgctat gttcgcttgc cctttgcttg tttgtctgtt ctttctatgt    6900
tgtgccacct cagggcagag ccggtggcag tacctggcac gcacggatct ctcactgtag    6960
atatgctgaa caaatgtgta caaatacagt gcagttgtgt ccgccgcgtc tggcacgtcg    7020
tgggtacccc ctgcacatct gtatggcaaa tgatgtgcct ctgcgagtgt gggggctgag    7080
```

```
cacgtgaggc tctggaaaac aggacggcga aggaggaggg tttctgagac cacaaaagct    7140
tcaggaaggc tggctagggc tgcggcgccc cgcggggggct ctgcccgcgt ggcgctttgc   7200
gcgtggggcg cggggcacgt gcgcgtgtgc gcgtggagcg cggggtgtgt gcccgcgccg    7260 tgcccccccgc gtgctgcctg gcgtgagtca ccgcggggct cgcctttata accgccgcca   7320
ggctcgcagc tccgcagagc agcccggcc                                     7349

<210> SEQ ID NO 17
<211> LENGTH: 2800
<212> TYPE: DNA
<213> ORGANISM: Mus musculus

<400> SEQUENCE: 17
cagctgagct cccagagtgc ctgctgtagc ttgaatgtgt gacagctgta agacatgtct     60 ccagggccc ctcattccag tcccatattc ttggaggaaa cagcaggcga atcccctgca    120
ccaggtctct ctttccctct aagcttttgc tgcctgcatt cgtgatccat gtagattaag   180
taagtgcatc tacactgtgt gattcttgct tctaacctct ctctgtccct gatcacaaaa   240
tccactcctg gtgctcatca atcattgtct gagtgctggc taatgccaca tgcaagaagg   300
attttcagga gaaatggact cctagccagc acgtgtatgc gatctaatta ggtgggcagg   360
acagaaaaca gccgtatcag tgttcaatga acctatcagg gaaaagcaca tgataagatt   420
taactagagt gcaccccctt gcaggacttc caggctatca cagacttggt gcttagcact   480
ttcaaaggtg ttctctttga gcttcatggt ggctggacca ggaagttggt attttatgcc   540
cacagggagc cagagacctt aagaggtcaa aggttcagtt gccacaaaag actccaatcc   600
aggtcactct aactttcaaa tgtagggttc ttcgtatcac actgtcaaac cagctgagag   660
gtggtagtca tgcaagactg ccagctatat atactctgaa cccacgaagt tttggtcctc   720
acccaaaggt tgttcctggc taatttgacc acaatgactg atcgaaccaa caggttgcag   780
taacaaaaca gaacttgaat tcattattg ttttatcgtt gtcttacggt ggggaggagt    840
gtaattcaaa cagtgtcttt ccatttctaa taaatgaaat cagacttgat ctaacttacc   900
tgtggggtcc aaagaagttc tgttgaagag ttttcatttc ttctatcaag tattaaagcc   960
attaaaccct tccaaagagg tttaggggggt agccgagcag tagaattgac ccaggatgtc   1020
catgcccttg gttgcaacct cagcacagga aaacagaaga gccttaaacc agtcttatgt   1080
ttaagcatct ctaaccttga ttcaaaagtc ttaggagact gttttgggaa cagtcaatct   1140
caatggaagg ttagcatttc cctgggtaga gatggcctgt tttctacgct ctgagaagta   1200 gggaatacc agttggcatt tgatagtaac aaatatgaaa ccgaccattt aagaaaagaa    1260 ttaaagagt gtcaggaatg ttaaagttca tgttgactgg ttttttacatt tcccccgggc   1320 tgcactccca tgccttcgtt ggcatggaga ctggaaagga aactttccac cagtctgtca   1380
cttgctactg ttttccactta gtttactgtg aatccacttt taacagtttt ctcaaagtta  1440
aaaaggagtt tgatcccggg tgtgttttcg gtctcaggat gcttcttgaa ctcaaaaaca   1500
tggtacaaaa aggctttaaa actcagccaa agatctaggg tttgaaacgc ccagctgttt   1560
aacattcaaa taattccctg gccctttgtt catttttttt cccctctaca tttcgtctga   1620
atgctttggc atgagggagc ccacagactg aaagtaactg tggcccagct ctccttactg   1680
tattgattaa agtggctgaa aaggcccatc tgcctttcag cagtctgtgg tcctatggga   1740
catgggaaag tctaaggtcc ctagctgtct aggagtgagg tgggctcccc caaacctcag   1800
aaaaagtcaa attgatcatc cttgtagaag caagcaagat gagattattg gagccaaatt   1860
```

```
aggaacacag agagggttgt ctcttgtctc atgggatgaa tgcctagagt ccagcagaca    1920
cacctaagtg attgatcaga accccccacca ccaccaccaa aaaaaaatat atatatatgt    1980
ataagacttg gagtttccta ggctggagaa ccgagctggg agagagccac cttcccaggg    2040
cctcaggctg gcagagcaag ctgggagttc tcctttttc ccccttggc aacatcctgt      2100 tctgcctgaa gcaggctgga agctgcagag gggagggaac gcacgtgaga gaaatcaggg    2160
cagaaagggt caggaacaga tgtgggcacc ggagaagtca tttccaaaaa ggaaaggaga    2220
ctcccacagc tggaggggca gccgagtccc tccaacttct taagagatgt gggacggggt    2280
gtgctggcgc tttgttcttc cagcctgcta tgttcgcttg ccctttgctt gtttgtctgt    2340
tctttctatg ttgtgccacc tcagggcaga gccgtggca gtacctggca cgcacggatc     2400
tctcactgta gatatgctga acaaatgtgt acaaatacag tgcagttgtg tccgccgcgt    2460
ctggcacgtc gtgggtaccc cctgcacatc tgtatggcaa atgatgtgcc tctgcgagtg    2520
tgggggctga gcacgtgagg ctctggaaaa caggacggcg aaggaggagg gtttctgaga    2580
ccacaaaagc ttcaggaagg ctggctaggg ctgcggcgcc ccgcggggc tctgcccgcg     2640 tggcgctttg cgcgtggggc gcggggcacg tgcgcgtgtg cgcgtggagc gcggggtgtg    2700
tgcccgcgcc gtgccccccg cgtgctgcct ggcgtgagtc accgcggggc tcgcctttat    2760
aaccgccgcc aggctcgcag ctccgcagag cagcccggcc                          2800

<210> SEQ ID NO 18
<211> LENGTH: 188
<212> TYPE: DNA
<213> ORGANISM: Mus musculus

<400> SEQUENCE: 18
gcggcgcccc gcgggggctc tgcccgcgtg gcgctttgcg cgtggggcgc ggggcacgtg      60
cgcgtgtgcg cgtggagcgc ggggtgtgtg cccgcgccgt gccccccgcg tgctgcctgg    120
cgtgagtcac cgcggggctc gcctttataa ccgccgccag gctcgcagct ccgcagagca    180
gcccggcc                                                             188

<210> SEQ ID NO 19
<211> LENGTH: 72
<212> TYPE: DNA
<213> ORGANISM: Artificial Sequence
<220> FEATURE:
<223> OTHER INFORMATION: promoter

<400> SEQUENCE: 19
agccagcacg tgtatgcggg aacgcacgtg agagaagctg agcacgtgag gctcgcgggg      60
cacgtgcgcg tg                                                         72

<210> SEQ ID NO 20
<211> LENGTH: 81
<212> TYPE: PRT
<213> ORGANISM: Artificial Sequence
<220> FEATURE:
<223> OTHER INFORMATION: chimera

<400> SEQUENCE: 20

Ala Val Ile Thr Gly Ala Cys Glu Arg Asp Val Gln Cys Gly Ala Gly
 1               5                  10                  15

Thr Cys Cys Ala Ile Ser Leu Trp Leu Arg Gly Leu Arg Met Cys Thr
            20                  25                  30
```

```
Pro Leu Gly Arg Glu Gly Glu Cys His Pro Gly Ser His Lys Val
        35                  40                  45

Pro Phe Phe Gly Arg Arg Met His His Thr Cys Pro Cys Leu Pro Gly
    50                  55                  60

Leu Ala Cys Leu Arg Thr Ser Phe Asn Arg Phe Ile Cys Leu Ala Gln
65                  70                  75                  80

Lys

<210> SEQ ID NO 21
<211> LENGTH: 86
<212> TYPE: PRT
<213> ORGANISM: Artificial Sequence
<220> FEATURE:
<223> OTHER INFORMATION: chimera

<400> SEQUENCE: 21

Ala Val Ile Thr Gly Ala Cys Asp Lys Asp Ser Gln Cys Gly Gly Gly
1               5                   10                  15

Met Cys Cys Ala Val Ser Ile Trp Val Lys Ser Ile Arg Ile Cys Thr
            20                  25                  30

Pro Met Gly Lys Leu Gly Asp Ser Cys His Pro Leu Thr Arg Lys Val
        35                  40                  45

Pro Phe Phe Arg Lys Arg Lys His His Thr Cys Pro Cys Leu Pro Asn
    50                  55                  60

Leu Leu Cys Ser Arg Phe Pro Asp Gly Arg Tyr Arg Cys Ser Met Asp
65                  70                  75                  80

Leu Lys Asn Ile Asn Phe
                85
```

SCREENING METHODS FOR IDENTIFYING AGENTS THAT MODULATE OUTPUT OF A CIRCADIAN PACEMAKER

This application claims benefit of the filing date of U.S. Provisional Application No. 60/372,836, filed Apr. 15, 2002, and which is incorporated herein by reference.

This invention was made with government support under grant number NIMH57889 awarded by the National Institutes of Health. The United States Government has certain rights in this invention.

BACKGROUND OF THE INVENTION

The daily rhythm of life is maintained by a circadian clock in organisms ranging from bacteria to humans. The time kept by a circadian clock enables the organism to respond physiologically and influences its behavior to daily environmental fluctuations. In humans, circadian rhythms help coordinate the timing of our internal bodily functions, including sleep, as well as our interactions with the external world. Virtually all known physiologic parameters and cellular activities are influenced by the body's circadian clock.

Only recently has the medical community, as well as the general public, become aware of the importance of circadian rhythms for human health, safety, performance and productivity. It is now recognized that physical and mental impairments are associated with night-work, which involves over 20% of the work force in industrialized countries. People who work late-night shifts often have problems falling asleep, staying asleep, or waking up. More than 25 million Americans have non-traditional work schedules, and it is estimated that 60 to 70 percent of these people have a chronic sleeping problem. In addition, many industries will employ increasing numbers of workers around the clock (for example, transportation, utilities, public safety, heavy manufacturing and many service industries).

Normal sleep depends on properly functioning circadian rhythm. In humans, obtaining less than the required number of hours of sleep, particularly over several nights, leads to a decreased ability to retain new information, impaired productivity, altered mood, lowered resistance to infection and an increased susceptibility to accidents. Sleep-related traffic accidents annually claim thousands of lives, and operator fatigue has also been shown to play a contributory role in airplane crashes and other catastrophic accidents.

The pharmaceutical industry is now investigating the importance of circadian rhythms for the timing of drug delivery and is interested in developing drugs that could affect the circadian clock of humans, as well as agricultural plants and animals. Numerous health problems, including some forms of depression as well as many sleep, neurological, cardiovascular and endocrine disorders, have recently been associated with circadian rhythm dysfunctions.

In addition, as the elderly continue to become a greater percentage of the population in the United States, as well as in the rest of the world, more and more circadian abnormalities are being observed in older people suffering from various sleep, mental and physical disorders.

Thus, there exists a need to identify molecules associated with circadian rhythm and methods for identifying new therapeutic agents that can be used to modulate circadian rhythm. The present invention satisfies these needs and provides related advantages as well.

SUMMARY OF THE INVENTION

The invention provides a method for screening for a compound for modulating circadian rhythm. The method involves (a) providing a compound that is a Prokineticin 2 (PK2) receptor antagonist or agonist; and (b) determining the ability of the compound to modulate one or more indicia of circadian rhythm function, wherein a compound that modulates one or more indicia of circadian rhythm function is identified as a compound for modulating circadian rhythm.

In one embodiment, the provided PK2 receptor antagonist can be identified by contacting a receptor selected from PK2 receptor and PK1 receptor with one or more candidate compounds under conditions wherein PK2 promotes a predetermined signal and identifying a compound that reduces the predetermined signal.

In another embodiment, the provided PK2 receptor agonist can be identified by contacting a receptor selected from PK2 receptor and PK1 receptor with one or more candidate compounds under conditions wherein PK2 promotes a predetermined signal and identifying a compound that promotes the predetermined signal, for example, calcium ion mobilization.

In a further embodiment, the provided PK2 receptor antagonist can be identified by contacting a receptor selected from PK2 receptor and PK1 receptor with one or more candidate compounds in the presence of a receptor agonist under conditions wherein the agonist binds to the selected receptor and identifying a compound that reduces the binding.

In yet another embodiment, the provided PK2 receptor agonist can be identified by contacting a receptor selected from PK2 receptor and PK1 receptor with one or more candidate compounds under conditions wherein PK2 binds to a selected receptor and identifying a compound that binds to and activates the selected receptor.

The invention also provides a method for modulating circadian rhythm of an animal. The method involves administering to the animal an effective amount of a PK2 receptor antagonist or agonist, such as PK2, PK1 or a compound. Such treatment can be used to improve circadian rhythm disorders such as disorders of sleep/wakefulness rhythms and seasonal disorders. Exemplary conditions that can be beneficially treated with PK2 receptor agonist or PK2 receptor antagonist include non-24-hour sleep-wake syndrome, rapid time-zone change syndrome, work-shift syndrome, delayed phase sleep syndrome, advanced sleep phase syndrome, irregular sleep-wake pattern syndrome, syndrome associated with decreased amplitude. In addition, seasonal disorders such as seasonal affective disorder can be beneficially treated with PK2 receptor agonist or PK2 receptor antagonist.

The invention provides another for identifying a compound for modulating circadian rhythm. The method involves (a) contacting an isolated nucleic acid comprising a PK2 gene promoter operatively linked to a reporter nucleic acid with one or more candidate compounds under conditions wherein the reporter nucleic acid produces a predetermined signal in response to PK2 gene promoter activation; (b) identifying a compound that alters production of the signal; (c) providing the compound; and (d) determining the ability of the compound to modulate one or more indicia of circadian rhythm function, wherein a compound that modulates one or more indicia of circadian rhythm function is identified as a compound for modulating circadian rhythm.

The invention also provides compositions containing detectably labeled PK2 and an isolated mouse PK2 receptor.

Also provided by the invention is an isolated nucleic acid comprising a PK2 gene promoter operatively linked to a heterologous nucleotide sequence, which can be, for example, a reporter nucleotide sequence. In one embodiment, the invention provides a method for using the PK2 gene promoter for light-inducible expression of a nucleic acid molecule in an animal.

BRIEF DESCRIPTION OF THE DRAWINGS

FIG. 1a shows PK2 mRNA expression in coronal sections (20 μm) of the mouse brain. FIG. 1b shows temporal profiles of PK2 mRNA in the suprachiasmatic nucleus (SCN). FIG. 1c shows representative images of PK2 mRNA expression shown in FIG. 1b.

FIG. 2a shows the boundaries of E-boxes (E) and cAMP-responsive element (CRE) within the 5'-flanking region of the mouse PK2 gene. FIG. 2b shows transcriptional activation of luciferase reporter containing 2.8 kb (PK2.8-Luc) and 200 bp (PKO.2-Luc) of the 5'-flanking region of mouse PK2 gene. FIG. 2c shows transcriptional activation of SV40-driven luciferase reporter (pGL3-Promoter) containing 72 bp of all four E-boxes and their immediate flanking sequences linked together (PK4E-Luc). FIG. 2d shows inhibition of CLOCK:BMAL1-mediated transcription from PK2.8-Luc by mPers and mCrys. FIG. 2e shows the positive effect of PK2 receptor activation on CLOCK:BMAL1-mediated transcription of the PK2 gene.

FIG. 3a shows temporal profiles of PK2 mRNA in SCN of Clk/Clk mice. FIG. 3b shows the expression of PK2 mRNA in SCN of Cry/Cry mice at CT6 and CT18.

FIG. 4c shows a shift PK2 rhythm in SCN in response to light pulses. FIG. 4d shows quantification of phase shifts shown in FIG. 4c.

FIGS. 5a-e show autoradiographic images of PKR2 mRNA in lateral septum (LS), paraventricular thalamic (PVT) and hypothalamic nucleus (PVN), suprachiasmatic nucleus (SCN), paratenial nucleus (PT), paracentral nucleus (PC), lateral habenula (LHb), dorsal medial hypothalamic nucleus (DMH) and arcuate nucleus (Arc). FIGS. 5f-j show dark field microscopic images of PKR2 mRNA from the boxed regions in top panel (a-e). FIGS. 5k and 5l show microscope images of PK2. FIGS. 5m and 5n show PKR2 mRNA in SCN at high magnification.

FIG. 6a shows PKR2 mRNA expression in the paracentral nucleus (PC), paraventricular thalamic nuclei (PVT), paraventricular hypothalamic nuclei dorsal cap (PaDC), and suprachiasmatic nucleus (SCN). FIG. 6b shows PKR2 mRNA expression in the lateral habenula (LHb), lateral globus pallidus (LGP), amygdala (Amg), paraventricular thalamic nuclei (PVT), dorsal medial hypothalamic nucleus (DMH) and arcuate nucleus (Arc). FIGS. 6c, d, e and f depict dark field microscopic images of the PKR2 mRNA from the boxed regions in FIGS. 6a and b.

FIG. 7a shows experimental design. FIGS. 7b and c show PK2 mRNA expression in normal light-dark cycles.

FIGS. 9a and 9b show representative actograms of rats injected with PK2 (a) or saline (b) at CT14. FIG. 9c shows quantification of night and day locomotor activity following delivery of PK2 (n=7) or saline (n=6).

FIG. 10 shows a comparison of the amino acid sequences of human PK2s (SEQ ID NOS:5 and 6), mouse PK2s (SEQ ID NOS:7 and 8), human PK1 (SEQ ID NO:9), mouse PK1 (SEQ ID NO:10), frog Bv8 (SEQ ID NO:11), toad Bv8 (SEQ ID NO:12), and snake MIT1 (SEQ ID NO:13).

DETAILED DESCRIPTION OF THE INVENTION

Figure 1:
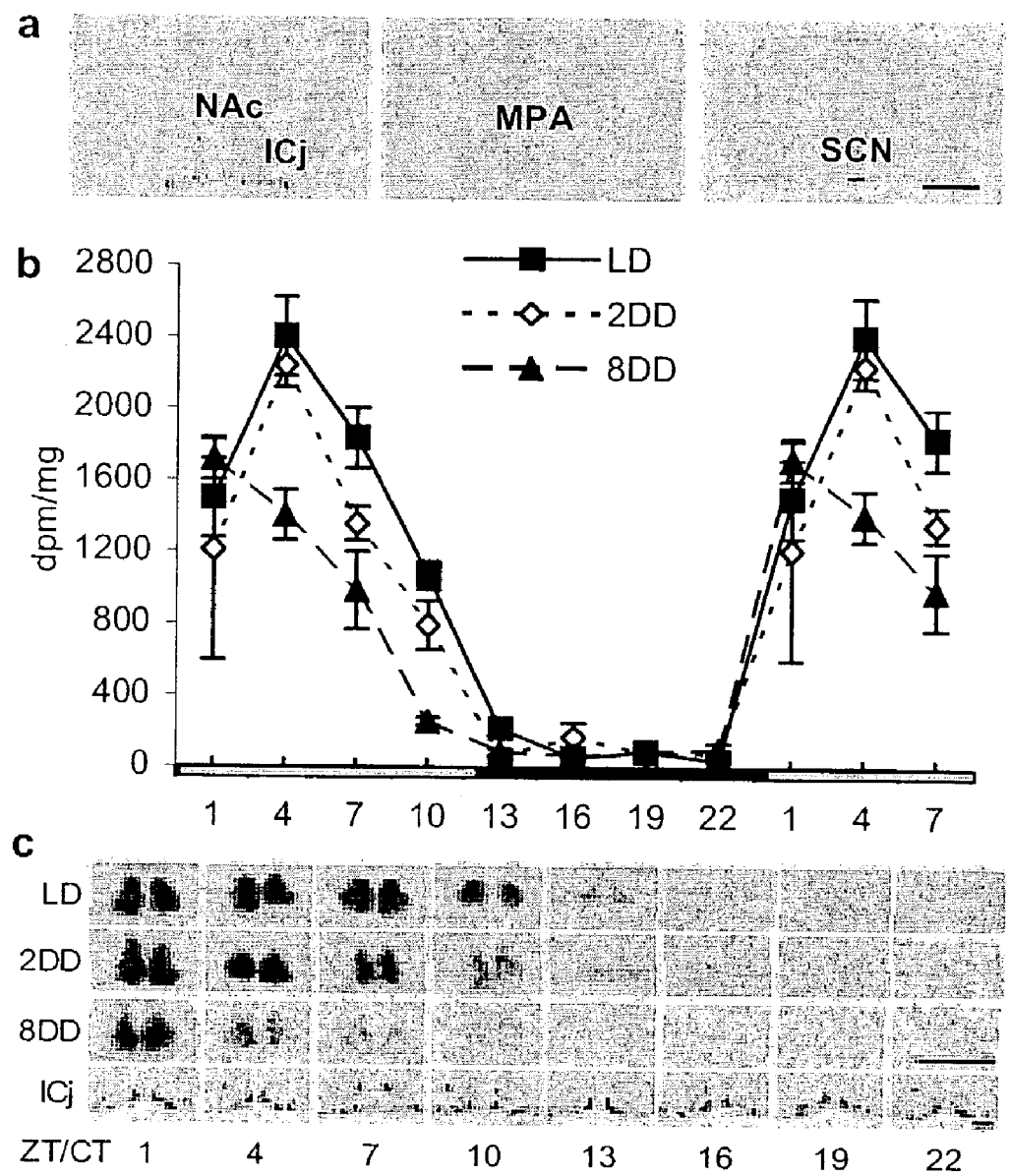
FIG. 1 shows rhythmic expression of PK2 mRNA in SCN.

The present invention relates to the determination that expression of the prokineticin 2 (PK2) gene in the suprachiasmatic nucleus (SCN) oscillates in a circadian fashion, and to the observation that PK2 receptor activation modulates circadian rhythm in rats.

Circadian rhythms optimize biological efficiency by coordinating appropriate timing of physiological, endocrine and behavioral processes. Circadian rhythms are thought to contain at least three elements: a) input pathways(s) that relay environmental information to a circadian pacemaker (clock) b) a circadian pacemaker that generates the oscillation and c) output pathway(s) through which the pacemaker regulates various output rhythms. In mammals, the master circadian pacemaker resides in the suprachiasmatic nuclei (SCN) of the anterior hypothalamus (Klein et al., *New York: Oxford Univ. Press.* pp. 467 (1991)). Environmental light-dark cycles are input signals that entrain, or synchronize, the SCN clock to the 24-hr day via retinal-hypothalamic projections (Moore, *Ann. Rev. Med.* 48:253-66 (1997)). Synchronization of the cell-autonomous circadian clocks within the SCN leads to coordinated outputs (signaling pathways) that mediate the circadian regulation of physiology and behavior.

As disclosed herein, prokineticin 2 (PK2) is a SCN output molecule that transmits circadian rhythm. This role for PK2 is supported by the observations that PK2 is expressed in an oscillatory manner in the SCN (see Example I); production and/or release of PK2 is regulated by core clock genes (see Example II and III); production or release of PK2 responds to light entrainment (see Example IV); PK2 receptor is expressed in the primary SCN output target areas (see Example V); administration of PK2 results in changes in circadian behavior (see Example VI); and PK2 rhythmic output in the SCN is regulated by light (see Example VIII).

In particular, the inventors have shown that expression of PK2 gene in the SCN oscillates in a circadian fashion under normal light/dark cycle as well as in constant darkness. The oscillation amplitude of PK2 mRNA in the SCN is very high, with peak levels (day time) and trough levels (night time) differing by at least 50-fold. This magnitude of PK2 oscillation in the SCN is higher than other known clock or clock-controlled genes, including mpers, mCrys, and Bmal (Cermakian et al., *EMBO J.* 20:3967-74 (2001); Albrecht et al., *Cell* 91:1055-64 (1997); Tei et al., *Nature* 389:512-16 (1997); Miyamoto and Sancar, *Proc. Natl. Acad. Sci. USA* 95:6097-102 (1998)); and Zylka et al., *Neuron* 20:1103-10 (1998)). The observed positive feedback of PK2 on its own transcription could contribute to the high oscillation magnitude of PK2 mRNA (see Example II). Both in vitro transcription assays and analyses of mutant mice deficient in Cryptochromes and Clock I (see Examples II and III, respectively) indicate that PK2 is a clock-controlled gene.

PK2 transcription is activated by CLOCK and BMAL1 heterodimers via E-box enhancers in the 5'-flanking region, and this transactivation is also inhibited by the members of the negative limb of the central clockwork, including mPER1, mPER2, mPER3, mCRY1, and mCRY2. The organization of E-box enhancers in 5'-flanking region and the oscillation profile of PK2 in the SCN are most similar to those of mperl (Albrecht et al., *Cell* 91:1055-64 (1997); and Tei et al., *Nature* 389:512-16 (1997)). Light pulse experiments show that PK2 rhythm in the SCN responds to light entrainment (see Example IV) and that abrupt shifts of light/dark cycles arid changes in photoperiod alter PK2 expression (see Examples VIII and IX). Like mPer1 and mPer2 (Albrecht et al., *Cell* 91:1055-64 (1997); Tei et al., *Nature* 389:512-16 (1997); and Zylka et al., *Neuron* 20:1103-10 (1998)), PK2 responds to light induction only during subjective night. Light pulses delivered during early or late night result in delay or advance of PK2 rhythm in SCN, respectively. These Light-induced changes in PK2 rhythm are consistent with the shifts of behavioral rhythm (Daan and Pittendrigh, *J. Comp. Physiol.* 106:253-266 (1976); and Roenneberg and Foster, *Photochem. Photobiol.* 66:549-561 (1997)).

PK2 administration to rats, as shown in Example VI, provides direct evidence that PK2 is an output molecule that transmits the locomotor activity rhythm of the SCN. Specifically, Example VI shows that ICV administration of PK2 during subjective night suppressed the high nocturnal wheel-running behavior. These behavioral studies are consistent with the distribution of PKR2 mRNA in major primary target areas of SCN output pathways (Klein et al., *New York: Oxford Univ. Press.* 467 pp. (1991); Moore, *Ann. Rev. Med.* 48:253-66 (1997); Sofroniew and Weindl, *Amer. J. Anat.* 153:391-429 (1978); Watts et al., *J. Comp. Neurol.* 258:204-29 (1987); Watts and Swanson, *J. Comp. Neurol.* 258:230-52 (1987); Leak and Moore, *J. Comp. Neurol.* 433:312-34 (2001); and Buijs, *Prog. Brain Res.* 111:229-40, (1996)).

PK2 is a polypeptide ligand for the G-protein coupled receptor, PKR2. Binding of PK2 to this receptor results in receptor activation, which induces a cascade of molecular events that culminate in alterations of cellular function. Such alterations in cellular function lead to cellular, physiological, endocrine, behavioral, and other responses that can be observed in an animal treated with PK2. Therefore, a PK2 receptor agonist or antagonist can be provided to an animal to alter a PK2-induced response, for example, to beneficially modulate circadian rhythm.

Based on this determination of an important pharmacological role of PK2 and PK2 receptor in control of circadian rhythm, the present invention provides methods of screening to identify compounds that modulate circadian rhythm, for example by modulating PK2 expression or PK2 receptor activity. Exemplary compounds that modulate PK2 receptor activity are PK2 receptor antagonist and agonists. Compounds identified using the methods of the invention can be used to modulate circadian rhythm for the treatment of circadian rhythm disorders.

The invention provides a method for identifying a compound for modulating circadian rhythm. The method involves (a) providing a compound that is a Prokineticin 2 (PK2) receptor antagonist or agonist; and (b) determining the ability of the compound to modulate one or more indicia of circadian rhythm function, wherein a compound that modulates one or more indicia of circadian rhythm function is identified as a compound for modulating circadian rhythm.

The methods of the invention also can be used to identify compounds useful for modulating biological rhythmicity having a period other than a 24 hour period. For example, activation of a PK2 receptor can modulate a biological rhythm having a periodicity of less than 24 hours (ultradian rhythm) or greater than 24 hours (infardian rhythm). Exemplary ultradian rhythms are daydreaming, urination, and hunger. Exemplary infardian rhythms include the frequency of receptivity of female animals to male animals for mating.

As used herein, the term "circadian rhythm" is intended to mean the regular variation in physiologic and behavioral parameters that occur over the course of about 24 hours.

As used herein, the term "modulating" when used in reference to circadian rhythm is intended to mean altering a physiological function, endocrine function or behavior that is regulated by the circadian timing system of an animal, or altering a cellular function that exhibits circadian rhythmicity. Exemplary physiological functions regulated by the circadian timing system of an animal include body temperature, autonomic regulation, metabolism, and sleep-wake cycles. Exemplary endocrine functions regulated by the circadian timing system of an animal include pineal melatonin secretion, ACTH-cortisol secretion, thyroid stimulating hormone secretion, growth hormone secretion, neuropeptide Y secretion, serotonin secretion, insulin-like growth factor type I secretion, adrenocorticotropic hormone secretion, prolactin secretion, gamma-aminobutyric acid secretion and catecholamine secretion. Exemplary behaviors regulated by the circadian timing system of an animal include movement (locomotor rhythm), mental alertness, memory, sensorimotor integration, and emotion. Exemplary cellular functions that exhibit circadian rhythmicity are neuron firing and transcriptional control of gene expression.

The methods of the invention for screening for a compound that modulates circadian rhythm involve providing a PK2 receptor antagonist or agonist. The PK2 receptor antagonist or agonist can be provided to a cell preparation, tissue, organ, organism or animal that has at least one observable index of circadian rhythm function and expresses a PK2 receptor. The ability of the PK2 receptor antagonist or agonist to modulate circadian rhythm can be tested in a variety of animal species that exhibit indicia of circadian rhythm function, as well as organs, tissues, and cells obtained from such animals, and cell preparations derived therefrom. The provided PK2 receptor antagonist or agonist can be a known PK2 receptor antagonist or agonist, such as PK2, PK1 or a PK2/PK1 chimera, or can be a compound identified as a PK2 receptor antagonist or agonist using in vitro screening methods described herein.

A variety of in vitro screening methods are useful for identifying a PK2 receptor antagonist or agonist to be provided in the methods of the invention for identifying a compound that modulates circadian rhythm. The ability of a compound to modulate PK2 receptor can be indicated, for example, by the ability of the compound to bind to and activate PK2 receptor, block agonist binding to PK2 receptor, promote a predetermined signal produced by a PK2 receptor, or reduce a predetermined signal produced by a PK2 receptor. Therefore, signaling and binding assays can be used to identify a PK2 receptor antagonist or agonist that is provided in the methods of the invention for identifying a compound that modulates circadian rhythm.

A signaling or binding assay used to identify a PK2 receptor antagonist or agonist can contain a PK2 receptor or a PK1 receptor. Because of the homology between PK2 and PK1 receptors, which have amino acid sequences that are about 85% identical, a PK2 receptor or PK1 receptor can be used in screening assays to identify a PK2 receptor agonist. Specifically, due to the homology between the PK1 receptor and PK2 receptor, a PK1 receptor agonist or antagonist is likely to also function as a PK2 receptor agonist or antagonist. Similarly, either PK1 or PK2 can function as an agonist in signaling and binding assay formats that employ a competitive agonist.

When a signaling assay is used to identify a PK2 receptor antagonist or agonist, the methods of the invention can involve contacting a PK1 receptor or PK2 receptor with one or more candidate compounds under conditions in which PK2 promotes a predetermined signal and identifying a compound that either decreases or increases the predetermined signal, respectively. When a binding assay is used to identify a PK2 receptor antagonist or agonist, the methods of the invention can involve contacting a PK1 receptor or PK2 receptor with one or more candidate compounds under conditions in which PK2 binds to the PK2 receptor and identifying a compound that either decreases binding of a PK2 receptor agonist to the PK1 receptor or PK2 receptor, or binds to and activates the PK1 receptor or PK2 receptor, respectively.

A PK2 receptor used in the screening methods of the invention can be, for example, a mouse or human PK2 receptor, including a recombinantly produced receptor or naturally occurring receptor present in a cell preparation. As used herein, the term "mouse PK2 receptor" is intended to mean a heptahelical membrane-spanning G-protein-coupled receptor comprising the amino acid sequence of mouse PK2 receptor, or a naturally-occurring or man-made minor modification thereof that binds to PK2 and signals through a G-protein coupled signal transduction pathway in response to PK2. A PK2 receptor also can bind to PK1 to induce PK2 receptor signaling. The invention provides a mouse PK2 receptor, which has the amino acid sequence referenced as SEQ ID NO:2, and is encoded by the nucleotide sequence referenced as SEQ ID NO:1. The invention also provides a screening composition containing a mouse PK2 receptor in the presence of PK1 or PK2.

Similarly, a PK1 receptor used in the screening methods of the invention can be, for example, a mouse or human PK1 receptor, including a recombinantly produced receptor or naturally occurring receptor present in a cell preparation. As used herein, the term "mouse PK1 receptor" is intended to mean a heptahelical membrane-spanning G-protein-coupled receptor comprising the amino acid sequence of mouse PK1 receptor, or a naturally-occurring or man-made minor modification thereof that binds to PK1 or PK2 and signals through a G-protein coupled signal transduction pathway in response to PK1 or PK2. An exemplary mouse PK1 receptor has the amino acid sequence referenced as SEQ ID NO:4, and is encoded by the nucleotide sequence referenced as SEQ ID NO:3.

A minor modification of the sequence referenced as SEQ ID NO:2 or 4 can have one or more additions, deletions, or substitutions of natural or non-natural amino acids relative to the native polypeptide sequence. Such a modification can be, for example, a conservative change, wherein a substituted amino acid has similar structural or chemical properties, for example, substitution of an apolar amino acid with another apolar amino acid (such as replacement of leucine with isoleucine). Such a modification can also be a nonconservative change, wherein a substituted amino acid has different but sufficiently similar structural or chemical properties so as to not adversely affect the desired biological activity, such as, replacement of an amino acid with an uncharged polar R group with an amino acid with an apolar R group (such as replacement of glycine with tryptophan). Further, a minor modification of the mouse PK2 receptor amino acid sequence referenced as SEQ ID NO:2 or 4 can be the substitution of an L-configuration amino acid with the corresponding D-configuration amino acid with a non-natural amino acid.

In addition, a minor modification of SEQ ID NO:2 or 4 can be a chemical or enzymatic modification to the polypeptide, such as replacement of hydrogen by an alkyl, acyl, or amino group; esterification of a carboxyl group with a suitable alkyl or aryl moiety; alkylation of a hydroxyl group to form an ether derivative; phosphorylation or dephosphorylation of a serine, threonine or tyrosine residue; or N- or O-linked glycosylation.

Those skilled in the art can determine whether minor modifications to the native mouse PK2 receptor sequence or PK1 receptor sequence are advantageous. Such modifications can be made, for example, to enhance the stability, bioavailability or bioactivity of the mouse PK2 receptor or PK1 receptor. A modified mouse PK2 receptor or PK1 receptor polypeptide can be prepared, for example, by recombinant methods, by synthetic methods, by post-synthesis chemical or enzymatic methods, or by a combination of these methods, and tested for ability to bind PK2 or PK1 or signal through a G-protein coupled signal transduction pathway.

Those skilled in the art also can determine regions in a mouse PK2 receptor or PK1 receptor amino acid sequence that can be modified without abolishing PK2 binding or signaling through a G-protein coupled signal transduction pathway. Structural and sequence information can be used to determine the amino acid residues important for PK2 receptor or PK1 receptor activity. For example, comparisons of amino acid sequences of PK2 receptor or PK1 receptor sequences from different species can provide guidance in determining amino acid residues that can be altered without abolishing activity.

Further, a large number of published GPCR structure-function studies have indicated regions of GPCRs involved in ligand interaction, G-protein coupling and in forming transmembrane regions, and indicate regions of GPCRs tolerant to modification (see, for example, Burstein et al., *J. Biol. Chem.*, 273(38):24322-7 (1998) and Burstein et al., *Biochemistry*, 37(12) 4052-8 (1998)). In addition, computer programs known in the art can be used to determine which amino acid residues of a GPCR, such as a mouse PK2 receptor, can be modified as described above without abolishing activity (see, for example, Eroshkin et al., *Comput. Appl. Biosci.* 9:491-497 (1993)).

As used herein, the term "PK2 receptor agonist" is intended to mean a compound that selectively promotes or enhances normal signal transduction through the PK2 receptor. A PK2 receptor agonist can act by any agonistic mechanism, such as by binding a PK2 receptor at the normal PK2 binding site, thereby promoting PK2 receptor signaling. A PK2 receptor agonist can also act, for example, by potentiating the binding activity of PK2 or signaling activity of PK2 receptor. A PK2 receptor agonist can also be a PK1 receptor agonist. As such, a PK1 receptor agonist can be tested for its ability to function as a PK2 receptor agonist using the screening methods described herein.

Specific examples of PK2 receptor agonists include human PK2 amino acid sequence SEQ ID NO:5 and 6; mouse PK2 amino acid sequences SEQ ID NOS:7 and 8, human PK1 amino acid sequence SEQ ID NO:9; mouse PK1 amino acid sequence SEQ ID NO:10; toad Bv8 amino acid sequence SEQ ID NO:12; frog Bv8 amino acid sequence SEQ ID NO:11, and snake MIT1 (SEQ ID NO:13). The major human PK2 amino acid sequence is that referenced as SEQ ID NO:5, while the PK2 amino acid sequence referenced as SEQ ID NO:6 is a tissue specific PK2 amino acid sequence expressed at least in testis. Similarly, the major mouse PK2 amino acid sequence is that referenced as SEQ ID NO:7, while the PK2 amino acid sequence referenced as SEQ ID NO:8 is a less commonly expressed PK2 amino acid sequence.

A PK2 receptor agonist can include a modification of PK2 or PK1 that is capable of binding to and activating a PK2 receptor. Such a modification can be, for example, one or more additions, deletions or substitutions compared with the recited amino acid sequence; one or more chemical or enzymatic modifications to the polypeptide; or substitution of one or more L-configuration amino acids with corresponding D-configuration amino acids.

A PK2 receptor agonist can include a chimeric polypeptide containing amino acid sequence encoded by both PK1 and PK2 genes. Exemplary PK2 receptor agonists include a chimeric polypeptide encoded by exons 1 and 2 of PK1 and exon 3 of PK2, referenced as SEQ ID NO:20, and a chimeric polypeptide encoded by exons 1 and 2 of PK2 and exon 3 of PK1, referenced as SEQ ID NO:21. PK2 receptor agonists also include other natural or synthetic cyclic peptides that activate signaling through the PK2 receptor at nanomolar concentrations.

Guidance in modifying amino acid residues of a PK2 or PK1 while retaining activity can be provided by comparison with corresponding PK2 or PK1 sequences from mammalian or non-mammalian vertebrate species. FIG. 10 provides a comparison of amino acid sequences of PK1 from mouse and human, PK2 from mouse and human, and an ortholog representing PK1 and PK2 genes from frog and toad (Bv8) and snake (MIT1). It is well known in the art that evolutionarily conserved amino acid residues and domains are more likely to be important for maintaining biological activity than less well-conserved residues and domains. Thus, it would be expected that substituting a residue that is highly conserved among mammalian prokineticins and vertebrate orthologs, such as the N-terminal sequence, or any of the 10 conserved cysteines, would likely be detrimental to activity, whereas substitution of less highly conserved residues, such as the C-terminal residues, is likely to be tolerated.

As used herein, the term "PK2 receptor antagonist" is intended to mean a compound that selectively inhibits or decreases normal signal transduction through the PK2 receptor. A PK2 receptor antagonist can act by any antagonistic mechanism, such as by binding a PK2 receptor or PK2, thereby inhibiting binding between PK2 and PK2 receptor. A PK2 receptor antagonist can also inhibit binding between a specific or non-specific PK2 receptor agonist and PK2 receptor. Such a specific or non-specific PK2 receptor agonist can be, for example, a drug that produces unwanted side effects by promoting signaling through the PK2 receptor. A PK2 receptor antagonist can also act, for example, by inhibiting the binding activity of PK2 or signaling activity of PK2 receptor. For example, a PK2 receptor antagonist can act by altering the state of phosphorylation or glycosylation of PK2 receptor. A PK2 receptor antagonist can also be an inverse agonist, which decreases PK2 receptor signaling from a baseline amount of constitutive PK2 receptor signaling activity.

As used herein, the term "predetermined signal" is intended to mean a readout, detectable by any analytical means, that is a qualitative or quantitative indication of activation of G-protein-dependent signal transduction through PK2 receptor. Assays used to determine such qualitative or quantitative activation of G-protein-dependent signal transduction through PK2 receptor, are referred to below as "signaling assays." G-proteins, or heterotrimeric GTP binding proteins, are signal transducing polypeptides having subunits designated $G\alpha$, $G\beta$ and $G\gamma$, that couple to seven-transmembrane cell surface receptors. G-proteins couple to such receptors to transduce a variety of extracellular stimuli, including light, neurotransmitters, hormones and odorants to various intracellular effector proteins. G-proteins are present in both eukaryotic and prokaryotic organisms, including mammals, other vertebrates, flies and yeast.

A signaling assay can be performed to determine whether a candidate compound is a PK2 receptor agonist or antagonist. In such an assay, a PK2 receptor is contacted with one or more candidate compounds under conditions wherein the PK2 receptor produces a predetermined signal in response to a PK2 agonist, such as PK2. In response to PK2 receptor activation, a predetermined signal can increase or a decrease from an unstimulated PK2 receptor baseline signal. A predetermined signal is an increasing signal, for example, when the amount of detected second messenger molecule is increased in response to PK2 receptor activation. A predetermined signal is a decreasing signal, for example, when the detected second messenger molecule is destroyed, for example, by hydrolysis, in response to PK2 receptor activation. A predetermined signal in response PK2 receptor activation can therefore be an increase in a predetermined signal that correlates with increased PK2 receptor activity, or a decrease in a predetermined signal that correlates with increased PK2 receptor activity. Accordingly, a PK2 receptor signaling assay of can be used to identify a PK2 receptor agonist that promotes production of a predetermined signal, whether the agonist promotes an increase in a predetermined signal that positively correlates with PK2 receptor activity, or a decrease in a predetermined signal that negatively correlates with PK2 receptor activity. Similarly, a signaling assay can be performed to determine whether a candidate compound is a PK2 receptor antagonist. In such a signaling assay, a PK2 receptor is contacted with one or more candidate compounds under conditions wherein the PK2 receptor produces a predetermined signal in response to a PK2 receptor agonist, such as PK2, and a compound is identified that reduces production of the predetermined signal.

Signaling through G proteins can lead to increased or decreased production or liberation of second messengers, including, for example, arachidonic acid, acetylcholine, diacylglycerol, cGMP, cAMP, inositol phosphate, such as inositol-1,4,5-trisphosphate, and ions, including $Ca^{++}$ ions; altered cell membrane potential; GTP hydrolysis; influx or efflux of amino acids; increased or decreased phosphorylation of intracellular proteins; or activation of transcription.

Various assays, including high throughput automated screening assays, to identify alterations in G-protein coupled signal transduction pathways are well known in the art. Various screening assay that measure $Ca^{++}$, cAMP, voltage changes and gene expression are reviewed, for example, in Gonzalez et al., *Curr. Opin. in Biotech.* 9:624-631 (1998); Jayawickreme et al., *Curr. Opin. Biotech.* 8:629-634 (1997); and Coward et al., *Anal. Biochem.* 270:2424-248 (1999). Yeast cell-based bioassays for high-throughput screening of drug targets for G-protein coupled receptors are described, for example, in Pausch, *Trends in Biotech.* 15:487-494 (1997). A variety of cell-based expression systems, including bacterial, yeast, baculovirus/insect systems and mammalian cells, useful for detecting G-protein coupled receptor agonists and antagonists are reviewed, for example, in Tate et al., *Trends in Biotech.* 14:426-430 (1996).

Assays to detect and measure G-protein-coupled signal transduction can involve first contacting a sample containing PK1 receptor or PK2 receptor, such as an isolated cell, membrane or artificial membrane, such as a liposome or micelle, with a detectable indicator. A detectable indicator can be any molecule that exhibits a detectable difference in a physical or chemical property in the presence of the substance being measured, such as a color change. Calcium indicators, pH indicators, and metal ion indicators, and assays for using these indicators to detect and measure selected signal transduction pathways are described, for example, in Haugland, *Molecular Probes Handbook of Fluorescent Probes and Research Chemicals*, Sets 20-23 and 25 (1992-94). For example, calcium indicators and their use are well known in the art, and include compounds like Fluo-3 AM, Fura-2, Indo-1, FURA RED, CALCIUM GREEN, CALCIUM ORANGE, CALCIUM CRIMSON, BTC, OREGON GREEN BAPTA, which are available from Molecular Probes, Inc., Eugene Oreg., and described, for example, in U.S. Pat. Nos. 5,453,517, 5,501,980 and 4,849,362.

Figure 12:
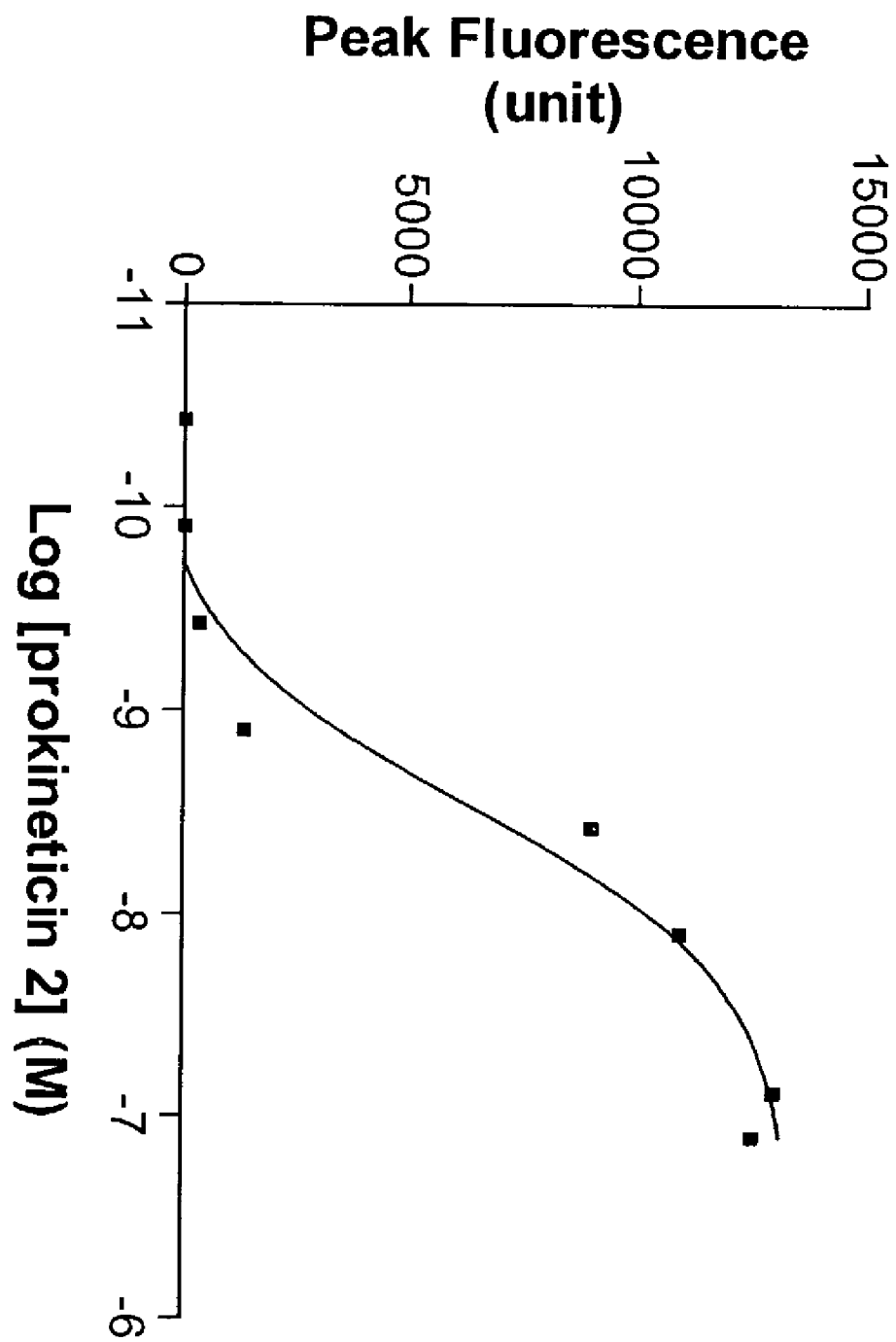
FIG. 12 shows calcium mobilization induced by PK2 binding to PK2 receptor.

Signaling through PK2 receptor and PK1 receptor promotes intracellular calcium ion mobilization, suggesting that these receptors normally couple to Gαq-containing G proteins. Therefore, signaling through the PK2 receptor or PK1 receptor can be detected by any assay known in the art that detects intracellular calcium ion mobilization, including that described in Example VII. A calcium ion mobilization assay can be performed in the presence or absence of a PK1 or PK2. FIG. 12 shows the results of an exemplary PK2 receptor activation assay in which the predetermined signal is calcium ion mobilization. FIG. 12 indicates that the $k_d$ for human PK2 activation of mouse PK2 receptor is 2.9 nM.

If desired, a predetermined signal other than $Ca^{2+}$ influx can be used as the readout for PK2 receptor activation. The specificity of a G-protein for cell-surface receptors is determined by the C-terminal five amino acids of the Gα subunit. The nucleotide sequences and signal transduction pathways of different classes and subclasses of Gα subunits in a variety of eukaryotic and prokaryotic organisms are well known in the art. Thus, any convenient G-protein mediated signal transduction pathway can be assayed by preparing a chimeric Gα containing the C-terminal residues of a Gα that couples to PK2 receptor or PK1 receptor, such as Gαq, with the remainder of the protein corresponding to a Gα that couples to the signal transduction pathway it is desired to assay. Methods of recombinantly expressing chimeric Gα proteins are known in the art and are described, for example, in Conklin et al., *Nature* 363:274-276 (1993), Komatsuzaki et al., *FEBS Letters* 406:165-170 (1995), and Saito et al., *Nature* 400:265-269 (1999). Additionally, chimeric Gα proteins can be prepared by synthetic methods.

Another type of signaling assay involves determining changes in gene expression in response to a PK2 receptor or PK1 receptor agonist or antagonist. A variety of signal transduction pathways contribute to the regulation of transcription in animal cells by stimulating the interaction of transcription factors with genetic sequences termed response elements in the promoter regions of responsive genes. Assays for determining the interaction of transcription factors with promoter regions to stimulate gene expression are well known to those skilled in the art and are commercially available. As described herein, the PK2 promoter is activated in response to PK2 receptor activation (see Example II). Therefore, a variety of promoters, including a PK2 promoter, can be employed in gene expression assays to detect PK2 receptor or PK1 receptor activity. Exemplary gene expression assays are those that involve transducing cells with a promoter-reporter nucleic acid construct such that a readily detectable protein such as β-lactamase, luciferase, green fluorescent protein or β-galactosidase will be expressed in response to contacting PK2 receptor or PK1 receptor with an agonist, such as PK2, PK1 or a PK2/PK1 chimera. Compounds identified in such gene expression assays can act either at the level of the cell surface, by modulating the activity of a PK2 receptor, the activity of a component of the PK2 receptor signal cascade or the activity of factors that modulate transcription of a PK2-controlled gene.

An assay to identify compounds that function as PK2 receptor agonists or antagonists is performed under conditions in which contacting the receptor with a known PK2 receptor agonist would produce a predetermined signal. If desired, the assay can be performed in the presence of a known PK2 receptor agonist, such as a PK2, including those referenced as SEQ ID NOS:5, 6, 7 and 8, or a PK1, including those referenced as SEQ ID NOS:9 and 10, or a PK2/PK1 chimera, including those referenced as SEQ ID NOS:20 and 21. The agonist concentration can be within 10-fold of the $EC_{50}$. Thus, an agonist that competes with PK2, PK1 or a PK2/PK1 chimera, for signaling through the PK2 receptor, or indirectly potentiates the signaling activity of PK2, can be readily identified. Similarly, an agonist that competes with PK2, PK1 or a PK2/PK1 chimera for signaling through the PK1 receptor can be readily identified.

Likewise, an antagonist that prevents PK2, PK1 or a PK2/PK1 chimera from binding the PK2 receptor, or indirectly decreases the signaling activity of PK2 receptor, also can be identified. Similarly, an antagonist that prevents PK2, PK1 or a PK2/PK1 chimera from binding the PK1 receptor, or indirectly decreases the signaling activity of PK1 receptor, also can be identified. The candidate compound can be tested at a range of concentrations to establish the concentration where half-maximal signaling occurs; such a concentration is generally similar to the dissociation constant (Kd) for PK2 receptor binding.

A binding assay can be performed to identify compounds that are PK2 receptor agonists or antagonists. In such an assay, a PK2 receptor or PK1 receptor can be contacted one or more candidate compounds under conditions in which PK2 binds to the selected receptor and a compound that binds to the selected receptor or that reduces binding of an agonist to selected receptor can be identified. Contemplated binding assays can involve detectably labeling a candidate compound, or competing an unlabeled candidate compound with a detectably labeled PK2 agonist, such as a PK2, PK1 or PK2/PK1 chimera. A detectable label can be, for example, a radioisotope, fluorochrome, ferromagnetic substance, or luminescent substance. Exemplary radiolabels useful for labeling compounds include $^{125}I$, $^{14}C$ and $^{3}H$. Methods of detectably labeling organic molecules, either by incorporating labeled amino acids into the compound during synthesis, or by derivatizing the compound after synthesis, are known in the art.

In order to determine whether a candidate compound decreases binding of detectably labeled PK2 to PK2 receptor, the amount of binding of a given amount of the detectably labeled PK2 is determined in the absence of the candidate compound. Generally the amount of detectably labeled PK2 will be less than its $K_d$, for example, 1/10 of its $K_d$. Under the same conditions, the amount of binding of the detectably labeled PK2, PK1 or PK2/PK1 chimera in the presence of the candidate compound is determined. A decrease in binding due to a candidate compound characterized as a PK2 receptor ligand is evidenced by at least 2-fold less, such as at least 10-fold to at least 100-fold less, such as at least 1000-fold less, binding of detectably labeled PK2, PK1 or PK2/PK1 chimera to PK2 receptor in the presence of the candidate compound than in the absence of the candidate compound.

Figure 11:
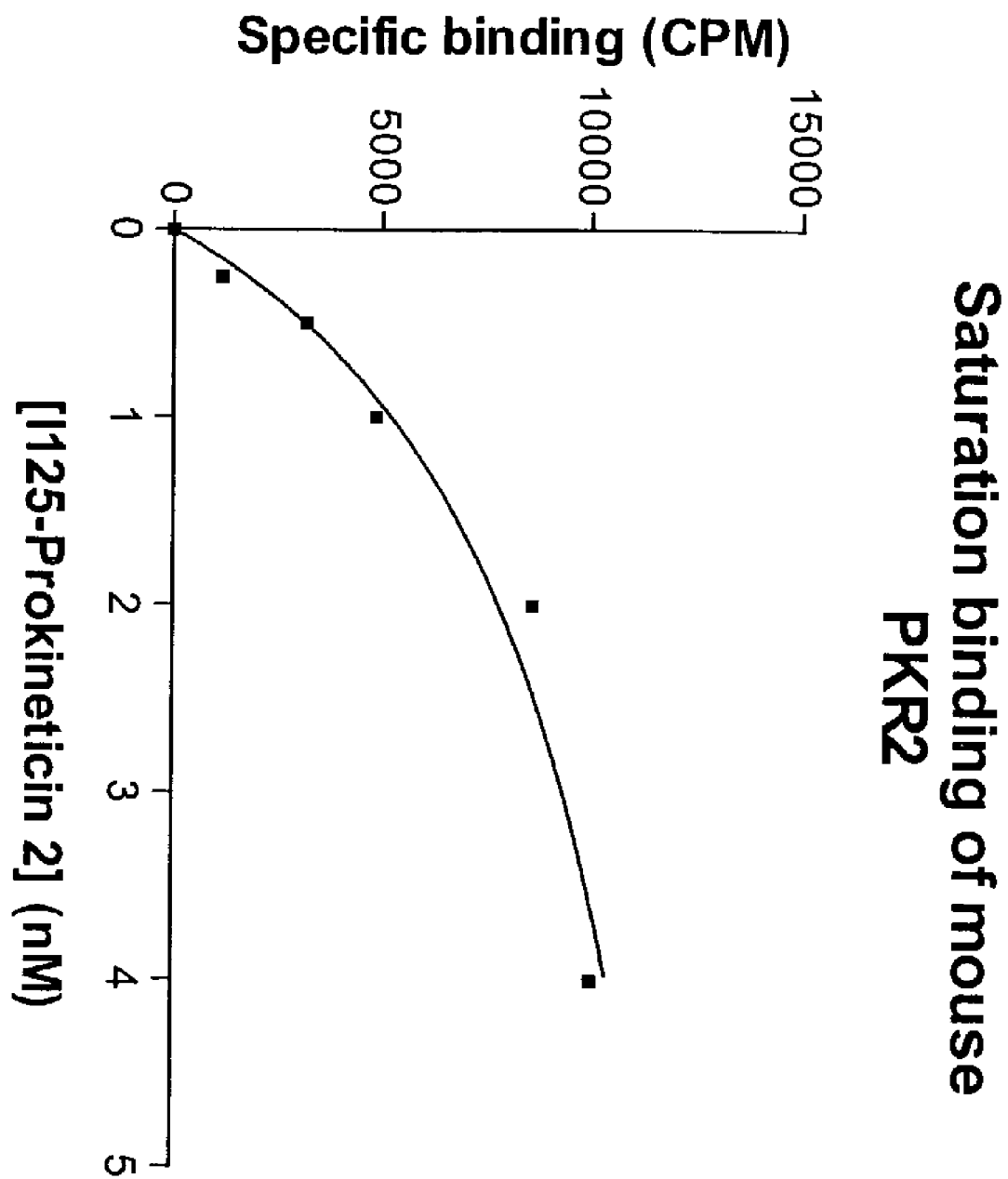
FIG. 11 shows binding of iodinated PK2 to PK2 receptor.

An exemplary assay for determining binding of detectably labeled PK2, PK1 or PK2/PK1 chimera to PK2 receptor or PK1 receptor is the radioligand filter binding assay described in Li et al. *Molecular Pharmacology* 59:692-698 (2001)). FIG. 11 shows the results of an exemplary PK2 receptor binding assay. FIG. 11 indicates that the Kd for $^{125}$I-human PK2 binding to mouse PK2 receptor is about 1 nM. A variety of other low- and high-throughput assays suitable for detecting selective binding interactions between a receptor and a ligand are known in the art. Such assays include, for example, fluorescence correlation spectroscopy (FCS) and scintillation proximity assays (SPA) reviewed in Major, *J. Receptor and Signal Transduction Res*. 15:595-607 (1995); and in Sterrer et al., *J. Receptor and Signal Transduction Res*. 17:511-520 (1997)). Binding assays can be performed in any suitable assay format including, for example, cell preparations such as whole cells or membranes that contain PK2 receptor or PK1 receptor, or substantially purified PK2 receptor polypeptide or PK1 receptor, either in solution or bound to a solid support.

A detectably labeled PK2, PK1 and PK2/PK1 chimera can be useful in many of the in vitro assays described above. PK2, PK1 and PK2/PK1 chimeras can be derivatized with, or conjugated to, a moiety that is detectable by any analytical means. Such detectably labeled molecules useful in the assays disclosed herein generally retain their ability to bind PK2 receptor or PK1 receptor at subnanomolar concentrations. For example, a detectable moiety can be a radioisotope, fluorochrome, ferromagnetic substance, or luminescent substance. In one embodiment, the detectably labeled PK2, PK1 or PK2/PK1 chimera is radiolabeled. Exemplary radiolabels useful for labeling peptides include $^{125}$I, $^{14}$C and $^3$H. Methods of detectably labeling peptides, either by incorporating labeled amino acids into the peptide during synthesis, or by derivatizing the peptide after synthesis, are known in the art. As described in Li et al. supra (2001), an exemplary detectably labeled PK2, PK1 or PK2/PK1 chimera is human PK2, radioiodinated at the core Tyr with $^{125}$I, which binds membranes of cells transfected with PK1 receptor with an apparent $K_d$ of 70 pM.

Assay methods for identifying compounds that selectively bind to or modulate signaling through a PK2 receptor generally involve comparison to a control. One type of a "control" is a preparation that is treated identically to the test preparation, except the control is not exposed to the candidate compound. Another type of "control" is a preparation that is similar to the test preparation, except that the control preparation does not express the receptor, or has been modified so as not to respond selectively to PK2 or PK1. In this situation, the response of the test preparation to a candidate compound is compared to the response (or lack of response) of the control preparation to the same compound under substantially the same reaction conditions.

A compound identified to be a PK2 receptor agonist or antagonist can be tested for its ability to modulate one or more indicia of circadian rhythm function, as described herein, below.

The invention provides a further method for identifying a compound useful for modulating circadian rhythm. The method involves (a) contacting an isolated nucleic acid comprising a PK2 gene promoter operatively linked to a reporter nucleic acid with one or more candidate compounds under conditions wherein the reporter nucleic acid produces a predetermined signal in response to PK2 gene promoter activation; (b) identifying a compound that alters production of the signal; (c) providing the compound, and (d) determining the ability of the compound to modulate one or more indicia of circadian rhythm function, wherein a compound that modulates one or more indicia of circadian rhythm function is identified as a compound useful for modulating circadian rhythm.

A compound identified to be a modulator of a PK2 gene promoter, such as a human PK2 gene promoter, is a potential therapeutically useful compound for modulating circadian rhythm. Example II demonstrates that transcription of mouse PK2 can be regulated by transcription factor binding to multiple E-box enhancers in the PK2 promoter. Specifically, CLOCK:BMAL1 heterodimer binding to a 2.8 kb region of the mouse PK2 promoter was demonstrated to increase PK2 transcription by 172-fold. Therefore, the level of PK2 in a cell can be modulated by activating or inhibiting PK2 gene expression from the PK2 gene promoter. For example, the activity of the PK2 promoter can be increased directly by adding a compound that binds to the PK2 promoter and induces PK2 gene expression. In addition, the activity of the PK2 promoter can be increased indirectly by increasing the amount of activating transcription factor, such as a CLOCK:BMAL1 heterodimer or their human orthologs, bound to the promoter, or the length of time that the activating transcription factor remains bound to the PK2 promoter, decreasing the amount of inhibiting transcription factor, such as mPER1, mPER2, mPER3, mCRY1 and mCRY1 or their human orthologs, or decreasing the length of time an inhibiting transcription factor remains bound to the PK2 promoter. Similarly, the activity of the PK2 promoter can be decreased directly by adding a compound that binds to the PK2 promoter and inhibits PK2 gene expression. PK2 promoter activity can be decreased indirectly for example, by decreasing the amount of activating transcription factor, decreasing the length of time an activating transcription factor remains bound to the PK2 promoter, increasing the amount of inhibiting transcription factor, or increasing the length of time an inhibiting transcription factor remains bound to the PK2 promoter.

Increasing or decreasing the amount of transcription factor, or homomultimeric or hetermultimeric transcription factor complex, can be achieved, for example, by increasing the expression or stability of a transcription factor(s) that enhances PK2 expression; by adding exogenous enhancing transcription factor(s) or mimetics thereof; decreasing the expression or stability of a transcription factor(s) that inhibits PK2 expression, and by adding exogenous inhibitory transcription factor(s) or mimetic thereof. Compounds capable of modulating the activity of a PK2 promoter can be identified, for example, by adding a candidate compound to a sample containing a PK2 promoter linked to a reporter nucleic acid, and measuring reporter nucleic acid expression. Compounds that regulate PK2 gene expression can be identified using such assays, and that modulate one or more indicia of circadian rhythm function, can be used for modulating circadian rhythm, for example, in an animal, including a human. This type of PK2 transcriptional activity assay also is useful for determining the activity of a PK2 receptor in response to a PK2 receptor antagonist or agonist, as described above.

Figure 13:
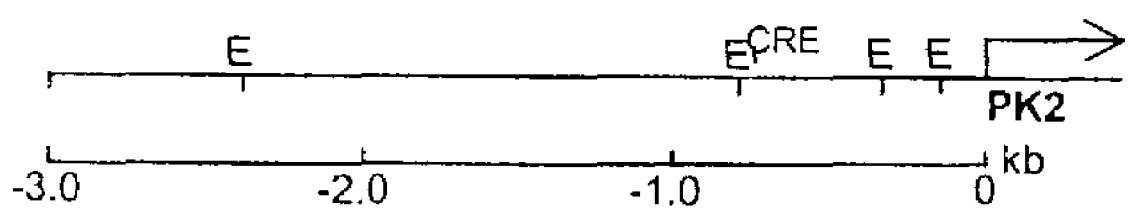
FIG. 13 shows the boundaries of E-boxes (E) and cAMP-responsive element (CRE) within the 5'-flanking region of the human PK2 gene.

As disclosed herein, the promoter region of the human PK2 gene has been identified to contain several E-box enhancers and a cyclic AMP response element (CRE) (see, for example, FIG. 13, which shows the boundaries of the E-boxes (E) and CRE and the sequence of the promoter region, respectively). The screening method can employ an exemplary PK2 gene promoter comprising a nucleic acid sequence referenced as SEQ ID NO:14 (human PK2 promoter), SEQ ID NO:15 (human 2.8 kb PK2 promoter), SEQ ID NO:16 (mouse PK2 promoter), SEQ ID NO:17 (mouse 2.8 kb promoter), or SEQ ID NO:18 (mouse 188 bp PK2 promoter). Each of these PK2 gene promoters can be modulated to induce or reduce the expression of a PK2 gene in the methods of the invention.

As shown in Example VIII, expression of PK2 in the SCN is light regulated. Thus, the human PK2 gene promoter can be used in a method for light regulated expression of a nucleic acid molecule in an animal. In one embodiment, the invention provides a method for light regulated expression of a nucleic acid molecule in an animal that involves introducing into the animal an isolated nucleic acid molecule comprising a PK2 gene promoter operatively linked to a heterologous nucleotide sequence. A variety of methods are known in the art for introducing a nucleic acid molecule into a cell. Such methods include microinjection, electroporation, lipofection, calcium-phosphate mediated transfection, DEAE-Dextran-mediated transfection, polybrene- or polylysine-mediated transfection, and conjugation to an antibody, gramacidin S, artificial viral envelopes or other intracellular carriers such as TAT. For example, cells can be transformed by microinjection as described in Cibelli et al., *Nat. Biotech.* 16:642-646 (1998) or Lamb and Gearhart, *Cur. Opin. Gen. Dev.* 5:342-348 (1995); by lipofection as described in Choi (U.S. Pat. No. 6,069,010) or Lamb and Gearhart, *Cur. Opin. Gen. Dev.* 5:342-348 (1995); by electroporation as described in *Current Protocols in Molecular Biology*, John Wiley and Sons, pp 9.16.4-9.16.11 (2000) or Cibelli et al., *Nat. Biotech.* 16:642-646 (1998); or by fusion with yeast spheroplasts Lamb and Gearhart, *Cur. Opin. Gen. Dev.* 5:342-348 (1995).

A nucleic acid containing a PK2 gene promoter operatively linked to a heterologous nucleotide sequence can be delivered into a cell, either in vivo or in vitro using suitable vectors well-known in the art. Suitable vectors for delivering a nucleic acid to a mammalian cell, include viral vectors such as retroviral vectors, adenovirus, adeno-associated virus, lentivirus, herpesvirus, as well as non-viral vectors such as plasmid vectors.

Viral based systems provide the advantage of being able to introduce relatively high levels of the heterologous nucleic acid into a variety of cells. Suitable viral vectors for introducing a nucleic acid containing a PK2 gene promoter into a mammalian cell are well known in the art. These viral vectors include, for example, Herpes simplex virus vectors (Geller et al., *Science*, 241:1667-1669 (1988)); vaccinia virus vectors (Piccini et al., *Meth. Enzymology*, 153:545-563 (1987)); cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., *Proc. Natl. Acad. Sci. USA*, 85:6460-6464 (1988); Blaese et al., *Science*, 270:475-479 (1995); Onodera et al., *J. Virol.*, 72:1769-1774 (1998)); adenovirus vectors (Berkner, *Biotechniques*, 6:616-626 (1988); Cotten et al., *Proc. Natl. Acad. Sci. USA*, 89:6094-6098 (1992); Graham et al., *Meth. Mol. Biol.*, 7:109-127 (1991); Li et al., *Human Gene Therapy*, 4:403-409 (1993); Zabner et al., *Nature Genetics*, 6:75-83 (1994)); adeno-associated virus vectors (Goldman et al., *Human Gene Therapy*, 10:2261-2268 (1997); Greelish et al., *Nature Med.*, 5:439-443 (1999); Wang et al., *Proc. Natl. Acad. Sci. USA*, 96:3906-3910 (1999); Snyder et al., *Nature Med.*, 5:64-70 (1999); Herzog et al., *Nature Med.*, 5:56-63 (1999)); retrovirus vectors (Donahue et al., *Nature Med.*, 4:181-186 (1998); Shackleford et al., *Proc. Natl. Acad. Sci. USA*, 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., *Nature Genetics*, 17:314-317 (1997)). It is understood that both permanent and transient expression can be useful in a method of the invention.

A human promoter is useful in the methods for identifying a compound for modulating circadian rhythm because a compound so identified likely will function as a compound active in a human cell. However, a mouse PK2 promoter can also be used in the methods for identifying a compound for modulating circadian rhythm. A compound identified to regulate mouse PK2 promoter can modulate both mouse and human PK2 promoters because these PK2 promoters are structurally and functionally similar, can modulate a mouse PK2 promoter, or can modulate a PK2 promoter of another species.

As disclosed herein in Example I, a heterocomplex of CLOCK and BMAL1 functions as a positive regulator of mouse PK2 gene expression. Because of the similarity between the mouse and human PK2 promoter regions, a CLOCK:BMAL1 heterocomplex can be used to positively regulate human PK2 gene expression by binding to a human PK2 promoter. Therefore, a method of the invention can involve activating a human PK2 gene promoter by contacting the promoter with a heterocomplex of CLOCK and BMAL1.

When a method of the invention is employed to identify a compound that negatively regulates PK2 gene expression, a candidate compound is provided to an activated PK2 promoter. A PK2 promoter can be activated, for example, by addition of a CLOCK:BMAL1 heterocomplex or other transcription factor that positively regulates PK2 gene transcription, or by adding PK2 or a PK2 receptor agonist, depending on the assay format used. Specifically, a CLOCK:BMAL heterocomplex or other transcription factor can be used in a variety of assay formats, from minimal component systems containing only a reporter nucleic acid operatively linked to the PK2 promoter to systems containing intact cells having PK2 receptors that can be activated in response to PK2. PK2 or another PK2 receptor agonist can be used in cell-based assay formats containing PK2 receptors that can be activated in response to PK2 and transmit a signal to the cell nucleus to regulate PK2 promoter activation.

When the method is employed to identify a compound that positively regulates PK2 gene expression, a candidate compound can be provided to an inactive PK2 promoter that has no bound transcription factors or has bound inhibitory transcription factor(s). The method can be used to identify a compound that binds directly to a PK2 promoter to increase promoter activity; a compound that binds to an inhibitory transcription factor to modulate its binding to a PK2 promoter, or a compound that functions by any other mechanism that results in an increase in PK2 gene expression.

A variety of nucleic acid molecules can be operatively linked to a PK2 gene promoter. As used herein, the term "operatively linked" is intended to mean that the nucleic acid molecule is positioned with respect to a promoter, such as a mouse or human PK2 promoter, in such a manner that the promoter will direct the transcription of RNA using the nucleic acid molecule as a template.

Methods for operatively linking a nucleic acid to a heterologous promoter are well known in the art and include, for example, cloning the nucleic acid into a vector containing the desired promoter, or appending the promoter to a nucleic acid sequence using PCR. A nucleic acid molecule operatively linked to a promoter of RNA transcription can be used to express reporter nucleic acid transcripts and polypeptides in a desired host cell or in vitro transcription-translation system. Exemplary reporter nucleic acids include luciferase, β-lactamase, β-glucuronidase, green fluorescent protein, blue fluorescent protein, chloramphenicol acetyltransferase and β-galactosidase.

As described above, circadian rhythm in an animal can be altered by modulating PK2 receptor activity by providing a PK2 receptor agonist or antagonist. A PK2 receptor agonist or antagonist can have a two-prong effect in altering a PK2-mediated biological response by modulating both PK2 receptor activity and PK2 gene expression, because as shown in Example II, PK2 receptor activation results in increased CLOCK:BMAL1-mediated PK2 gene expression. Specifically, CLOCK:BMAL1-mediated activation of PK2 gene transcription is regulated by PK2 receptor activity such that PK2 receptor activation increases transcription of the PK2 gene.

The level of PK2 expressed in cells of the SCN is under control of autoregulatory transcriptional and translational feedback loops that have both positive and negative elements. Positive transcriptional elements include two basic helix-loop-helix, PAS domain-containing transcription factors, CLOCK and BMAL1, which heterodimerize and drive the transcription of three Period genes (mPer1, mPer2, and mPer3) and two Cryptochrome genes (mCry1 and mCry2) by binding to their respective CACGTG E-box enhancers (Gekakis et al., *Science* 280:1564-69 (1998); Hogenesch et al., *Proc. Natl. Acad. Sci. USA* 95:5474-79 (1998)). The mPER and mCRY proteins act as negative components of the feedback loop, with mCRY proteins playing dominant inhibitory roles (Kume et al., *Cell* 98:193-205 (1999)). The amounts or activities of molecular components of these autoregulatory transcriptional and translational feedback loops can be altered to modulate circadian rhythm in an animal.

Methods for screening for a compound that modulates circadian rhythm, including a compound that is a PK2 receptor antagonist or agonist and a compound that modulates PK2 promoter activity, can involve contacting a PK2 receptor or PK2 promoter with one or more candidate compounds. A candidate compound can be a naturally occurring macromolecule, such as a peptide, nucleic acid, carbohydrate, lipid, or any combination thereof. A candidate compound also can be a partially or completely synthetic derivative, analog or mimetic of such a macromolecule, or a small organic or inorganic molecule prepared partly or completely by combinatorial chemistry methods.

A candidate compound further can be an antibody, including a monoclonal, humanized and chimeric antibodies, and functional fragments of an antibody includes chimeric, bifunctional, humanized and single chain antibodies (scFv), variable region fragments (Fv or Fd), Fab and F(ab)$_2$. An antibody can be naturally occurring or non-naturally occurring.

A candidate compound that is a nucleic acid can include, for example, an anti-sense nucleotide sequence, an RNA molecule, or an aptamer sequence. An anti-sense nucleotide sequence can bind to a nucleotide sequence within a cell and modulate the level of expression of a PK2 gene or PK2 receptor gene, or modulate expression of another gene that controls the expression of PK2 or PK2 receptor. Similarly, an RNA molecule, such as a catalytic ribozyme, can bind to and alter the expression of a PK2 gene, PK2 receptor gene, or other gene that controls the expression of PK2 or PK2 receptor. An aptamer is a nucleic acid sequence that has a three dimensional structure capable of binding to a molecular target, such as a PK2 or PK2 receptor (Jayasena, S. D. *Clinical Chemistry* 45:9, 1628-1650 (1999)). As such, an aptamer can serve as a PK2 receptor agonist or antagonist.

A candidate compound that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each $_3$' end (Elbashir et al., *Nature* 411:494-498 (2001); Bass, *Nature* 411:428-429 (2001); Zamore, *Nat. Struct. Biol.* 8:746-750 (2001)). dsRNAs of about 25-30 nucleotides have also been used successfully for RNAi (Karabinos et al., *Proc. Natl. Acad. Sci.* 98:7863-7868 (2001). dsRNA can be synthesized in vitro and introduced into a cell by methods known in the art.

A candidate compound can be a peptidomimetic of an amino acid sequence of a PK2 polypeptide, such as any of SEQ ID NOS:5-14. Methods of rationally designing peptidomimetics of peptides, including neuropeptides, are known in the art. For example, the rational design of three peptidomimetics based on the sulfated 8-mer peptide CCK26-33, and of two peptidomimetics based on the 11-mer peptide Substance P, and related peptidomimetic design principles, are described in Horwell, *Trends Biotechnol.* 13:132-134 (1995). If desired in a particular assay format, a candidate compound can be detectably labeled or attached to a solid support.

The methods of the invention for screening for a compound that modulates circadian rhythm function can involve testing candidate compounds. The number of different candidate compounds to screen in a particular assay can be determined by those skilled in the art, and can be 2 or more, such as 5, 10, 15, 20, 50 or 100 or more different compounds. For certain applications, such as when a library of random compounds is to be screened, and for automated procedures, it may be desirable to screen $10^3$ or more compounds, such as $10^5$ or more compounds, including $10^7$ or more compounds.

Compounds for screening can be contained within large libraries of compounds, such as when high-throughput in vitro screening formats are used. Methods for producing large libraries of chemical compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.* 2:422-428 (1998); Tietze et al., *Curr. Biol.*, 2:363-371 (1998); Sofia, *Mol. Divers.* 3:75-94 (1998); Eichler et al., *Med. Res. Rev.* 15:481-496 (1995); and the like. Libraries containing large numbers of natural and synthetic compounds also can be obtained from commercial sources.

Compounds can be screened individually or in pools of a few, tens or hundreds of compounds. Therefore, a library of compounds can be screened sequentially, in a multi-sample format, in which each sample receives one compound, or multiplexed format, in which each sample receives more than one compound.

For the in vitro screening methods, a PK2 receptor or PK2 promoter can be contained in a cell preparation. As used herein, the term "cell preparation" is intended to mean a sample containing an isolated cell, which can be a cell contained in an organ, tissue, or cell culture and which contains a naturally occurring PK2 receptor. A cell preparation can contain intact, broken, solubilized, homogenized, or fractionated cells in the presence of a wide variety of components, such as buffers, salts and detergents, so long as PK2 receptor is capable of binding to PK2 and becoming activated in response to PK2 binding. A cell preparation also can be a cell line that expresses PK2 receptor. A cell line that expresses PK2 receptor can be identified by methods known in the art, such as competitive binding assays. An exemplary cell line that expresses PK2 receptor is the melanoma cell line M2A7 (available from American Type Culture Collection as ATCC CRL-2500). Other cell lines that express PK2 receptor include M2 melanoma cells (Cunningham et al., Science 255; 325-327 (1992)) and RC-4B/C pituitary tumor cells (ATCC CRL-1903). A cell preparation also can include cells that recombinantly express PK2 receptor. A cell preparation can be obtained from a variety of animals, including, for example, humans, non-human primates, rats and mice. A human cell preparation, for example, is a sample containing an isolated human cell, which can be a cell contained in an organ, tissue, or cell culture and which contains a naturally occurring human PK2 receptor.

A cell preparation can be characterized as having circadian rhythmicity, although this feature is not required when the cell preparation is used in screening methods to determining if a compound is a PK2 receptor antagonist or agonist. As described in Li et al. Molecular Pharmacology 59:692-698 (2001)., human PK2 receptor is expressed in a variety of human tissues, including brain, heart, skeletal muscle, stomach and placenta. Therefore, any of these organs and other organs that express PK2 receptor can be a source for preparing a cell preparation for use in the screening methods of the invention.

A cell preparation having the characteristic of circadian rhythmicity can be advantageously used in in vitro assays to determine if a candidate compound or PK2 receptor agonist or antagonist modulates circadian rhythm function. Exemplary cells having circadian rhythmicity are SCN neurons, which retain a rhythmic firing pattern when dispersed in culture (Earnest et al. Science 283:693-695 (1999)).

A cell preparation also can include cells that recombinantly express PK2 receptor. Where it is desired to increase the PK2 receptor concentration, or to express PK2 receptor in host cells where it is not normally expressed, including mammalian, yeast and bacterial cells, the PK2 receptor can be recombinantly expressed. For example, a recombinantly expressed mouse or human PK2 receptor can be used in the methods of the invention.

Recombinant expression is advantageous in providing a higher level of expression of the polypeptide than is found endogenously, and also allows expression in cells or extracts in which the polypeptide is not normally found. A recombinant nucleic acid expression construct generally will contain a constitutive or inducible promoter of RNA transcription appropriate for the host cell or transcription-translation system, operatively linked to a nucleotide sequence that encodes the polypeptide of interest. The expression construct can be DNA or RNA, and optionally can be contained in a vector, such as a plasmid or viral vector. Based on knowledge of the nucleic acid sequence encoding PK2 receptor, one skilled in the art can recombinantly express desired levels of a biologically active PK2 receptor polypeptide using routine laboratory methods, described, for example, in standard molecular biology technical manuals, such as Sambrook et al., Molecular Cloning: A Laboratory Manual, Cold Spring Harbor Laboratory, New York (1992) and Ansubel et al., Current Protocols in Molecular Biology, John Wiley and Sons, Baltimore, Md. (1998).

Exemplary host cells that can be used to express recombinant PK2 receptor include isolated mammalian primary cells; established mammalian cell lines, such as COS, CHO, HeLa, NIH3T3, HEK 293-T and PC12; amphibian cells, such as Xenopus embryos and oocytes; and other vertebrate cells. Exemplary host cells also include insect cells (e.g. Drosophila), yeast cells (e.g. S. cerevisiae, S. pombe, or Pichia pastoris) and prokaryotic cells (e.g. E. coli), engineered to recombinantly express PK2 receptor. Additionally, recombinant PK2 receptor can be expressed in extracts that support transcription and translation, such as reticulocyte lysates and wheat germ extracts.

An appropriate assay for establishing that an isolated cell expresses PK2 receptor can be determined by those skilled in the art. Such an assay can involve, for example, analysis of expression of PK2 receptor nucleic acid or expression of PK2 receptor polypeptide by methods known in the art. Assays for determining expression of PK2 receptor mRNA include, for example, Northern blots, RT-PCR or in situ hybridization analysis. Such methods are described, for example, in standard molecular biology manuals such as Sambrook et al., supra, (1992) and Ansubel et al., supra, (1998). Assays for determining expression of PK2 receptor protein include, for example, immunoblot analysis, immunoprecipitation, immunofluorescence or immunohistochemistry, using antibodies specific for PK2 receptor.

A polypeptide of the invention, or one prepared for use in the methods of the invention, can be isolated from the cellular components with which they are normally associated using a variety of well-known methods, for example, precipitation, gel filtration, ion-exchange, reverse-phase and affinity chromatography, and the like. Other well known methods are described in Deutscher et al., Guide to Protein Purification: Methods in Enzymology Vol 182, Academic Press (1990). The methods and conditions for biochemical purification of a polypeptide can be selected by those skilled in the art, and purification monitored using a suitable immunological assay, functional assay or other biochemical assay.

The mouse PK2 receptor of the invention, as well as PK2, other PK2 receptors and candidate compounds used in the methods of the invention, can be recombinantly expressed, either transiently or stably, in a variety of host cells well known in the art (see, for example, Li et al., supra (2001)). Similarly, methods of recombinantly expressing chimeric Gα proteins, and their use in G-protein signaling assays, are known in the art and are described, for example, in , and Saito et al., Nature 400:265-269 (1999), and Coward et al., Anal. Biochem. 270:2424-248 (1999)). Such methods are applicable also to recombinantly producing a PK2 receptor agonist or antagonist that is a peptide or polypeptide.

Recombinant expression of polypeptides containing multiple cysteine residues often results in the incorrect formation of inter- and intra-molecular disulfide bonds, which leads to the production of inactive, aggregated bacterial proteins. As described in Li et al., supra (2001), these problems can be overcome using conditions that minimize protein aggregation during refolding of the expressed polypeptide. Exemplary conditions that minimize protein aggregation are described in the Example, and differ from conventional conditions for preparing recombinant protein by including one or more of the following refolding conditions: 1) keeping protein concentration low (e.g. about 100 µg/ml); 2) dialysing, rather than diluting, the peptides to remove denaturing agent; 3) omitting oxidants from buffers; 4) maintaining high concentrations of urea in all buffers; 5) maintaining high concentrations of glycerol (e.g. at least about 10%) in buffers; and 6) keeping peptides and buffers at low temperature (e.g. about 4° C.). Of these conditions, it is contemplated that low protein concentration (for example, less than about 250 µg/ml, for example less than 200 µg/ml, 150 µg/ml, 100 µg/ml, or 50 µg/ml) and high urea concentration (e.g. at least about 1.5M, such as about 2M, 4M, 6M, 8M or higher) are the most important factors in successful refolding of active prokineticins.

It is expected that the same or similar conditions as those described herein can be used to recombinantly express and refold other polypeptides containing multiple cysteines, including other molecules that bind to and activate the PK2 receptor, so as to isolate a biologically active polypeptide.

Polypeptides and peptides of the invention, or prepared for used in the methods of the invention, including fragments and polypeptides having modifications, also can be generated by chemical synthesis. A variety of chemistries and instrumentation, included automated systems, such as Applied Biosystems, Inc. Model 430A or 431A, are well-suited for preparing peptides and polypeptides.

Antibodies or antibody fragments that are PK2 receptor agonist or antagonists or candidate compounds can be prepared using a variety of methods, including well-known methods for generating polyclonal and monoclonal antibodies in mice, rats, sheep and rabbits (see, for example, Harlow and Lane, *Antibodies: A Laboratory Manual*, Cold Spring Harbor Laboratory Press (1988)). Methods for generating chimeric, humanized, CDRS grafted, and reshaped antibodies are also well known to those skilled in the art (Huse et al. *Science* 246:1275-1281 (1989); Winter and Harris, *Immunol. Today* 14:243-246 (1993); Ward et al. *Nature* 341:544-546 (1989); Harlow and Lane, supra (1988); Hilyard et al., *Protein Engineering: A practical approach* (IRL Press 1992); Borrabeck, *Antibody Engineering*, 2d ed. (Oxford University Press (1995)). Fully human antibodies can also be generated using phage libraries and can be obtained from transgenic mice.

Upon identifying a compound that is a PK2 receptor agonist or antagonist, for example, using the screening methods described herein, such a compound can be tested to determine its effect on circadian rhythm. The effect of a PK2 receptor antagonist or agonist on a circadian rhythm that is maintained in a cell preparation, tissue or organ, such as neuronal firing and gene transcription, is predictive of the effect of the antagonist or agonist on a circadian rhythm function in an animal. Therefore, an assay employing a cell preparation, tissue or organ that maintains one or more indices of circadian rhythm function can be useful for assessing the effect of a PR2 antagonist or agonist on circadian rhythm function in an animal.

Such in vitro functional screening provides a relatively inexpensive alternative to animal screening that can be used to select potent candidate therapeutic molecules. In vitro functional screening for the ability of a PK2 receptor agonist or antagonist to modulate circadian rhythmicity can be performed using a variety of cell types that display an index of circadian rhythmicity and express PK2 receptor. Several cell types maintain circadian rhythm function outside of the organism from which they are isolated. For example, within the mammalian hypothalamus, the suprachiasmatic nucleus (SCN) contains a circadian clock for timing of diverse neuronal, endocrine and behavioral rhythms. By culturing cells from rat SCN on fixed microelectrode arrays, it has been shown that individual SCN neurons maintain spontaneous action potentials consistent with circadian rhythms for weeks (Welsh et al. Neuron 14:697-706 (1995). As shown herein, in Example V, PK2 receptor is highly expressed in mouse SCN. Therefore, cells from the SCN can be exemplary cells having an observable index of circadian rhythm function that express a PK2 receptor and can be used in the screening methods of the invention. The activity of isolated neurons, such as those from the SCN, can be measured using a variety of well-known methods, such as those described in Welsh, supra (1995). Cyclical change in neuron firing consistent with circadian rhythm is an example of an index of circadian rhythm that can be evaluated in the methods of the invention.

Another example of a cell that maintains circadian rhythm function outside of the organism from which it is isolated is a liver cell in which the circadian rhythm of the activity of metabolism enzymes is maintained. As described below, PK2 receptor is expressed in liver. Therefore, cells from the liver can be exemplary cells having an observable index of circadian rhythm function that express a PK2 receptor and can be used in the screening methods of the invention. The levels of enzyme activities, for example, the levels of metabolic enzymes and signal transduction enzymes can be measured using well-known methods. For example, the production or destruction of an enzyme substrate can be measured using a variety of analytical methods. Those skilled in the art will be able to select an appropriate method for measuring the activity of a particular enzyme. Cyclical change in the activity of cellular enzymes cellular consistent with circadian rhythm is an example of an index of circadian rhythm that can be evaluated in the methods of the invention.

Circadian rhythmicity also has been observed in cultured tissues explanted from peripheral organs (Yamazaki et al. *Science* 288:682-685 (2000)) and immortalized peripheral cells (Balsalobre et al. *Cell* 93:929-937 (1998) and Akashi et al. *Genes Dev.* 14:645-649 (2000)). As shown in Li et al, supra, 2001, PK2 receptor is expressed in several peripheral organs, including heart, testis, kidney, appendix, ovary, liver, and others. Those skilled in the art can obtain a variety of cell preparations, tissues or organs that express PK2 receptor, and determine whether circadian rhythmicity of a cell function, such as neuron firing, is maintained in a selected cell preparation, tissue or organ. Those skilled in the art will recognize that a variety of cell functions in addition to neuron firing can be maintained in a cell preparation, tissue or organ separated from an animal.

Gene transcription that is modulated by circadian rhythm is another example of an index of circadian rhythm that can be evaluated in the methods of the invention. The transcription of a variety of genes is regulated by circadian rhythm. Exemplary genes that are regulated by circadian rhythm include both genes whose products regulate the circadian clock (clock genes) and genes whose products mediate an animal's responses, such as physiological, endocrine, cellular and behavioral functions. Genes that are regulated by circadian rhythm vary among different animal species, although some clock genes are highly conserved among species. Examples of genes regulated by circadian rhythm include period-1, period-2, period-3, timeless, clock, cycle, double-time, cryptochrome-1, cryptochrome-2, PK2 and c-fos. For example, the c-fos gene has been shown to be regulated in the neural cells of rats after being exposed to a light source during the night to simulate an active day period (Kornhauser et al.

*Behav Genet.* May;26(3):221-40 (1996). Constant exposure to the light source resulted in a dramatically and rapidly increased amount of c-fos mRNA in the rat SCN. Those skilled in the art will be able to identify a gene that is regulated by circadian rhythm in an animal, and will be able to determine if such regulation is maintained in a cell preparation, tissue or organ. A variety of well-known methods can be used by those skilled in the art to monitor expression levels of genes during the circadian cycle in the presence or absence of a compound, such as a PK2 receptor agonist or antagonist.

A cellular index of circadian rhythm function can generally be determined by measuring a cellular activity specific for the cell type under study. For example, gene expression can be measured by well-known biochemical methods of detecting mRNA and polypeptide corresponding to a gene that is expressed in a circadian rhythm. Exemplary techniques include hybridization and PCR-based detection of mRNA and immunodetection of polypeptides, such as Western blotting and immunocytochemical methods.

A PK2 receptor antagonist or agonist, or PK2 promoter modulatory compound, also can be administered to an animal to determine if the compound modulates circadian rhythm. As used herein, the term "animal having an observable circadian rhythm function," is intended to mean a human, veterinary animal or laboratory animal, including invertebrates, such as snails (for example, *Bulla gouldiana*); flies, such as the melon fly and fruit fly; reptiles, such as iguanas; fish, such as zebrafish; mammals, such as rodents, including, for example, rats, mice, hamsters and degus, rabbits, cats and non-human primates that exhibit or can be induced to exhibit, one or more indicia of circadian rhythm function. As described herein, for diurnal animals, a PK2 antagonist can beneficially promote sleep while a PK2 agonist can beneficially promote day-time associated behavior, such as alertness. Conversely, for nocturnal animals, a PK2 antagonist can beneficially promote day-time associated behavior, such as alertness, while a PK2 agonist can beneficially promote sleep.

As used herein, the term "index of circadian rhythm function," or in the plural, the term "indicia of circadian rhythm function," is intended to mean an observable sign or indication of a physiological function, endocrine function, behavior or cellular function that is cyclical over the course of about 24 hours. Exemplary indicia of circadian rhythm function include cyclical changes in physiological functions, such as body temperature, autonomic regulation, metabolism, and sleep-wake cycles; cyclical changes in endocrine functions, such as secretion of hormones, including pineal melatonin secretion, ACTH-cortisol secretion, thyroid stimulating hormone secretion, and neuropeptide Y, serotonin secretion, and catecholamine secretion; and cyclical changes in behavior, such as movement (locomotor rhythm), mental alertness, memory, sensorimotor integration, and emotion, or cyclical changes in a cellular function, such as neuron firing or transcriptional control of gene expression.

Disorders of circadian rhythm function are characterized by alterations in physiological, endocrine and cellular functions and behavior. Indicia of abnormal circadian rhythm function include, for example, excessive day-time sleepiness, night-time arousals, and early awakening. In humans, clinically recognized circadian rhythm function disorders include Time-Zone Change (Jet Lag) Syndrome, Shift Work Sleep Disorder, Irregular Sleep-Wake Pattern, Delayed Sleep Phase Syndrome, Advanced Sleep Phase Syndrome, Non-24-Hour Sleep-Wake Disorder and the like.

As described in Example V, administration of PK2 during subjective night suppresses nocturnal behavior and produces daytime-associated behavior in rats. Accordingly, for nocturnal animals, a PK2 receptor agonist, or increase in PK2 gene expression, can be used to alter circadian rhythm by producing physiological, behavioral, or endocrine functions associated with subjective day-time. Conversely, a PK2 receptor antagonist, or decrease in PK2 gene expression, can be used to alter circadian rhythm by producing physiological, behavioral, or endocrine functions associated with subjective night-time. For diurnal animals, an opposite treatment strategy can be used, such that by providing a PK2 receptor agonist or by increasing PK2 gene expression, a diurnal animal can be beneficially treated to alter circadian rhythm by producing physiological, behavioral, or endocrine functions associated with subjective day-time, for example, for conditions associated with increased or excessive sleep, such as narcolepsy, states of diminished vigilence and the like. Conversely, a diurnal animal can be beneficially treated by decreasing the level of PK2 receptor activity by providing a PK2 receptor antagonist, or decreasing PK2 gene expression, to alter circadian rhythm by producing physiological, behavioral, or endocrine functions associated with subjective night-time, for example to treat conditions associated with reduced sleep, such as jet lag, shift worker syndrome and the like.

An animal can be evaluated for a variety of behaviors, as well as physiological and endocrine indices of circadian rhythm function. The method used for evaluating an animal will vary depending on the particular animal, for example, whether the animal is diurnal or nocturnal, and index evaluated. Behavioral indicia of circadian rhythm include a variety of activities, which can be activities that normally occur during the day or activities that normally occur during the night. Such activities vary considerably among animal species. For example, diurnal animals normally display sleep during the night and display motor activity during the day while nocturnal animals display sleep during the day and display motor activities during the night. A variety of daytime and nighttime activities of humans and other animals are well known and can be evaluated, for example, by viewing activity or behavior by eye, by imaging device, camera, video camera, tracking device, and the like, or by self-reporting of an activity or behavior, at one or more particular times. For example, described herein is the use of wheel-running as a behavioral index of circadian rhythm function of rats. Other types of spontaneous locomotor stereotypic activity, such as exploratory activity, can be assessed. Exemplary parameters that can be measured time engaged in locomotor activity, time engaged in resting or sleeping, distance traveled, number of footsteps and vertical counts (rearing).

For example, methods for evaluating an indicia of circadian rhythm function can involve determining the presence of increased or decreased sleepiness or alertness compared to normal. A "normal" amount of sleepiness or alertness is intended to mean an amount or quality of sleep observed or expected to be observed in an animal free from any circadian rhythm disorder. An animal having normal circadian rhythm can have, for example, an expected number of hours of sleep per 24 hour period, an expected amount of REM sleep, an expected number of waking episodes, an expected number of daytime naps, and the like, that will be dependent on the animal species and characteristics of an individual, such as age, physical condition, prior injury or disease, medication and the like.

Physiological indicia of circadian rhythm function can generally be determined by physical examination of the individual, for example using an instrument or measuring device, such as measuring body temperature using a thermometer at a particular time of day. Other examples include using electrodes to measure brain waves to assess sleep at a particular time of day and using a movement or heart rate monitor to assess physical activity of animals at a particular time of day. The time of day selected for measurement can depend on the particular animal species. For example, diurnal and nocturnal animals will have cyclic changes in physiological indicia of circadian rhythm function that correspond with their normal waking and sleeping cycles.

Endocrine indicia of circadian rhythm function can generally be determined using a biochemical test, such as measuring the amount of a molecule, such as a hormone, contained in an individual's bodily fluid at a particular time of day. For example, the adrenal glands produce molecules, such as cortisol, in a circadian rhythm. Normally, cortisol output is highest in the morning, approximately mid-value throughout the day, and then drops to a nearly negligible level during the night. A variety of other molecules are known to be produced in a circadian rhythm, with peak and through levels occurring at particular times within the 24-hour day depending on the particular molecule. As an indicia of circadian rhythm function, the level of a molecule that is produced in the body in a circadian rhythm can be determined and compared to a known standard level of that molecule expected to be present in a bodily fluid at a particular time of day. In addition, the level of such a molecule can be measured at intervals or continuously over a period of time sufficient to assess whether the level of the molecule is modulated in a circadian rhythm. Exemplary bodily fluids that can be collected and tested for a level of a particular molecule include blood, urine and saliva.

An index of circadian rhythm function also can be observed by viewing the output of a variety of attachable or implantable devices designed to measure physiological, behavioral, or endocrine functions. An exemplary implantable device is an electrode useful for measuring neurological activity in laboratory animals (for example, to determine the light response of the SCN). An exemplary attachable device is a surface electromyography instrument useful for measuring electrical activity of individual muscles or muscle groups (for example, to determine the sleep or wake state of an individual). Signals from such devices can be amplified, and analyzed by a computer. Indicia of circadian rhythm can be determined qualitatively or quantitatively and animals can generally be tested prior to and after treatment with a PK2 receptor agonist or antagonist, compound that modulates PK2 promoter activity or carrier.

In evaluating whether a PK2 receptor antagonist or agonist, or PK2 promoter activity modulator modulates circadian rhythm, a difference in a value of an index of circadian rhythm function before and after treatment with a compound can be determined. The amount of a PK2 receptor antagonist or agonist, or PK2 promoter activity modulator effective to modulate circadian rhythm is an amount effective to modulate the determined index of circadian rhythm function by at least 10%. For example, the determined index of circadian rhythm function can be increased or reduced by at least 20%, at least 50%, such as at least 80%, in at least some treated animals.

Methods for evaluating circadian rhythm in an animal are useful for both diagnosing a variety of circadian rhythm disorders to determine if an individual is a candidate for treatment with a PK2 receptor antagonist or agonist, as well as to evaluate an individual's response to administration of a PK2 receptor antagonist or agonist or PK2 promoter modulatory compound.

Methods for diagnosing circadian rhythm disorders are well known to those skilled in the art. Circadian rhythm disorders are described, for example, in *The Merck Manual of Diagnosis and Therapy*, 17$^{th}$ edition, Beers and Berkow (Eds.), Merck & Co. (1999). Circadian rhythm disorders that can be treated by a PK2 receptor antagonist or agonist, or PK2 promoter modulatory compound, include primary (idiopathic) or secondary (symptomatic, related to known disorders) or drug-induced circadian rhythm disorders, which can be hereditary or sporadic. In particular, circadian rhythm sleep disorders are disorders related to the timing of sleep within the 24-hour day. Some of these disorders are influenced by the timing of the sleep period that is under the individual's control (for example, shift work or time zone change). Others are disorders of neurological mechanisms (for example, irregular sleep-wake pattern and advanced sleep phase syndrome). Those skilled in the art will be able to identify individuals having circadian rhythm function disorders that could benefit from treatment with a PK2 receptor antagonist or agonist, including those having circadian rhythm sleep disorders that could benefit from treatment with either a PK2 receptor antagonist that promotes alertness, or a PK2 receptor agonist that promotes sleep.

As described above, variety of circadian rhythm function disorders can lead to reduced quality or quantity of sleep in an individual. Human circadian rhythm sleep disorders, such as non-24-hour sleep-wake syndrome, rapid time-zone change syndrome, work-shift syndrome, delayed phase sleep syndrome, advanced sleep phase syndrome, irregular sleep-wake pattern syndrome and syndrome associated with decreased amplitude, are characterized by abnormal sleeping and waking patterns, and can lead to the need for either increased alertness or increased sleep. In addition, medical and psychiatric conditions, such as chronic pain and depression, can affect circadian rhythm and cause reduced quality or quantity of sleep. In addition, because PK2 expression in the SCN can encode day length information, as shown in Example XI, modulation of PK2 receptor activity can be useful for altering seasonal rhythm regulation to treat disorders such as seasonal affective disorder. Further, medications used for treating a variety of conditions can effect circadian rhythm and cause reduced quality or quantity of sleep. A PK2 receptor antagonist or agonist, or PK2 promoter modulatory compound, identified by the methods of the invention as a compound that modulate. circadian rhythm can be used to treat such disorders in animals, in particular humans.

A PK2 receptor agonist or PK2 promoter modulatory compound that increases PK2 gene expression can be used to modulate the circadian rhythm of an animal such that the animal experiences increased alertness or reduced sleep. An animal or individual to be treated with a PK2 receptor agonist, including PK2, can be one that would benefit physically or psychologically from increased alertness. For example, increased alertness may be desired in an individual having sleepiness, a tendency to fall asleep, or having a sense of excessively deep sleep. A need for alertness can arise in an individual having a life-style induced circadian rhythm disorder, such as a condition caused by irregular work hours or shift work. An individual may desire increased alertness to enhance performance in mental or physical activities, such as long distance driving, shift work and study. A need for alertness can also be caused by a physiologically based circadian rhythm disorder that causes excessive daytime sleepiness, as well as adverse drug reactions. The compositions identified using the methods of the invention can thus be used to ameliorate the symptoms of such disorders and conditions.

A PK2 receptor antagonist or PK2 promoter modulatory compound that decreases PK2 gene expression can be used to modulate the circadian rhythm of an animal such that the animal experiences increased sleep or reduced alertness.

Therefore, an animal or individual to be treated with a PK2 receptor antagonist can be one that could benefit physically or psychologically from increased quality or quantity of sleep. For example, a animal or individual having reduced or insufficient quality or quantity of sleep, such as reduced ability to fall asleep or stay asleep, having the tendency to awaken earlier than desired in the morning or having a sense of light or unrefreshing sleep could benefit physically or psychologically from increased quality or quantity of sleep. The compositions identified using the methods of the invention can thus be used to ameliorate the symptoms of such disorders and conditions.

Those skilled in the art can determine other conditions for which it is appropriate to administer a PR2 receptor antagonist or antagonist identified by the methods of the invention to modulate circadian rhythm, and can monitor the safety and efficacy of the therapy.

Compounds such as PK2 receptor antagonists and agonists and PK2 promoter modulatory compounds can be evaluated for their ability to modulate circadian rhythm by administering to an animal. Such compounds can be potential therapeutic compounds that can be administered to individuals, such as those with conditions associated with abnormal circadian rhythm. Therefore, the methods of the invention can involve administering a pharmaceutical composition containing a PR2 receptor agonist or antagonist or other compound to an animal, including a veterinary animal, research animal or human. For determining if a compound modulates an index of circadian rhythm, the methods of the invention can be practiced using a variety of animals that have a detectable index of circadian rhythm function. Exemplary animals and indices of circadian rhythm are described above. For preclinical studies, the methods of the invention can be practiced with animals that serve as credible models of human disease, such as non-human primates, pigs, dogs, cats, hamsters and rodents (for example rats, mice and guinea pigs). Those skilled in the art understand which animals serve as appropriate models for a human disease of interest.

The identified compounds can be formulated and administered in a manner and in an amount appropriate for the condition to be treated; the weight, gender, age and health of the individual; the biochemical nature, bioactivity, bioavailability and side effects of the particular compound; and in a manner compatible with concurrent treatment regimens. An appropriate amount and formulation for a particular therapeutic application in humans can be extrapolated based on the activity of the compound in the in vitro binding and signaling assays described herein, or from recognized animal models of the particular disorder.

The total amount of a compound, including a therapeutic compound, can be administered as a single dose or by infusion over a relatively short period of time, or can be administered in multiple doses administered over a more prolonged period of time. Additionally, the compound can be administered in a slow-release matrix, which can be implanted for systemic delivery at or near the site of the target tissue. Contemplated matrices useful for controlled release of compounds, including therapeutic compounds, are well known in the art, and include materials such as DepoFoam™, biopolymers, micropumps, and the like.

Compounds, including therapeutic compounds, can be administered to a mammal by routes known in the art including, for example, intravenously, intramuscularly, subcutaneously, intraorbitally, intracapsularly, intraperitoneally, intracisternally, intra-articularly, intracerebrally, orally, intravaginally, rectally, topically, intranasally, or transdermally. Preferred routes for human administration are oral and intravenous administration, with oral routes particularly preferred.

Generally, compounds, including therapeutic compounds, are administered to an animal as a pharmaceutical composition comprising the compound and a pharmaceutically acceptable carrier. The choice of pharmaceutically acceptable carrier depends on the route of administration of the compound and on its particular physical and chemical characteristics. Pharmaceutically acceptable carriers are well known in the art and include sterile aqueous solvents such as physiologically buffered saline, and other solvents or vehicles such as glycols, glycerol, oils such as olive oil and injectable organic esters. A pharmaceutically acceptable carrier can further contain physiologically acceptable compounds that stabilize the compound, increase its solubility, or increase its absorption. Such physiologically acceptable compounds include carbohydrates such as glucose, sucrose or detrains; antioxidants, such as ascorbic acid or glutathione; chelating agents; and low molecular weight proteins.

For applications that require the compounds and compositions to cross the blood-brain barrier, or to cross cell membranes, formulations that increase the lipophilicity of the compound are particularly desirable. For example, the compounds of the invention can be incorporated into liposomes (Gregoriadis, *Liposome Technology*, Vols. I to III, 2nd ed. (CRC Press, Boca Raton Fla. (1993)). Liposomes, which consist of phospholipids or other lipids, are nontoxic, physiologically acceptable and metabolizable carriers that are relatively simple to make and administer.

For treating a circadian rhythm function disorder treatment, more than one therapeutic approach or compound can be provided to an individual for maximal symptom control. Thus, for use in modulating circadian rhythm function, a PK2 receptor antagonist or agonist or PK2 promoter modulator can advantageously be administered concurrently or sequentially with another therapeutic mode or formulated with a second compound that controls the same or related symptoms. For example, in treating circadian rhythm sleep disorders, a PK2 receptor antagonist or agonist can be administered while an individual is receiving light therapy, drug therapy and the like. Contemplated methods of modulating circadian rhythm include administering PK2 receptor antagonists or agonists alone, in combination with, or in sequence with, such other compounds. The skilled clinician will be able to determine concurrent or sequential therapies appropriate for use with a PK2 receptor antagonist or agonist.

It is expected that the PK2 receptor antagonists and agonists identified using the screening methods of the invention will have beneficial activities apart from, or in addition to, modulating circadian rhythm function. As described in Example V, high levels of PK2 receptor expression have been observed in discrete locations in the brain. In particular, PK2 receptor is expressed at high levels in SCN, paraventricular nucleus of hypothalamus (PVN), dorsal medial nucleus of hypothalamus (DMH), paraventricular and paratenial nuclei of thalamus (PVT/PT), paracentral thalamic nucleus (PC), lateral habenular nucleus (LHb) and lateral septal nucleus (LS) (see FIGS. 5 and 6).

The invention also provides an isolated nucleic acid molecule encoding a mouse PK2 receptor polypeptide. As described above, a mouse PK2 receptor, such as that having the amino acid sequence referenced as SEQ ID NO:2, which is encoded by the nucleotide sequence referenced as SEQ ID NO:1, is able to bind to PK2 and signal through a G-protein coupled signal transduction pathway and modulate circadian rhythm in mice.

The invention further provides an isolated nucleic acid molecule containing a PK2 gene promoter, which can be operatively linked to a heterologous nucleotide sequence. Exemplary human and mouse PK2 gene promoters include the human PK2 promoter (SEQ ID NO:14), human PK2 2.8 kb promoter (SEQ ID NO:15), mouse PK2 promoter (SEQ ID NO:16), mouse 2.8 kb PK2 promoter (SEQ ID NO:17), mouse 188 bp PK2 promoter (SEQ ID NO:18) and a 72 bp promoter containing the 4 human E-box enhancer elements of the human PK2 promoter linked together (SEQ ID NO:19).

As shown herein, PK2 gene expression is regulated in a circadian fashion (see Examples I, II and IV). As such, the PK2 promoter can be useful for cyclically regulating a variety of genes in a circadian fashion. For example, a PK2 promoter can be used to modulate expression of a therapeutic gene. Cyclic expression of a therapeutic gene can be advantageous, for example, when the presence of a gene product is most beneficial during a particular time of day, such as daytime when the individual is active.

A PK2 promoter can be operatively linked to a variety of heterologous nucleotide sequences, which can be, for example, a reporter nucleic acid, antisense nucleic acid, nucleic acid encoding a therapeutic polypeptide, or other sequence to be regulated in a circadian fashion. Exemplary reporter nucleic acids are described above, in relation to use of a PK2 promoter in screening methods.

The nucleic acid molecules of the invention also are suitable for a variety of screening applications. For example, the invention nucleic acid molecules can be used in the screening assays described herein. For example, an invention nucleic acid molecule containing a PK2 gene promoter can be used to identify compounds that modulate PK2 gene promoter activity. In addition, an invention nucleic acid molecule encoding mouse PK2 receptor can be expressed in a cell, which can be used in a screening assay, or the encoded PK2 polypeptide can be isolated for use in a screening assay. An invention nucleic acid molecule encoding mouse PK2 receptor also can be used as a probe or primer to identify and isolate PK2-encoding nucleic acid molecules from other species, or to identify structurally related molecules.

As used herein, the term "isolated nucleic acid molecule" is intended to mean that the nucleic acid molecule is altered, by the hand of man, from how it is found in its natural environment. For example, an isolated nucleic acid molecule can be a molecule operatively linked to an exogenous nucleic acid sequence. An isolated nucleic acid molecule can also be a molecule removed from some or all of its normal flanking nucleic acid sequences.

An isolated molecule can alternatively, or additionally, be a "substantially pure" molecule, in that the molecule is at least 60%, 70%, 80%, 90 or 95% free from cellular components with which it is naturally associated. An isolated nucleic acid molecule can be in any form, such as in a buffered solution, a suspension, a lyophilized powder, attached to a solid support (for example, as a component of a DNA array), or in a cell.

As used herein, the term "nucleic acid molecule" refers to a polynucleotide, including an oligonucleotide, of natural or synthetic origin, which can be single- or double-stranded, can correspond to genomic DNA, cDNA or RNA, and can represent either the sense or antisense strand or both.

The term "nucleic acid molecule" is intended to include nucleic acid molecules that contain one or more non-natural nucleotides, such as nucleotides having modifications to the base, the sugar, or the phosphate portion, or having one or more non-natural linkages, such as phosphorothioate linkages. Such modifications can be advantageous in increasing the stability of the nucleic acid molecule, particularly when used in hybridization applications.

Furthermore, the term "nucleic acid molecule" is intended to include nucleic acid molecules modified to contain a detectable moiety, such as a radiolabel, a fluorochrome, a ferromagnetic substance, a luminescent tag or a detectable binding agent such as biotin. Nucleic acid molecules containing such moieties are useful as probes for detecting the presence or expression of PK2 receptor nucleic acid molecule.

A nucleic acid molecule of SEQ ID NO:1 does not consist of the exact sequence of an EST present in publically available databases, including the sequences designated by GenBank Accession numbers XM_066104 and AL121755. Similarly, a nucleic acid molecule of SEQ ID NO:14 does not consist of the exact sequence of an EST present in publically available databases, including the sequences designated by GenBank Accession numbers AC096970.2, AF182067.1 and AC010207.18.

The invention further provides isolated oligonucleotides that contain at least 17 contiguous nucleotides from SEQ ID NOS:1 and 14, or the complement thereof. The oligonucleotides of the invention are thus of sufficient length to be useful as sequencing primers, PCR primers and hybridization probes to detect or isolate nucleic acid molecules. For example, an oligonucleotide of SEQ ID NO:1 can be used to detect or isolate nucleic acid molecules encoding PK2 receptor polypeptides, and are also useful as therapeutic antisense reagents to inhibit PK2 receptor expression. Such an oligonucleotide can, but need not, encode PK2 receptor polypeptides that are able to modulate circadian rhythm function in an animal. An oligonucleotide of SEQ ID NO:14 can be used to detect or isolate nucleic acid molecules containing a PK2 promoter and are also useful in the screening methods of the invention for identifying a compound that modulates circadian rhythm. Those skilled in the art can determine the appropriate length and sequence of a oligonucleotide of the invention for a particular application.

As used herein, the term "oligonucleotide" refers to a nucleic acid molecule that contains at least 17 contiguous nucleotides from the reference sequence and which can, but need not, encode a functional polypeptide. Thus, a oligonucleotide of the invention can contain at least 17, 20, 22 or 25 contiguous nucleotides, such as at least, or not more than, 30, 40, 50, 60, 70, 80, 90, 100, 125, 150, 175, 200, 250, or 300 contiguous nucleotides from SEQ ID NOS:1 or 14, or from their complement. An oligonucleotide of SEQ ID NO:1 does not consist of the exact sequence of an EST present in publically available databases, including the sequences designated by GenBank Accession numbers XM_066104 and AL121755. Similarly, an oligonucleotide of SEQ ID NO:14 does not consist of the exact sequence of an EST present in publically available databases, including the sequences designated by GenBank Accession numbers AC096970.2, AF182067.1 and AC010207.18.

For certain applications, it is desirable to use isolated oligonucleotide molecules of the invention that specifically hybridize to a target nucleic acid molecule. For example, for detecting PK2 receptor expression in a sample, it is desirable to use isolated oligonucleotide molecules of the invention that specifically hybridize to a nucleic acid molecule encoding a PK2 receptor. Similarly, for detecting a non-expressed nucleic acid, such as a PK2 promoter, in a sample, it is desirable to used isolated oligonucleotides molecules of the invention that specifically hybridize to a nucleic acid molecule containing a PK2 promoter.

As used herein, the term "specifically hybridize" refers to the ability of a nucleic acid molecule to hybridize, under moderately stringent conditions as described above, to the reference PK2 receptor nucleic acid molecule (SEQ ID NO:1) or PK2 promoter nucleic acid molecule (SEQ ID NO:14), without hybridization under the same conditions with nucleic acid molecules that are not PK2 receptor or PK2 promoter nucleic acid molecules, respectively, such as actin cDNA.

As used herein, the term "stringent conditions" refers to conditions equivalent to hybridization of a filter-bound nucleic acid molecule to a nucleic acid in a solution containing 50% formamide, 5× Denhart's solution, 5×SSC, 0.2% SDS at 42° C., followed by washing the filter in 0.1×SSC and 0.1% SDS at 65° C. twice for 30 minutes. Equivalent conditions to the stringent conditions set forth above are well known in the art, and are described, for example in Sambrook et al., *Molecular Cloning: A Laboratory Manual*, Cold Spring Harbor Laboratory, New York (1992).

Methods for preparing an invention nucleic acid molecule, or a nucleic acid molecule that is a PK2 receptor agonist or antagonist include well known chemical synthesis methods, such as automated methods, and recombinant methods, such as those described in Sambrook et al., *Molecular Cloning: A Laboratory Manual*, 3rd ed., Cold Spring Harbor Press, Plainview, N.Y. (2001); Ausubel et al. (*Current Protocols in Molecular Biology* (Supplement 47), John Wiley & Sons, New York (1999)). An exemplary method for preparing an isolated mouse PK2 receptor nucleic acid, human PK promoter region nucleic acid, or other nucleic acid molecules involves amplification of the nucleic acid molecule using specific primers and the polymerase chain reaction (PCR). Using PCR, a nucleic acid molecule having any desired boundaries can be amplified exponentially starting from only a few DNA or RNA molecules, such as from a single cell. PCR methods, including methods of isolating homologs of a given nucleic acid molecule in other species using degenerate primers, are well known in the art.

Alternatively, an. isolated nucleic acid molecule can be prepared by screening a library, such as a genomic library, cDNA library or expression library, with a detectable nucleic acid molecule or with an antibody. Human libraries, and libraries from a large variety of mammalian species, are commercially available or can be produced from species or cells of interest. The library clones identified as containing a particular nucleic acid molecule can be isolated, subcloned or sequenced by routine methods.

Furthermore, an isolated invention nucleic acid molecule, or nucleic acid molecule used in the methods of the invention, can be prepared by direct synthetic methods. For example, a single stranded nucleic acid molecule can be chemically synthesized in one piece, or in several pieces, by automated synthesis methods known in the art. The complementary strand can likewise be synthesized in one or more pieces, and a double-stranded molecule made by annealing the complementary strands. Direct synthesis is particularly advantageous for producing relatively short molecules, such as probes and primers, and also for producing nucleic acid molecules containing modified nucleotides or linkages.

The invention provides a vector containing an isolated nucleic acid molecule encoding a mouse PK2 receptor polypeptide (SEQ ID NO:1). The invention also provides a vector containing an isolated nucleic acid molecule containing a human PK2 gene promoter region (SEQ ID NO:14). Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. The vectors of the invention will generally contain elements such as an origin of replication compatible with the intended host cells; transcription termination and RNA processing signals; one or more selectable markers compatible with the intended host cells; and one or more multiple cloning sites. Optionally, the vector will further contain sequences encoding tag sequences, such as GST tags, and/or a protease cleavage site, such as a Factor Xa site, which facilitate expression and purification of the encoded polypeptide.

The choice of particular elements to include in a vector will depend on factors such as the intended host cells; the insert size; whether expression of the inserted sequence is desired; the desired copy number of the vector; the desired selection system, and the like. The factors involved in ensuring compatibility between a host cell and a vector for different applications are well known in the art.

In applications in which the vectors are to be used for recombinant expression of the encoded polypeptide, the isolated nucleic acid molecules will generally be operatively linked to a promoter of gene expression which may be present in the vector or in the inserted nucleic acid molecule. The choice of promoter to operatively link to an invention nucleic acid molecule will depend on the intended application, and can be determined by those skilled in the art. For example, if a particular gene product may be detrimental to a particular host cell, it may be desirable to link the invention nucleic acid molecule to a regulated promoter, such that gene expression can be turned on or off. Alternatively, it may be preferred to have expression driven by either a weak or strong constitutive promoter. Exemplary promoters suitable for mammalian cell systems include, for example, the SV40 early promoter, the cytomegalovirus (CMV) promoter, the mouse mammary tumor virus (MMTV) steroid-inducible promoter, and the Moloney murine leukemia virus (MMLV) promoter. Exemplary promoters suitable for bacterial cell systems include, for example, T7, T3, SP6, lac and trp promoters.

Also provided are cells containing an isolated nucleic acid molecule encoding a mouse PK2 receptor polypeptide. The isolated nucleic acid molecule will generally be contained within a vector. The isolated nucleic acid molecule can be maintained episomally, or incorporated into the host cell genome.

The cells of the invention can be used, for example, for molecular biology applications such as expansion, subcloning or modification of the isolated nucleic acid molecule. For such applications, bacterial cells, such as laboratory strains of *E. coli*, are useful, and expression of the encoded polypeptide is not required.

The cells of the invention can also advantageously be used to recombinantly express and isolate the encoded polypeptide. For such applications bacterial cells (for example, *E. coli*), insect cells (for example, *Drosophila* and *Spodoptera fugiperda*), yeast cells (for example, *S. cerevisiae, S. pombe*, or *Pichia pastoris*), and vertebrate cells (for example, mammalian primary cells and established cell lines, such as CHO, 293 and COS cells; and amphibian cells, such as *Xenopus* embryos and oocytes).

The invention provides an isolated mouse PK2 receptor polypeptide, which is encoded by the nucleotide sequence referenced as SEQ ID NO:1 and degenerate variants thereof. The isolated mouse PK2 receptor polypeptide can be used in assays to identify PK2 receptor antagonists and agonists.

The invention also provides compositions suitable for use in assays to identify PK2 receptor agonists and antagonists. Suitable compositions contain an isolated tissue, isolated cell or cell preparation, containing a mouse PK2 or PK1 receptor and a PK2 or PK1 polypeptide. A composition suitable for screening can contain either a PK2 or PK1 receptor in combination with either a PK2 or PK1 polypeptide. For example, suitable combinations include a PK2 receptor together with PK1 or PK2, as well as a PK1 receptor together with PK1 or PK2. Any of these combinations can be used to identify a compound that is a PK2 receptor antagonist or agonist because PK1 receptor and PK2 receptor are structurally similar and both bind to PK1 and PK, as well as to PK1/PK2 chimeras, such as SEQ ID NOS:20 and 21. A PK2 receptor contained in a composition of the invention does not include the exact sequence of an EST present in publically available databases, including the amino acid sequences designated by GenBank Accession numbers XM_066104 and AL121755. Similarly, a PK1 receptor contained in a composition of the invention does not include the exact sequence of an EST present in publically available databases, including the amino acid sequences designated by GenBank Accession number NM_021381, AF236082 and XM_066104.

A PK2 or PK1 receptor contained in the compositions can be, for example, a mammalian PK2 or PK1 receptor such as a mouse or human receptor. Exemplary mouse PK2 and PK1 receptor polypeptide sequences include those referenced as SEQ ID NOS:2 and 4, respectively. A PK2 or PK1 polypeptide contained in the compositions binds to a PK2 receptor, a PK1 receptor, or both. Exemplary PK2 polypeptides include human PK2s referenced as SEQ ID NOS:5 and 6 and mouse PK2s referenced as SEQ ID NOS:7 and 8. Exemplary PK1 polypeptides include human PK1 referenced as SEQ ID NO:9 and mouse PK1 referenced as SEQ ID NO:10. Orthologs of PK1 and PK2, such as Bv8 (SEQ ID NOS:11 and 12) and MIT1 (SEQ ID NO:13) that bind to a PK2 receptor or PK1 receptor also can be contained in a composition of the invention. A PK1 or PK2 in a composition of the invention optionally can be detectably labeled.

The compositions of the invention can also include crude or partially purified lysates or extracts of cells containing PK2 receptor or PK1 receptor, and reconstituted signaling systems containing PK2 receptor or PK1 receptor. Artificial signaling systems include, for example, natural or artificial lipid bilayers, such as a liposome or micelle, which promote an active conformation of PK2 receptor. The compositions can further contain cellular fractions or isolated components necessary for producing and detecting a desired predetermined signal.

A composition of the invention further can contain both PK1 receptor and PK2 receptor and either or both PK1 and PK2, or another PK1 receptor or PK2 receptor agonist, such as a PK2/PK1 chimera.

It is understood that modifications which do not substantially affect the activity of the various embodiments of this invention are also included within the definition of the invention provided herein. Accordingly, the following examples are intended to illustrate but not limit the present invention.

EXAMPLE I

Rhythmic Expression of Prokineticin 2 (PK2) in the Suprachiasmatic Nucleus (SCN)

This example shows that PK2 mRNA is expressed rhythmically in the SCN of mouse.

In situ hybridization was used to detect a mouse PK2 mRNA transcript in the mouse brain. Antisense and sense riboprobes containing the coding region of mouse PK2 or the 3'UTR (untranslated region) of mouse PKR2 were generated. The 3'UTR of the PKR1 and PKR2 were used as these receptors are over 80% identical at nucleic acid sequence level in their coding regions. In situ hybridizations were processed as described in (Winzer-Serhan et al., *Brain Res. Protocols* 3:229-41 (1999)). The mRNA distributions were analyzed in autoradiograms and emulsion-dipped sections. Specific hybridization signals were quantitatively analyzed using a video-based computer image analysis system (MCID, Imaging Research, St. Catharine's, Ontario, Canada). A calibration curve of optical density versus radioactivity (dpm/mg tissue wet weight) was constructed using $^{14}C$-standards. Specific hybridization signals in SCN were obtained by subtracting background values obtained from adjacent brain areas that have no hybridization signal. Data were normalized with respect to the differences between signal intensities in equal areas of SCN.

The results from these in situ hybridization studies indicated that PK2 mRNA is present in the SCN and other discrete brain areas including the islands of Calleja, medial preoptic area of the hypothalamus, and the shell of the nucleus accumbens. FIG. 1a shows PK2 mRNA expression in coronal sections (20 μm) of the mouse brain. The nucleus accumbens (NAc); islands of Calleja (ICj); medial preoptic area (MPA) and suprachiasmatic nucleus (SCN) are shown in FIG. 1a (Scale bar=2 mm).

To determine the time dependence of the presence of PK2 mRNA in the SCN, male adult C57Bl6 mice (Taconic Farms, N.Y.) were entrained under a 12-hr light:12-hr dark (LD) cycle. Quantification of PK2 mRNA in the SCN at various time points indicated the presence of circadian oscillation profiles in LD. Animals were studied under LD, or constant darkness for 2 days (2DD) or 8 days (8DD). FIG. 1b shows temporal profiles of PK2 mRNA in SCN; each value is the mean±SEM of 3-6 animals, with data at ZT/CT1-7 being double plotted. Shaded and closed horizontal bars indicate light and dark periods, respectively. As indicated by FIG. 1b, it was observed that PK2 mRNA is highest during light phase (ZT1-ZT7) (ZT, Zeitgeber time; ZT0=light on, ZT12=light off), and lowest during dark phase (ZT13-ZT22). The oscillation magnitude of PK2 mRNA was observed to be high, with the peak level at least 50-fold higher than the lowest level. FIG. 1c shows representative images of PK2 mRNA expression described in FIG. 1b (Scale bar=1 mm). FIG. 1c shows that PK2 mRNA level was essentially undetectable in SCN during dark phase. Oscillation of PK2 expression was not detected in other PK2 mRNA-positive areas such as the medial preoptic area or the islands of Calleja (FIG. 1c). The closely-related PK1 mRNA was not expressed at a detectable level in the brain areas examined, including the SCN.

The oscillation of PK2 mRNA was maintained under constant darkness (DD) (FIG. 1b, c). After 2 days in DD, PK2 mRNA levels were high from CT1-CT7 (CT, circadian time; CT0, subjective light on; CT12, subjective light off), and remained low from CT13-CT22. However, after 8 days in DD, the period of low PK2 expression expanded from about 9-hr in LD to 12-hr, with a slight reduction in peak level. The robust circadian profile of PK2 mRNA in the SCN indicates that PK2 regulates SCN circadian pacemaker and/or its output.

In summary, this example shows that PK2 mRNA presence in the SCN of mouse corresponds to a circadian oscillatory profile.

EXAMPLE II

Regulation of PK2 Transcription by Clock Genes

This example shows that PK2 gene transcription is regulated by clock genes.

The promoter sequence of human PK2 gene was examined (Jilek et al., *Gene* 256:189-95 (2000)) to determine the role of E-box enhancers in CLOCK-BMAL1-mediated transcriptional activation (Gekakis et al., *Science* 280:1564-69 (1998); and Hogenesch et al., *Proc. Natl. Acad. Sci. USA* 95;5474-79 (1998)). FIG. 2a shows the location of four E-boxes (E) and cAMP-responsive element (CRE) identified within 2.4 kb of the 5'-flanking region of the mouse PK2 gene. The numbered axis represents distance in kilo base pairs (kb) from the putative transcription start site, marked as 0. All four E-boxes are conserved in the 5'-flanking region of mouse PK2 gene. A GenBank search indicated that these four E-box elements are conserved in the 5'-flanking sequence of the mouse PK2 gene, including the approximate location of each of the four E-boxes. No E-box sequence was identified in 5 kb 5'-flanking region of the closely-related PK1 gene.

To examine the ability of CLOCK:BMAL1 heterodimers to drive PK2 transcription through E-box enhancers, a 2.8 kb fragment of the mouse PK2 5'-flanking region was cloned into a promoterless luciferase reporter vector (pGL3-Basic).

The ability of transcription factors to promote transcriptional activity of the mouse PK2 promoter was examined. Transcriptional activation of luciferase reporter linked to 2.8 kb (PK2.8-Luc) and 200 bp (PK0.2-Luc) of the 5'-flanking region of mouse PK2 gene was studied. In addition, a luciferase reporter was linked to a mutated E-box (GGATCT) (PK0.2M-Luc).

HEK293 and NIH3T3 cells were grown in Dulbecco's Modified Eagle Medium (DMEM) supplemented with 10% fetal bovine serum. Cells were plated and transfected with Lipofectamine (Invitrogen, Carlsbad, Calif.) in six-well plates. 10 ng of firefly luciferase reporter plasmid, 250 ng of mBmal1 and mClock and 500 ng of mPer1, mPer2, mPer3, mCry1, and mCry2 were used. The total amount of DNA (1 mg per well) was adjusted with pcDNA3.1 vector as carrier. 48-hr after transfection, cells were washed and lysed with 200 µl reporter lysis buffer. Portion of the cell extract (20 µl) was mixed with Luciferase Assay Reagent (Promega) and the reaction monitored for 10 s in a Monolight 2010 luminometer (Analytical Luminescence Laboratory, San Diego, Calif.). For Chinese Hamster Ovary (CHO) cells and CHO cells that stably express PKR2 (CHO-PKR2), cells were grown in α-MEM, transfected with the same method as for HEK293 and NIH3T3 cells. 42-hr after transfection, cells were treated with increasing concentrations of purified recombinant mouse PK2 (0-50 nM) for 6 hrs and then lysed. Luciferase activities were normalized to protein concentration.

In FIG. 2b, the letters C and B indicate CLOCK and BMAL1, respectively. The luciferase activity of PK2.8-Luc in the absence of C and B was designated as 1 unit. The results shown in FIG. 2b indicate that CLOCK and BMAL1 together, but neither alone, produced a strong increase in transcriptional activity (172-fold). One proximal E-box, residing within 130 bp upstream of the putative PK2 transcriptional start site, was also transactivated by CLOCK:BMAL1 heterodimers. This CLOCK:BMAL1-dependent activation was abolished when the E-box sequence CACGTG was mutated.

The transcriptional activity of a 72 bp construct in which the four E-boxes and their immediate flanking sequence were linked together (PK4E-Luc) was examined. The construct was generated by subcloning annealed oligonucleotides PK4E5 and PK4E3 into a luciferase reporter vector containing SV40 promoter (pGL3-Promoter). A comparable construct with all four E-boxes mutated (PK4EM-Luc) was similarly constructed with oligonucleotides PK4E5M and PK4E3M. All four E-boxes were mutated in PK4EM-Luc. The luciferase activity of pGL3-Basic was designated as 1 unit. As shown in FIG. 2C, CLOCK and BMAL1 together (but neither alone) caused a substantial increase in transcriptional activity through these four E-boxes (162-fold). This CLOCK:BMAL1-dependent activation was reduced to background level of activation when all four E-boxes were mutated. These results indicate that transcriptional activation by CLOCK:BMAl1 heterodimers requires at least one E-box.

Using the 2.8 kb PK2 promoter, the effects of negative elements of the SCN clockwork were examined. Inhibition of CLOCK:BMAL1-mediated transcription from PK2.8-Luc by mPers and mCrys was examined. The luciferase activity of PK2.8-Luc in the presence of C and B was designated as 100%. As shown in FIG. 2d, it was observed that mPERs caused 40%-60% inhibition of CLOCK:BMAL1-induced transcription, while the inhibition mediated by mCRY1 and mCRY2 was close to completion. Taken together, these in vitro studies indicate that clock gene products can regulate PK2 transcription.

The role of PKR2 activation on PK2 gene expression was examined by stably expressing PKR2 in Chinese Hamster Ovary cells (CHO-PKR2) and transfecting CHO-PKR2 cells with the 2.8 kb PK2 promoter fused to luciferase reporter nucleic acid. To prepare the PK2 promoter containing constructs, a 2.8 kb 5'-flanking region of the mouse PK2 gene was subcloned into pGL3-BASIC vector to generate PK2.8-Luc. 170 bp 5'-flanking region of the mouse PK2 gene containing a single E-box was synthesized with four long oligonucleotides and subcloned into the pGL3-BASIC vector to generate PKO.2-Luc. A mutant 5'-flanking sequence with the E-box CACGTG was created similarly with mutant oligonucleotides (PK0.2M-Luc). The luciferase activity of PK2.8-Luc in CHO cells in the absence of PK2 treatment was designated as 1 unit.

As shown in FIG. 2e, activation of PKR2 by PK2 dose-dependently stimulates CLOCK:BMAL1-mediated transcription of the 2.8 kb PK2 promoter (4.0±0.4 fold, Mean±SEM, n=3). The EC50 values of PK2 were 7.8±2.9 nM (n=3), similar to EC50 values (7.3±1.5 nM, n=4) obtained from the calcium mobilization of PKR2 activation by PK2. In the absence of CLOCK and BMAL1, activation of PKR2 alone by PK2 treatment (50 nM for 6 hr) did not activate the transcription of the 2.8 kb PK2 promoter [luciferase activity: 1.0±0.11, and 1.14±0.09, for CHO and CHO-PKR2, respectively]. In the presence of CLOCK and BMAL1, the stimulatory effect of PKR2 activation on the transcription of the 2.8 kb PK2 promoter was abolished by mCRY1 and mCRY2. Thus, PK2 can activate its own transcription in the SCN via activation of PKR2 in clock gene products-dependent manner.

In FIG. 2b-2e, the value shown is the mean±SEM of three replicates from a single assay. The results shown were representative of at least three independent experiments.

In summary, this example shows that the mouse PK2 promoter can be regulated by CLOCK:BMAL1 heterodimers, mPERs, mCRY1 and mCRY2.

EXAMPLE III

Altered PK2 Rhythm in Clock Mutant Mice

This example shows that rhythmic expression of PK2 mRNA is disturbed in Clock-deficient (Clk/Clk) and Cryptochrome-deficient (Cry/Cry) mice.

Genetic studies with mutant animals have provided insight into the mechanism of the mammalian molecular clock. Mice deficient in mCry1, mCry2, and mPer3 show subtle changes in circadian cycle length, but without causing arrhythmicity (Vitaterna et al., *Proc. Natl. Acad. Sci. USA* 96:12114-19 (1999); Thresher et al., *Science* 282:1490-94 (1998); Shearman et al., *Mol. Cell Biol.* 20:6269-75 (2000); and van der Horst et al., *Nature* 398:627-30 (1999)). Mutations in Clock, mPer1 or mPer2 genes result in a more severe circadian phenotype which includes arrhythmicity after long-term housing in constant darkness (DD)(Cermakian et al., *EMBO J.* 20:3967-74 (2001); Vitaterna et al., *Science* 264:719-25 (1994); King et al., *Cell* 89:641-53 (1997); Bae et al., *Neuron* 30:525-36 (2001); and Zheng et al., *Cell* 105:683-94 (2001)). Mice with disrupted Bmal1 gene, or deficient in both mPer1 and mPer2 exhibit the most severe phenotype: they are arrhythmic immediately after placement in DD (Bae et al., *Neuron* 30:525-36 (2001); Zheng et al., *Cell* 105:683-94 (2001); and Bunger et al., *Cell* 103:1009-17 (2000)). Similar arrhythmicity also occurs in mice deficient in both mCry1 and mCry2 genes (Vitaterna et al., *Science* 264:719-25 (1994); and van der Horst et al., *Nature* 398:627-30 (1999)). The cloning of the Tau gene, which encodes a casein kinase and whose mutation causes a shortened circadian cycle in a strain of hamster, has revealed the importance of post-transcriptional mechanisms for SCN clockwork (Lowrey et al., *Science* 288, 483-91 (2000)).

In contrast to SCN pacemaker clockwork, relatively little is known about the mechanism by which circadian pacemaker systems transmit timing information to control physiology and behavior (Reppert and Weaver, *Ann. Rev. Physiol.* 63:647-76 (2001); Allada et al., *Ann. Rev. Neurosci.* 24:1091-119 (2001); and Hardin, *Genome Biol* 1, REVIEWS1023 (2000)). In *Drosophila*, pigment dispersing factor, a neuropeptide, and takeout, a clock-controlled gene that appears to encode a secreted protein, have been demonstrated as mediators that transmit circadian activity rhythms (Renn et al., *Cell* 99:791-802 (1999); and Sarov-Blat et al., *Cell* 101: 647-56 (2000)). In mammals, transplant studies have indicated that signals that mediate the rhythmic output of the SCN also appear to be secreted molecules (Ralph et al., *Science* 247:975-8 (1990); Silver et al., *Nature* 382:810-13 (1996); and Earnest et al., *Science* 283:693-5 (1996)), but their biochemical identities are unknown.

Figure 3:
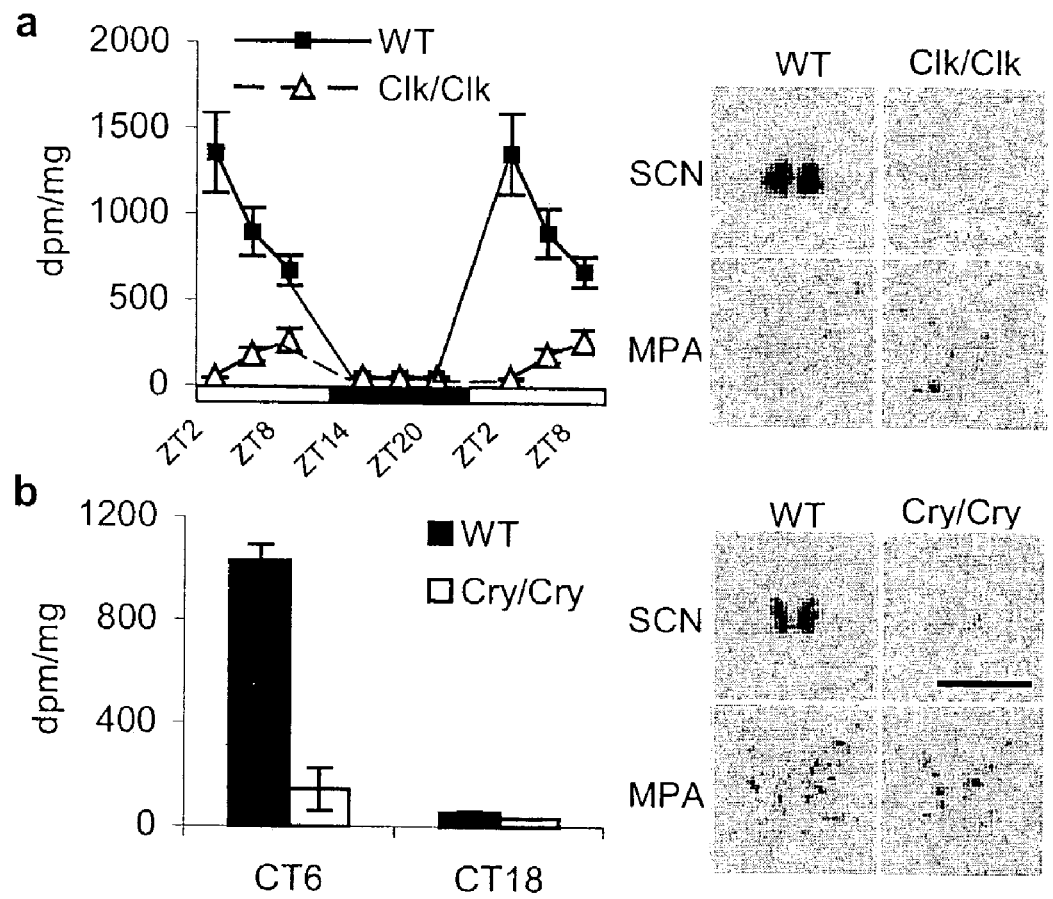
FIG. 3 shows rhythmic expression of PK2 mRNA in Clock-deficient (Clk/Clk) or Cryptochrome-deficient (Cry/Cry) mice.

PK2 mRNA levels were examined in the SCN of mutant mice deficient in Clock (Clk/Clk)(Vitaterna et al., *Science* 264:719-25 (1994)) or Cryptochromes [(mCry1-/-, mCry2-/-), mCry-deficient] (van der Horst et al., *Nature* 398:627-30 (1999)). Methods for preparing sections through the SCN of Clk/Clk mice (on a BALB/c genetic background) and of mCRY-deficient mice (mCry1-/-, mCry2-/-, on a C57BL/6-129 hybrid background) and their respective littermate controls were obtained as previously described (Shearman et al., *Science* 288:917-24 (2000).; and Jin et al., *Cell* 96:57-68 (1999)). As shown in FIG. 3A, the circadian rhythm of PK2 mRNA in the SCN was observed to be severely blunted in Clk/Clk mutants under LD. The left graph in FIG. 3A depicts the temporal profiles of PK2 mRNA in SCN of Clk/Clk mice. Representative coronal sections (15 mm) of PK2 mRNA at ZT2 of wild type (WT) and Clk/Clk mice in SCN and MPA are shown on the right. Data for ZT2-8 are double plotted.

In Clk/Clk mice, PK2 mRNA was detectable only at ZT5-ZT8. The reduced peak level of PK2 mRNA in Clk/Clk mice was also observed to be shifted from about ZT4 to ZT8. It should also be noted that the PK2 mRNA levels in medial preoptic area did not change in Clk/Clk mice. These results show that the decrease in PK2 gene expression in Clk/Clk mice is specific for the SCN circadian clock. The severe blunting of PK2 circadian rhythm in Clk/Clk mice indicates that CLOCK has a positive regulatory effect on the expression of PK2 gene.

PK2 mRNA levels in the SCN of mCry-deficient mice also were examined. The left graph of FIG. 3b depicts the expression of PK2 mRNA in SCN of Cry/Cry mice at CT6 and CT18. Representative coronal sections of PK2 mRNA at CT6 of WT and Cry/Cry mice in SCN and MPA are shown on the right (scale bar=1 mm). Each value is the mean±SEM of 5-6 animals.

In contrast to the oscillation pattern seen in the SCN of wild type mice, PK2 mRNA levels were low at both CT6 and CT18 in mCry-deficient mice (FIG. 3b). PK2 mRNA levels in medial preoptic area were not observably different from wild type mice at both circadian times. The apparent low levels of PK2 at both circadian times in mCry-deficient mice appear unexpected as mCRYs are major inhibitors of CLOCK: BMAL1-mediated transcription (Kume et al., *Cell* 98:193-205 (1999)) and tonic mid-high mPer1 and mPer2 mRNA levels have been observed in mCry-deficient mice (Vitaterna et al., *Proc. Natl. Acad. Sci. USA* 96:12114-19 (1999); and Okamura et al., *Science* 286:2531-34 (1999)). The immediate arrhythmicity of mCry-deficient mice in DD indicates the disruption of the functional circadian clock (van der Horst et al., supra).

In the absence of functional positive and negative limbs of the feedback loops, the absolute levels of PK2 mRNA likely depend on basal promoter activity and RNA stability. The essentially undetectable levels of PK2 mRNA in the SCN during the dark phase (FIG. 1b, c) suggest low basal PK2 promoter activity. It should also be noted that there are multiple copies of mRNA destability signal (AUUUA) in the 3'-untranslated regions of both the human and mouse PK2 mRNAs. These combined effects could contribute to the low levels of PK2 mRNA in the SCN in mCry-deficient mice. Taken together, these studies with mutant mice support that PK2 is a clock-controlled gene.

In summary, this example shows that mutant mice deficient in Clock (Clk/Clk) or Cryptochromes (mCry1-/-, mCry2-/-) have altered levels of PK2 mRNA in the SCN compared to wild type mice.

EXAMPLE IV

Response of PK2 Rhythm to Light Entrainment

This example shows that PK2 expression is altered by light entrainment of mice.

Figure 4:
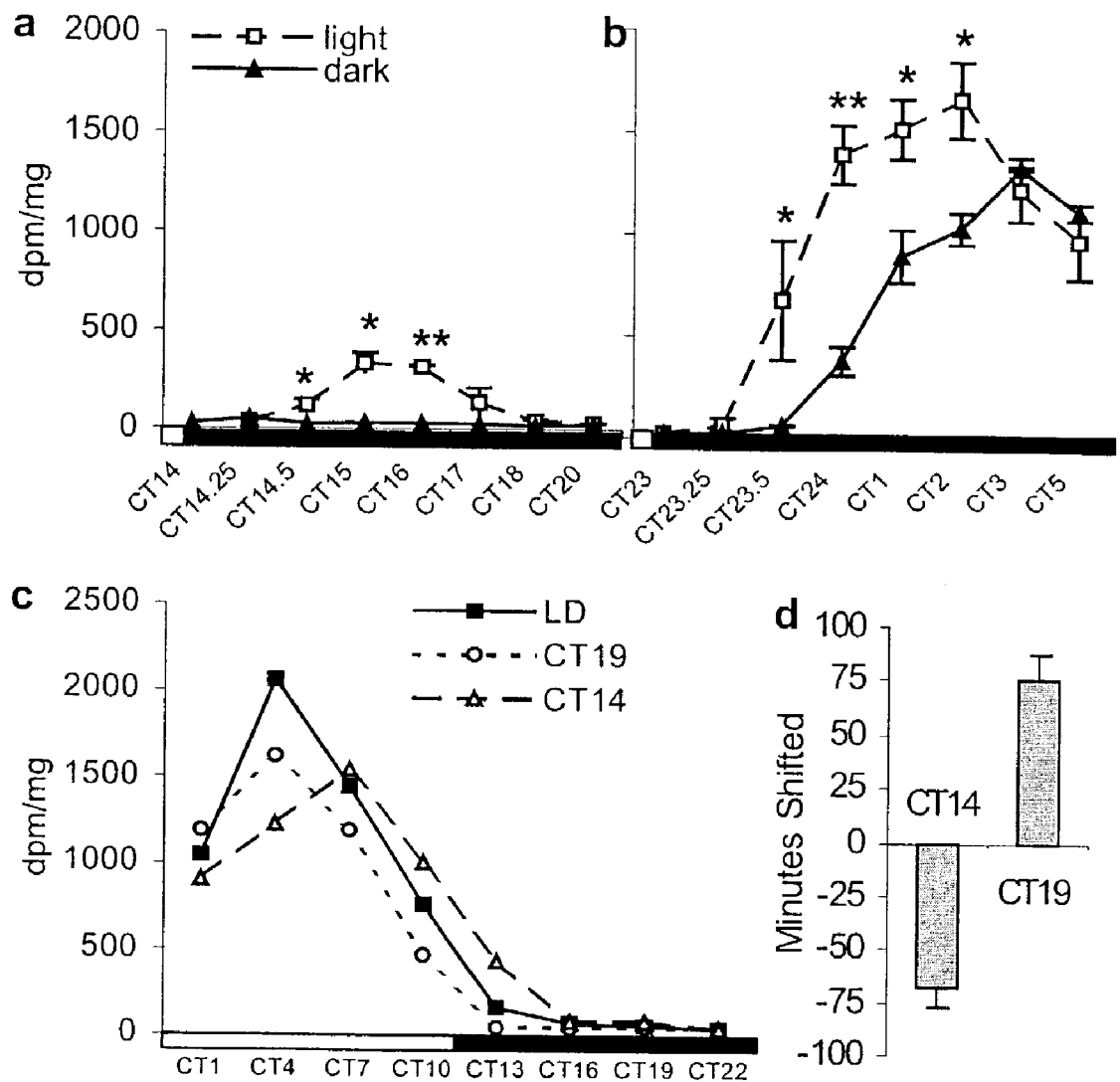
FIG. 4 shows that PK2 rhythm in SCN responds to light entrainment when animals are exposed to a 15-min light pulse at CT14 (FIG. 4a) or CT23 (FIG. 4b).

The PK2 mRNA level in the SCN in response to light pulses was examined. Animals were exposed to a 15 min light pulse at CT14 (FIG. 4a) or CT23 (FIG. 4b) on the first day in DD. Light pulses were 400 Lux for 15 min (FIG. 4a, b) and 400 Lux for 1 hr (FIG. 4c), respectively. In FIG. 4, open symbols and dashed lines denote light-exposed animals; closed symbols denote time-matched controls maintained in DD. Each value is the mean±SEM of 4-6 animals. Statistical analyses were performed using t-tests. *p<0.05, **p<0.01.

As shown in FIGS. 4a and 4b, PK2 mRNA levels increased rapidly and transiently 30 min after light exposure at both CT14 and CT23. At CT14, PK2 mRNA remained undetectable without light pulse. Following light exposure, PK2 mRNA levels increased by 30 min, peaked at 1-2 hr, and returned to control levels 4 hr after exposure. At CT23, PK2 mRNA levels rose with or without light pulse. However, in the presence of light pulse, PK2 mRNA levels increased more rapidly and robustly. PK2 mRNA returned to control levels 4 hr after exposure. At CT3, however, light pulse had no enhancing effect on PK2 mRNA levels. The light-inducibility of PK2 may result from activation of the CRE in the PK2 promoter (FIG. 2a).

The effect of light pulses that shift the phases of SCN-controlled behavioral rhythms on the phase of PK2 rhythm was also examined. Animals were exposed to 1-hr light pulse at CT14-15 or CT19-20 on the first day in DD. Control animals received no light pulse. In FIG. 4c, shaded and closed horizontal bars indicate light and dark periods under DD, respectively. FIG. 4d shows quantification of phase shifts (min, n=3) shown in FIG. 4c. The shift was measured at half-peak level of PK2 mRNA. By convention, delays are negative and advances are positive. One of the three experiments is shown.

As shown in FIGS. 4c and 4d, light pulses administered during early subjective night (CT14) cause about 70 min delay in the phase of PK2 expression. Similarly, light pulses administered during late subjective night (CT19) cause about 75 min advance in the phase of PK2 expression. These results indicate that light pulses that shift the phase of SCN-controlled behavioral rhythm alters the phase of PK2 expression. These light-induced shifts of PK2 rhythm correlate well with the shifts of locomotor rhythm.

Figure 7:
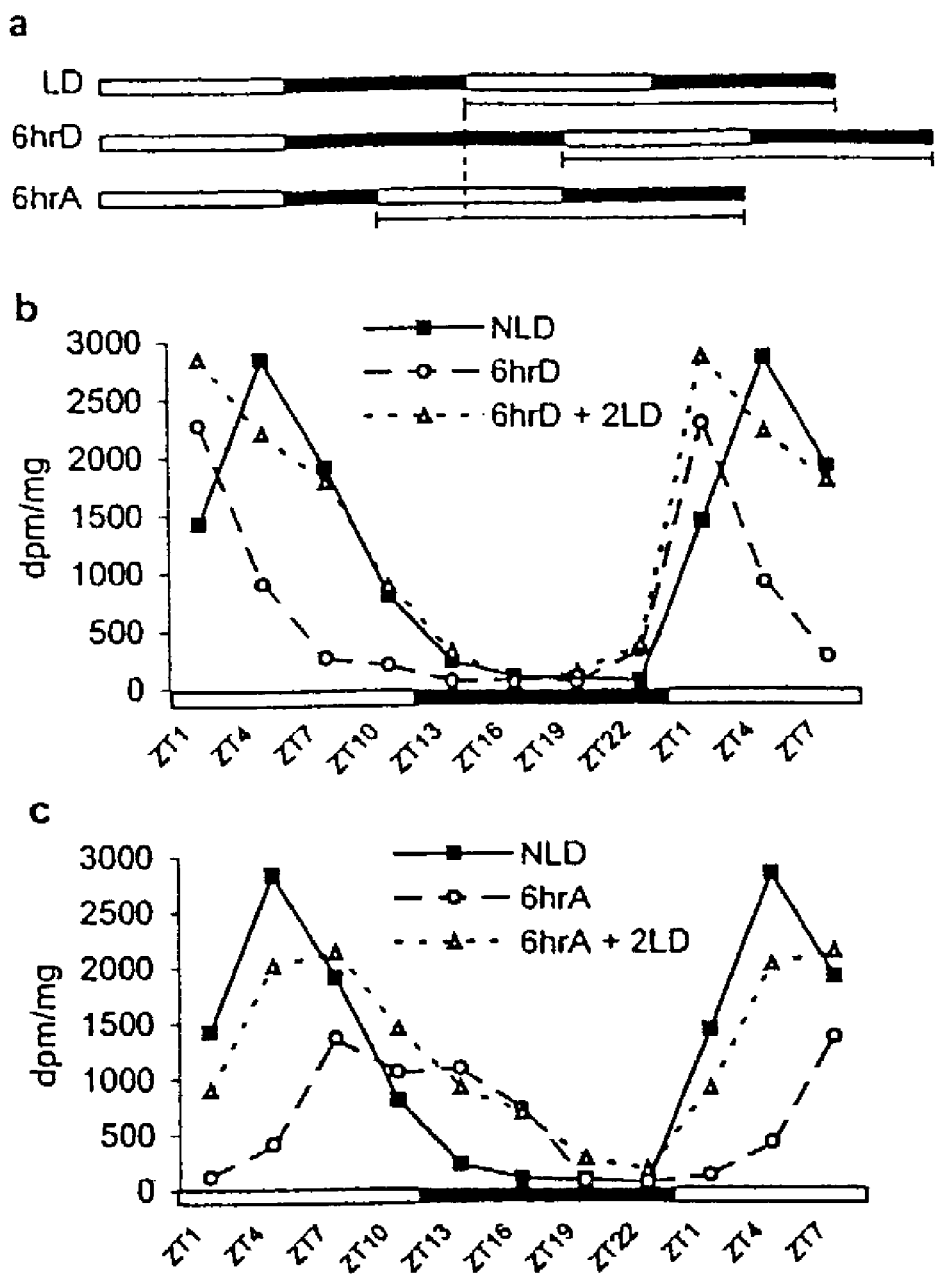
FIG. 7 shows PK2 mRNA expression in the SCN in response to abrupt shifts of light/dark cycles.

FIG. 7 shows PK2 mRNA expression in the SCN in response to abrupt shifts of light/dark cycle. Animals were entrained to 12 hours of light/12 hours of dark. The normal light/dark cycle (LD) was either delayed by 6 hours (6 hrD) or advanced by 6 hours (6 hrA). The periods of mouse brain samples are indicated by parentheses. Open and closed bars represent light and dark periods, respectively. FIG. 7b shows PK2 mRNA expression in normal LD, 6 hrD and 6 hrD +2 LD (6 hour delay followed by adaptation of 2 additional days). FIG. 7c shows PK2 mRNA expression in normal LD, 6 hrA and 6 hrA+2 LD (5 hour advance followed by adaptation of 2 additional light/dark cycles). Each value represents the average of 2 animals.

Figure 8:
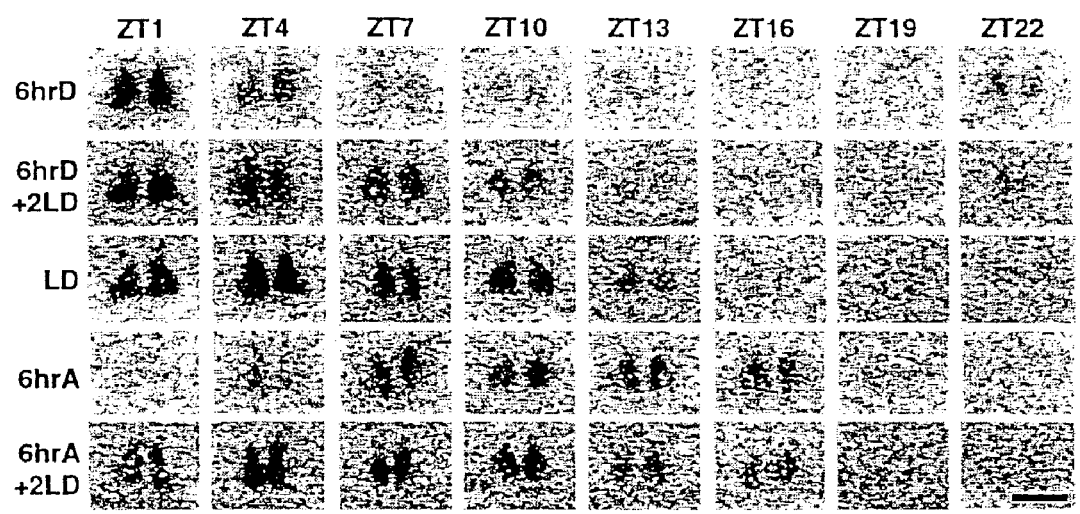
FIG. 8 shows temporal profiles of PK2 mRNA in the SCN in response to abrupt shifts of light/dark cycle.

FIG. 8 shows temporal profiles of PK2 mRNA in the SCH in response to abrupt shifts of light/dark cycles. Animals were entrained to 12 hours light/12 hours day and subjected to either normal light/dark cycle (LD), 6 hour delay (6 hrD), 6 hour delay followed by adaptation of 2 additional light/dark cycles (6 hrD+2 LD), 6 hour advance (6 hrA), or 6 hour advance followed by adaptation of 2 additional light/dark cycles (6 hrA+2 LD). Representative images of coronal sections (20 μm) at the SCN levels are shown. Scale bar=1 mm.

In summary, this example shows that PK2 rhythm in SCN responds to light entrainment.

EXAMPLE V

Expression of PK2 Receptor in SCN Output Targets

This example shows PK2 receptor expression in the mouse brain.

Figure 5:
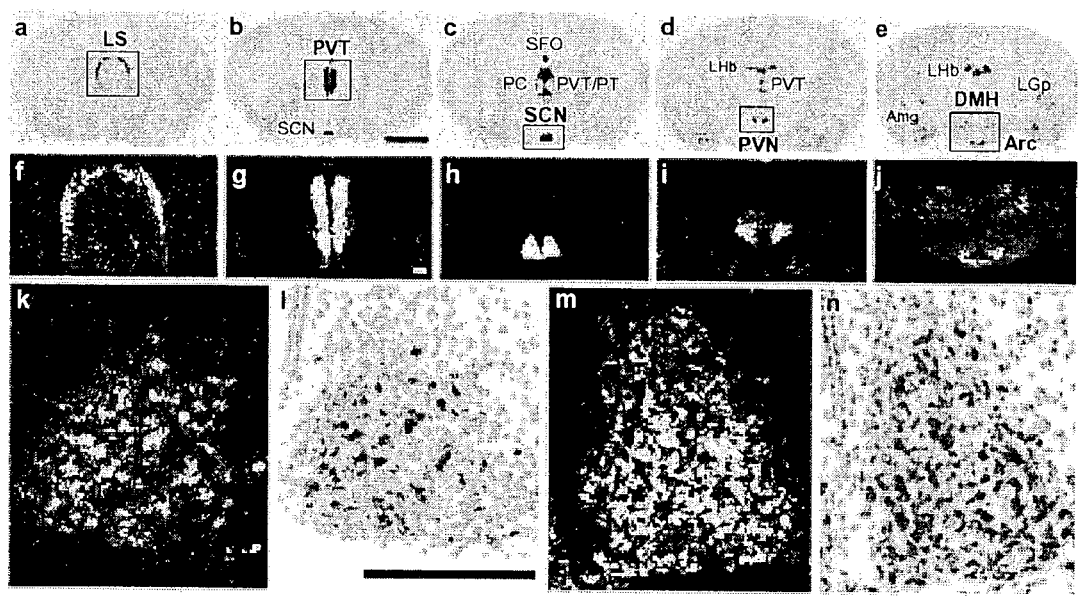
FIG. 5 shows expression of PK2 receptor (PKR2) mRNA in mouse brain.

Expression of PK2 receptor mRNA in male adult C57Bl6 mouse brain was examined by in situ hybridization. FIG. 5, top panel (a-e), represents autoradiographic images of PKR2 mRNA in lateral septum (LS), paraventricular thalamic (PVT) and hypothalamic nucleus (PVN), suprachiasmatic nucleus (SCN), paratenial nucleus (PT), paracentral nucleus (PC), lateral habenula (LHb), dorsal medial hypothalamic nucleus (DMH) and arcuate nucleus (Arc). FIG. 5, middle panel (f-j), depicts dark field microscopic images of PKR2 mRNA from the boxed regions in top panel (a-e). FIG. 5, bottom panel, depicts microscope images of PK2 (k,l) and PKR2 mRNA (m, n) in SCN at high magnification. Both dark field (k,m) and cresyl-violet stained sections (l,n) are shown. For top panel, scale bar=2 mm; for middle and bottom panels, scale bar=0.5 mm. All images were obtained from mouse brains collected at ZT1.

Figure 6:
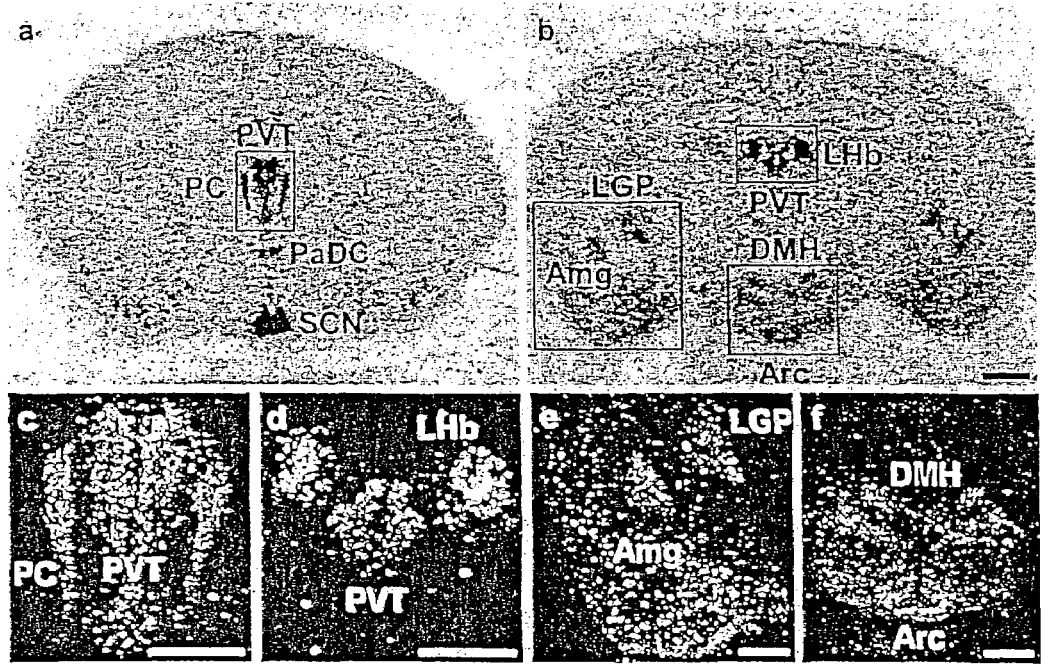
FIG. 6 shows PK2 receptor (PKR2) mRNA expression in mouse brain.

It was found that PKR2 mRNA is abundantly expressed in the SCN, paraventricular nucleus of hypothalamus (PVN), dorsal medial nucleus of hypothalamus (DMH), paraventricular and paratenial nuclei of thalamus (PVT/PT), paracentral thalamic nucleus (PC), lateral habenular nucleus (LHb) and lateral septal nucleus (LS). As shown in FIG. 6, PKR2 mRNA is also moderately expressed in lateral globus pallidus (LGP), amygdala and other regions.

The highest expression of PKR2 was found in PVT. Intriguingly, most of the PKR2 mRNA-positive nuclei are the primary target areas of SCN output pathway (Klein et al., *New York: Oxford Univ. Press*. 467 pp. (1991); Moore, *Ann. Rev. Med.* 48:253-66 (1997); Sofroniew and Weindl, *Amer. J. Anat.* 153:391-429 (1978); Watts et al., *J. Comp. Neurol.* 258:204-29 (1987); Watts and Swanson, *J. Comp. Neurol.* 258:230-52 (1987); Leak and Moore, *J. Comp. Neurol.* 433: 312-34 (2001); and Buijs, *Prog. Brain Res.* 111:229-40 (1996)). The high expression of PKR2 in these primary target areas of SCN output indicates that PK2 could serve as a signaling molecule mediating SCN output. PKR2 mRNA is also extensively expressed in the SCN (FIGS. 5c, h, m). In contrast to the robust rhythm of PK2 mRNA, PKR2 mRNA in the SCN and other PKR2-positive nuclei is non-oscillating. High magnification microscopic images show that most neurons within the SCN express both PK2 and PKR2 mRNAs (FIGS. 5k-n). This expression pattern of PK2 and PKR2 mRNA in the SCN indicates that the PK2/PKR2 system could play a role in synchronizing SCN output.

EXAMPLE VI

PK2 Administration Alters Circadian Locomotor Activity

This example shows that PK2 administration to rats alters their circadian locomotor activity.

To directly assess whether PK2 mediates the circadian behavioral output, the effects of intracerebroventricular (icv) injection of recombinant PK2 on wheel-running behavior was examined. Recombinant human PK2 was produced and purified as described previously (Li et al., *Mol. Pharm.* 59;692-8 (2001)). Male Sprague-Dawley rats (300-350g) were used to assess pharmacological effects of PK2 on locomotor rhythms. A 23-gauge guide cannula was implanted to the lateral ventricle (0.4 mm rostral to bregma, 3.0 mm ventral to dura, 2.4 mm lateral to midline, Charles River Laboratory). A 30-gauge stylet was placed in the guide cannula to maintain patency. Rats were housed in running-wheel cages for two weeks in LD, placed in DD for 2-5 days and then subjected to icv injection of recombinant PK2 at CT14. During icv injections, the stylet was removed and a 30-gauge injector attached to a Hamilton syringe by plastic tubing was inserted. Each animal received either 5 μl (1 mg/ml) of PK2 or saline (under dim red light <1 lux) over a 2-minute period. Animals were immediately returned to their cages and wheel-running activities were monitored in constant darkness with a PC system (Colbourn Instrument, Allentown, Pa.). Running-wheel data were analyzed at 5 minute intervals. Inhibition of nocturnal wheel-running was measured as activity counts during CT15-CT24, and expressed as a percentage of average counts obtained from the same time intervals of two days prior to treatment. Activation of wheel-running in subjective day in PK2-treated rats was measured as activity counts during CT0-CT12, and expressed as a percentage of average counts obtained from two nights (CT13-CT24) prior to treatment.

FIGS. 9a and 9b show representative actograms of rats injected with PK2 or saline at CT14. Shaded and closed horizontal bars indicate subjective light and dark periods under DD, respectively. The highlighted areas indicate night locomotor activity after treatment. The boxed areas represent locomotor activity during subjective day following treatment. FIG. 9c shows quantification of night and day locomotor activity following delivery of PK2 (n=7) or saline (n=6). The effect of PK2 on wheel-running activity during night phase (CT15-CT24) and day phase (CT0-CT12) was expressed as a percentage of nightly activity. Statistical analyses were performed using t-tests (**p<0.01).

Figure 9:
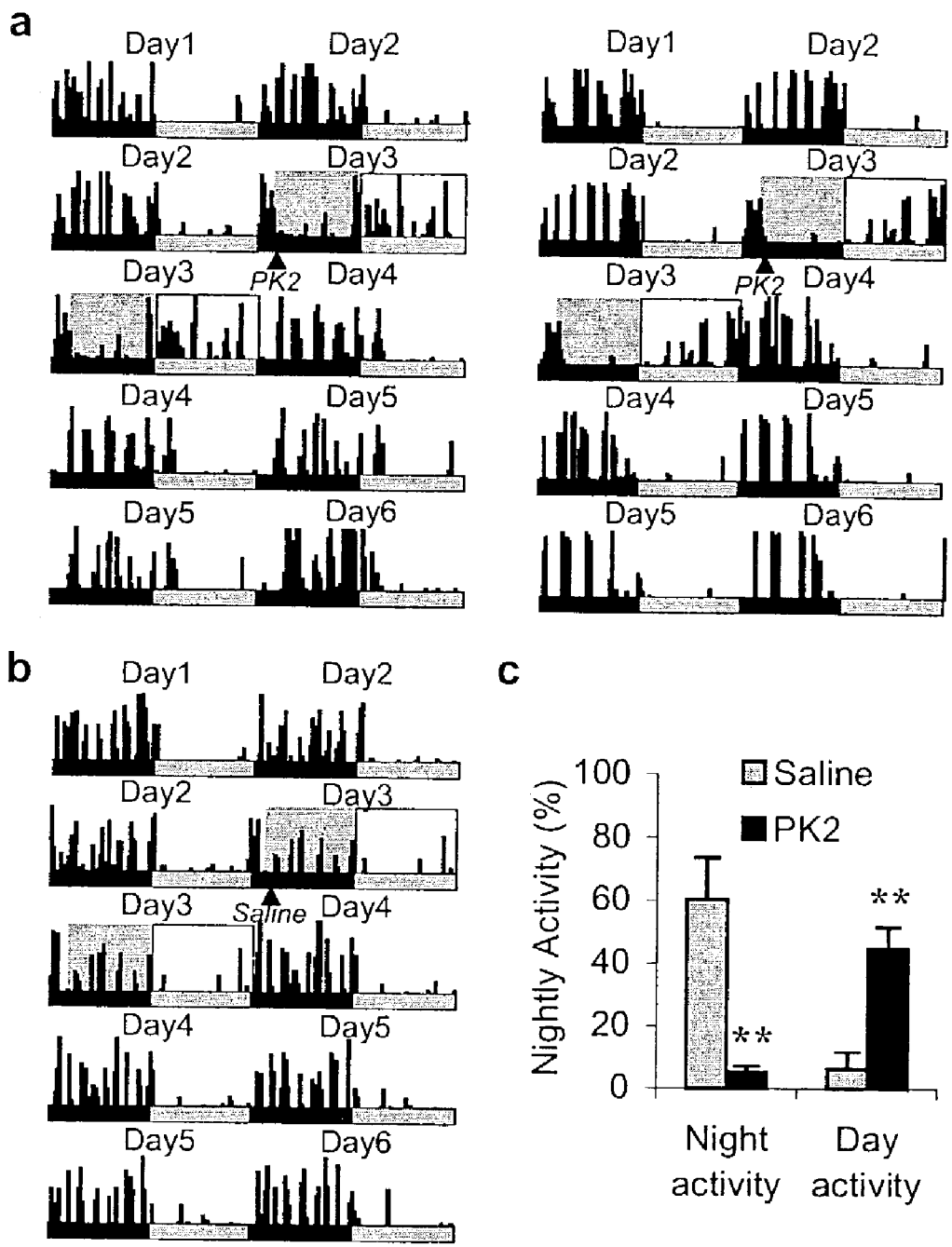
FIG. 9 shows the effect of intracerebroventricular delivery of recombinant human PK2 on wheel-running.

The results shown in FIG. 9 indicate that PK2 delivery suppressed the high wheel-running behavior associated with dark phase, while administration of saline only slightly inhibited wheel-running behavior. In contrast to the normally quiescent daytime activity, PK2-treated rats were about half as active during day as at night. PK2 infusion caused slight delay of wheel-running rhythm in subsequent days, however, this delay was not significantly different from controls. These results indicate that PK2, which is normally high during subjective day, inhibits wheel-running activities. During subjective night when endogenous PK2 levels are low, the wheel-running activities are disinhibited. The increased wheel-running activity observed on the next subjective day in PK2-treated rats could be the results of PKR2 receptor desensitization caused by PK2 administration. Thus, PK2 is an output molecule that transmits the circadian locomotor rhythm of the SCN clock.

In summary, this example shows that PK2 administration to rats alters their circadian rhythm.

EXAMPLE VII

Measurement of Cytosolic Free Calcium

This example describes an assay for measurement of cytosolic free calcium.

Cells were suspended in HEPES medium and incubated with 2 μM of fura-3 AM for 20 min at 31° C. The cells were then centrifuged, washed, resuspended in fura-3 free medium and seeded into 96 wells at $4 \times 10^4$ cells per well. The cells were loaded with Fluo-3 AM (Molecular Probes) in standard buffer solution (130 mM NaCl, 2 mM $CaCl_2$, 5 mM KCl, 10 mM glucose, 0.45 mM $KH_2PO_4$, 0.4 mM $Na_2HPO_4$, 8 mM $MgSO_4$, 4.2 mM $NaHCO_3$, 20 mM HEPES and 10 μM probenecid) with 0.1% fetal bovine serum for 1 h at 37° C., then washed with a standard buffer solution. Transient changes in $[Ca2+]_i$ evoked by prokineticins were monitored using the FLIPR system (Fluorometric Imaging Plate Reader; Molecular Devices) at 488 nm for 210 s.

EXAMPLE VIII

Temporal Profiles of PK2 mRNA in the SCN in Response to Light/Dark Cycles

This example shows that abrupt shifting of light/dark cycles resulted in altered PK2 molecular rhythm in the SCN.

Light/dark shift experiments were performed using adult C57Bl6 mice (Taconic Farms, N.Y.), which were entrained under 12 hour light: 12 hour dark (12L:12D, lights on 7:00 am, off 7:00 pm) cycle for two weeks with food and water available ad libitum. Light phase was either delayed by 6 hours (lights on 7:00 am, off 1:00 am) or advanced by 6 hours (lights on 7:00 am, off 1:00 pm) and samples were taken every three hours for the 24 hour period (Zeitgeber time, ZT, ZT1-22). To test the adaptations of these shifted mice, animals were placed for an additional two normal light/dark cycles and samples were collected for another 24 hour period.

Figure 14:
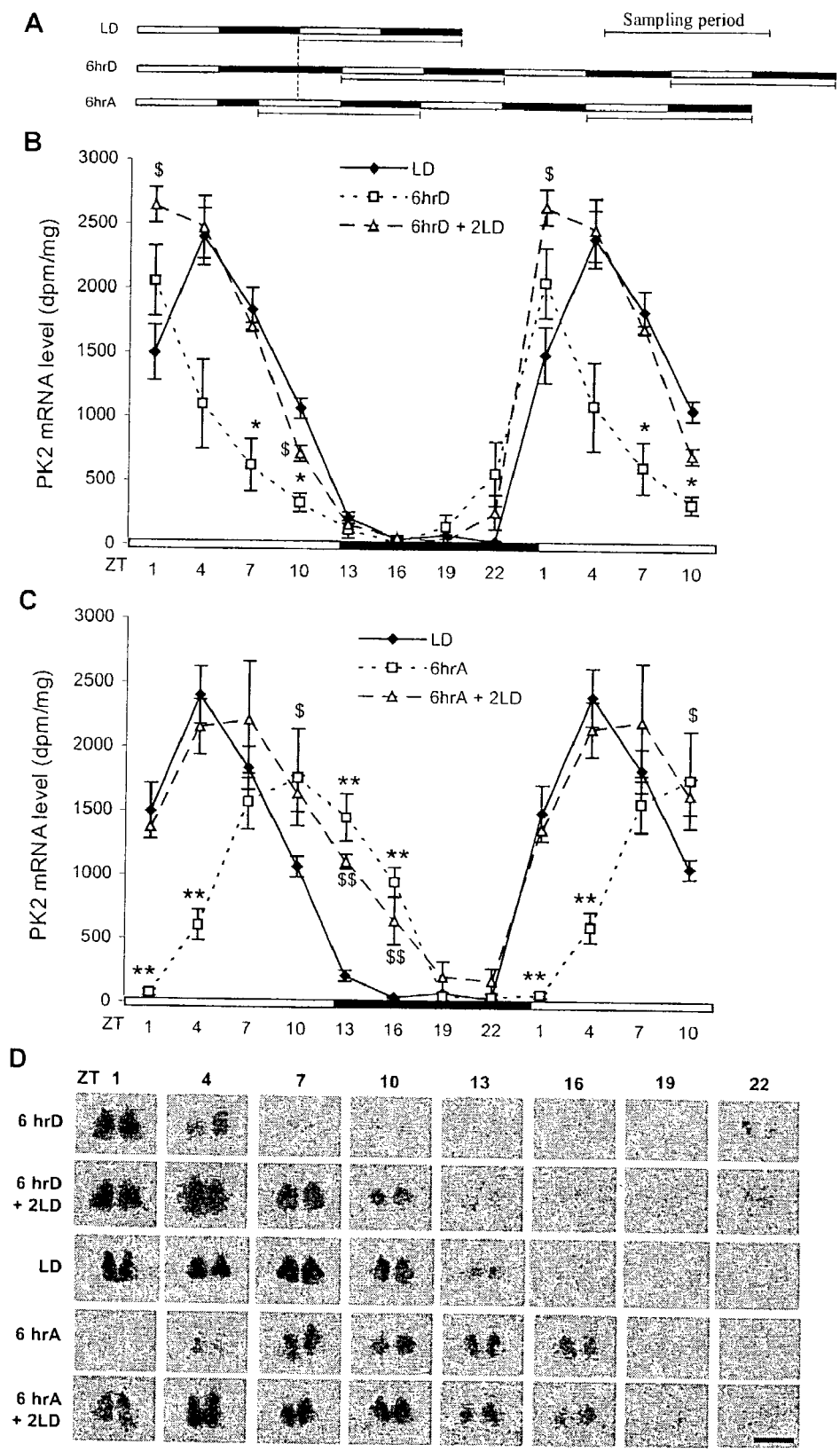
FIG. 14 shows a temporal profile of PK2 mRNA expression in the SCN in response to abrupt shifting of light/dark cycles.

FIG. 14 shows the results of experiments in which PK2 mRNA rhythm in the SCN was measured for a 24 hour cycle. FIG. 14A shows a diagram of the light and dark period to which animals were exposed. As shown, animals were first entrained under normal 12 hour light: 12 hour dark (LD) cycle, followed by either 6-hour delay (6 hrD) or 6-hour advance (6 hrA) of light phase. FIGS. 14B and C show PK2 mRNA levels under conditions of 6 hour delay or 6 hour advance, respectively. Both 6-hour delay and 6-hour advance caused obvious changes in PK2 mRNA oscillation rhythm when compared to normal LD cycle, as indicated in FIGS. 14B and C. However, there were significant differences between these regimens. In 6-hour delay, the pattern of PK2 mRNA expression was similar to that observed under normal LD, with a slightly reduced PK2 peak level, and its rhythm advanced by about 3 hours (FIG. 14B). Similar to normal LD, PK2 mRNA was expressed during light period and remained low during dark phase. However, an early onset of PK2 mRNA at ZT22 was observed. In contrast, advance of 6-hour caused more changes in PK2 mRNA rhythm. The peak of PK2 mRNA was reduced and delayed by about 6 hours (FIG. 14C). Unlike normal LD, the peak of PK2 mRNA delayed to about ZT10 and the level of PK2 remained high during the first half of the dark period. The adaptation of these shifted mice was further tested for two additional LD cycles. As judged by the rhythm of PK2 mRNA expression in the SCN, mice under 6-hour delay regimen adapted quickly after placement in 2 additional LD cycles (FIG. 14B). There was also clear adaptation in 6-hour advanced mice, however, PK2 mRNA rhythm was still significantly different from control groups (FIG. 14C).

Taken together, these results indicate that a 6-hour advance significantly causes more changes in the molecular rhythm of PK2 in the SCN, and that mice adapt more quickly to the 6-hour delay than to the 6-hour advance regimen.

In FIGS. 14B and C, open and filled horizontal bars indicate light and dark periods, respectively. Abbreviations are as follows: normal light/dark cycle (LD); 6-hour delay (6 hrD); 6-hour delay followed by adaptation of 2 additional LD (6 hrD+2 LD); 6-hour advance (6 hrA); and 6-hour advance followed by adaptation of 2 additional LD (6 hrA+2 LD). In FIG. 14D, which shows representative autoradiograms depicting PK2 mRNA expression in the SCN under different light/dark conditions, the scale bar=1 mm, and each value is the mean±SEM of 3 animals. * is p<0.05, and ** is p<0.01 (Student's t-tests), which represent significant differences from control levels under LD for 6 hrD and 6 hrA. $ p<0.05, and $$ p<0.01 represent significant differences from control levels under LD for 6 hrD+2 LD and 6 hrA+2 LD.

In summary, this example shows that in mice exposed to abrupt shifting of light/dark cycles, PK2 mRNA expression was altered.

EXAMPLE IX

Molecular Rhythm of PK2 in mCry1,2−/− Mice

This example shows that under normal light/dark conditions, some molecular rhythms, including a PK2 rhythm, are preserved in clockwork mutant mice.

Light regulated mPer2 molecular rhythm in the SCN of cryptochrome-deficient (mCry1,2−/−) mice that lack functional circadian clock has been observed to be preserved. To determine if light-regulated PK2 molecular rhythm in the SCN is preserved in mCry1,2−/− mice, levels of PK2 mRNA were observed in mCry1,2−/− mice under both light/dark (LD) and constant dark (DD) conditions.

In these experiments, wild type and mCry1,2−/− mice were entrained to normal 12L:12D and sampled every three hours for the 24 hour period (Zeitgeber time, ZT, ZT1-22). A second group of mCry1,2−/− mice were placed into two days of constant darkness (2DD) (Circadian time, CT, CT1-22). For light pulse experiments, mCry1,2−/− mice received a 15 min light pulse (400 lux) at ZT14, and sampled one or two hours after light pulse. Dark control mCry1,2−/− mice did not receive a light pulse.

To determine PK2 molecular rhythm in the SCN of mCry1, 2−/− mice, levels of PK2 mRNA were determined. PK2 mRNA expression in mCry1,2−/− mice is shown in FIG. 15A, while PK2 mRNA expression in wild type mice under 12L:12D (LD) is shown in FIG. 15B. FIG. 15C shows representative autoradiograms of PK2 mRNA in mCry1,2−/− mice and wild type mice under normal LD are shown (top and bottom row, respectively). Representative dark field images of PK2 mRNA in mCry1,2−/− mice under LD are shown are shown in the middle row. The bright field image shows a cresyl-violet stained section, which depicts the cellular structure of SCN. In FIG. 15C, the scale bar=1 mm. Each value represents the mean±SEM of 3-6 animals. For FIG. a6D, PK2 mRNA levels in wild type and mCry1,2−/− mice are shown under light pulse and dark control conditions. In this figure, * $p <0.05$, Student's t-tests. The results shown in FIG. 15D indicate that PK2 mRNA level increased one and two hours in mCry1,2−/− mice after delivery of a brief light pulse at ZT14.

PK2 molecular rhythm in the SCN of mCry1,2−/− mice was apparent under normal LD, with the presence of a low level of PK2 mRNA in the light phase and absence of PK2 mRNA in the dark phase, as indicated in FIGS. 2A and C. Similar to wild type mice, the peak level of this residual PK2 rhythm was around ZT4, although its magnitude was smaller (only about 5% of that observed in wild type mice). This residual PK2 molecular rhythm was absent when mCry1, 2−/− mice were placed under constant darkness (FIG. 15A). These results indicate that the residual PK2 rhythm observed in mCry1,2−/− mice under normal LD is directly driven by light.

Figure 2:
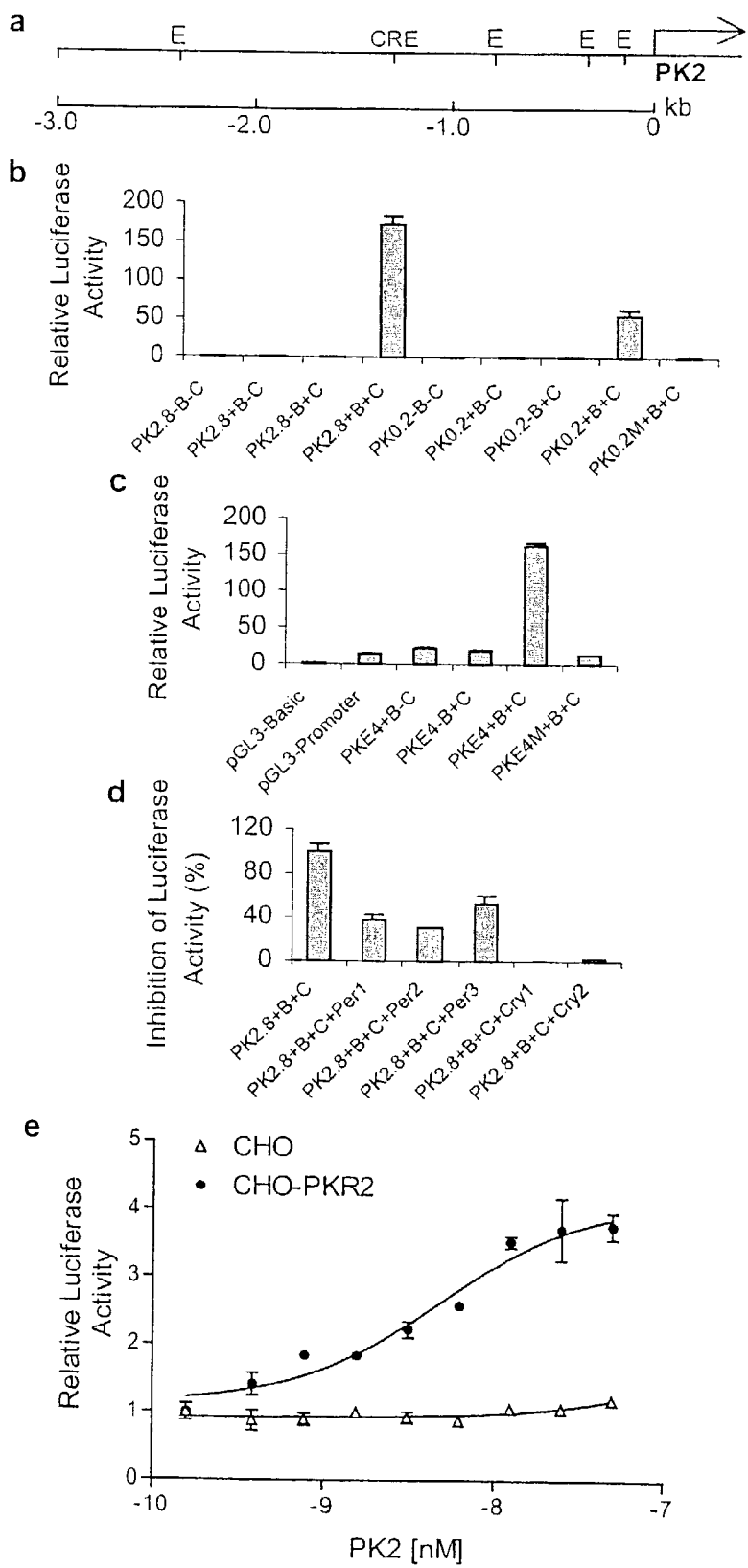
FIG. 2 shows in vitro transcription analyses of mouse PK2 gene.
Figure 15:
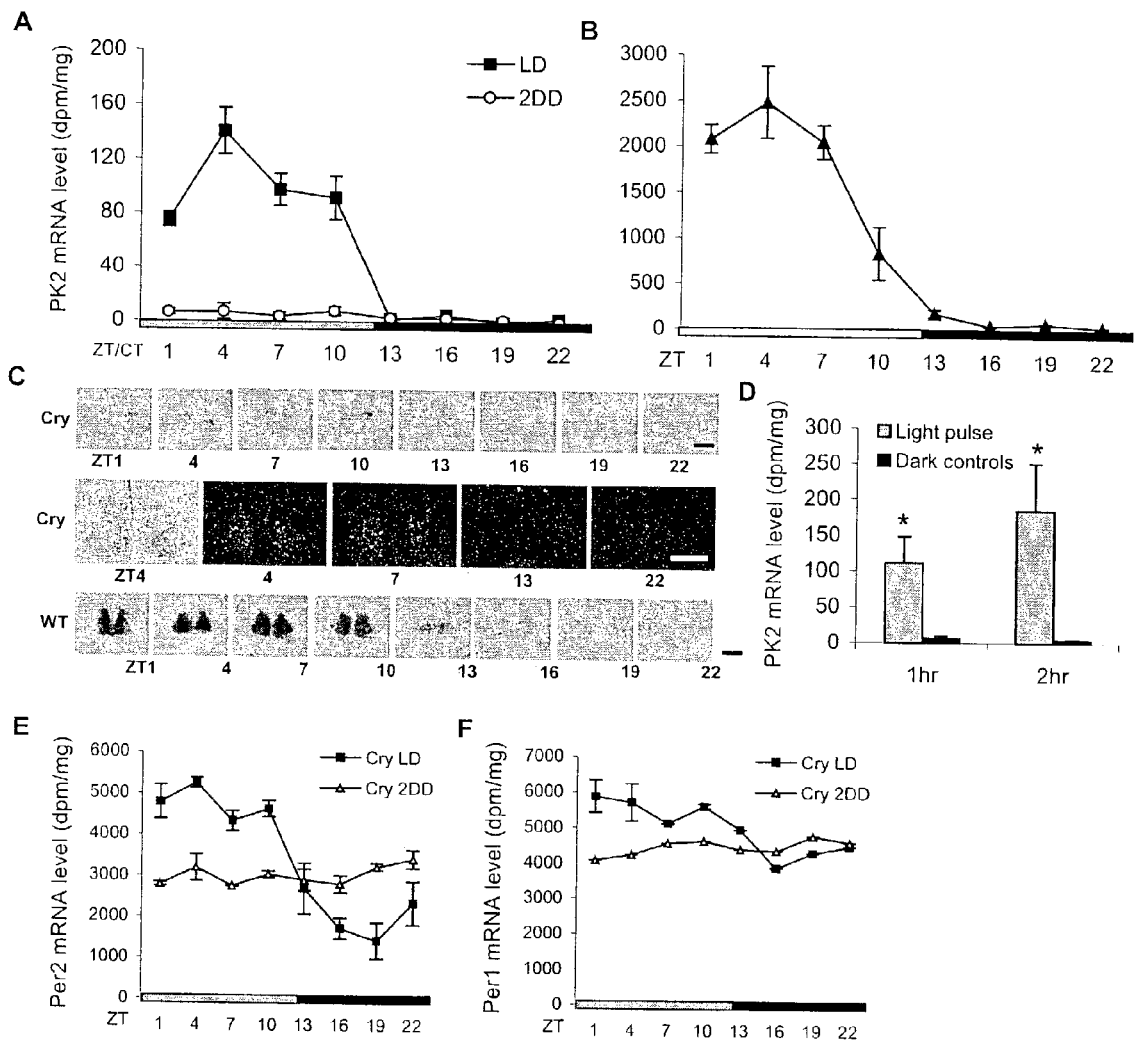
FIG. 15 shows molecular rhythms in the SCN of mCry1, 2-/- mice under normal light/dark or constant dark conditions.

The temporal profile of mPer1 and mPer2 rhythm in mCry1,2−/− mice under normal LD also was determined (FIGS. 15, E and F). The molecular rhythm of mPer2 was observed to remain intact, with about 4-fold higher levels during the light phase than the dark phase (FIG. 15E), as has been observed in wild type animals. This molecular rhythm of mPer2 was not observed under constant darkness (FIG. 15E). A diurnal rhythm also was observed for mPer1 in mCry1,2−/− mice under normal LD, but not DD (FIG. 15F). Thus, mPer1 and mPer2 were non-oscillating and slightly elevated during the dark phase of mCry1,2−/− mice under constant darkness (FIGS. 2, E and F). These results indicate that under normal light/dark conditions, some molecular rhythms, including a residual PK2 rhythm, are preserved in clockwork mutant mice. This residual PK2 rhythm could contribute to the maintenance of behavioral rhythms observed in mCry1,2−/− mice under normal LD.

To obtain the results shown in FIG. 15, antisense and sense riboprobes containing the coding region of mouse PK2 (accession number AF487280 1-528 nt), Per1 (accession number AF022992 340-761nt) or Per2 (accession number AF035830 9-489 nt) were generated. In situ hybridizations were processed as described (Winzer-Serhan et all, 1999, Cheng et al., 2002). Briefly, brains were quickly removed, frozen in isopentane and stored at −70° C. until use. For all experiments, 20 mm sections were collected and mounted onto superfrost-plus slides. Tissue sections were fixed in 4% paraformaldehyde for 1 hour followed by three 0.1M PB washes. Sections were pretreated with proteinase K (1 mg/ml), acetylated, dehydrated and air-dried. Sections were hybridized with riboprobes (antisense or sense for PK2, Per1 or Per2, $1\times10^7$ cpm/ml) and incubated at 60° C. for 18 hours, followed by RNAase (20 mg/ml) digestion, decreasing salinity washes and a 30 minute high stringency (68° C.) wash. After dehydration and air-drying, tissue sections were exposed to Kodak Biomax film and autoradiograms were developed after 3-4 days. Some of the issue sections were dipped in liquid NTB-2 emulsion and developed after five weeks of exposure period. Emulsion-dipped sections were counterstained with cresyl violet, and cover-slipped for analysis by transillumination microscopy. Specific hybridization signals of PK2, Per1 and Per2 were quantitatively analyzed using a video-based computer image analysis system (MCID, Imaging Research, St. Catharine's, Ontario, Canada). A calibration curve of optical density versus radioactivity (dpm/mg tissue wet weight) was constructed using $^{14}C$-standards. Specific hybridization signals in the SCN were determined by subtracting background values from adjacent brain regions that have no hybridization signals. Data were normalized with respect to the differences between signal intensities in same areas of SCN. Images of SCN were taken from autoradiograms and prepared in Adobe Photoshop. Emulsion-dipped images were taken under transillumination microscope (BX50, Olympus) using Spot camera software version 2.2.2 (Diagnostic Instruments, Sterling Heights, Mich.). Captured images were transferred to Adobe Photoshop 6.0 for figure preparation.

EXAMPLE X

Light Inducibility of PK2 in Melanopsin-Deficient Mice

This example shows that melanopsin is an input mechanism for the light inducibility of PK2.

Melanopsin is the primary photoreceptor for circadian photic entrainment. To determine if the light inducibility of PK2 is blunted in melanopsin-deficient mice (Opn4−/−), PK2 mRNA expression in the SCN of Opn4−/− mice was observed.

Wild type and melanopsin-deficient (Opn4−/−) mice (on C57B16/129 hybrid background) were entrained to normal 12L;12D and sampled every three hours for the 24 hour period (Zeitgeber time, ZT, ZT1-22). For light pulse studies, wild type and Opn4−/− mice received a 15 min light pulse (400 lux) at ZT14 and were sampled one or two hours after light pulse. PK2 mRNA expression was measured one or two hours after the delivery of the 15-min light pulse at ZT14.

Figure 16:
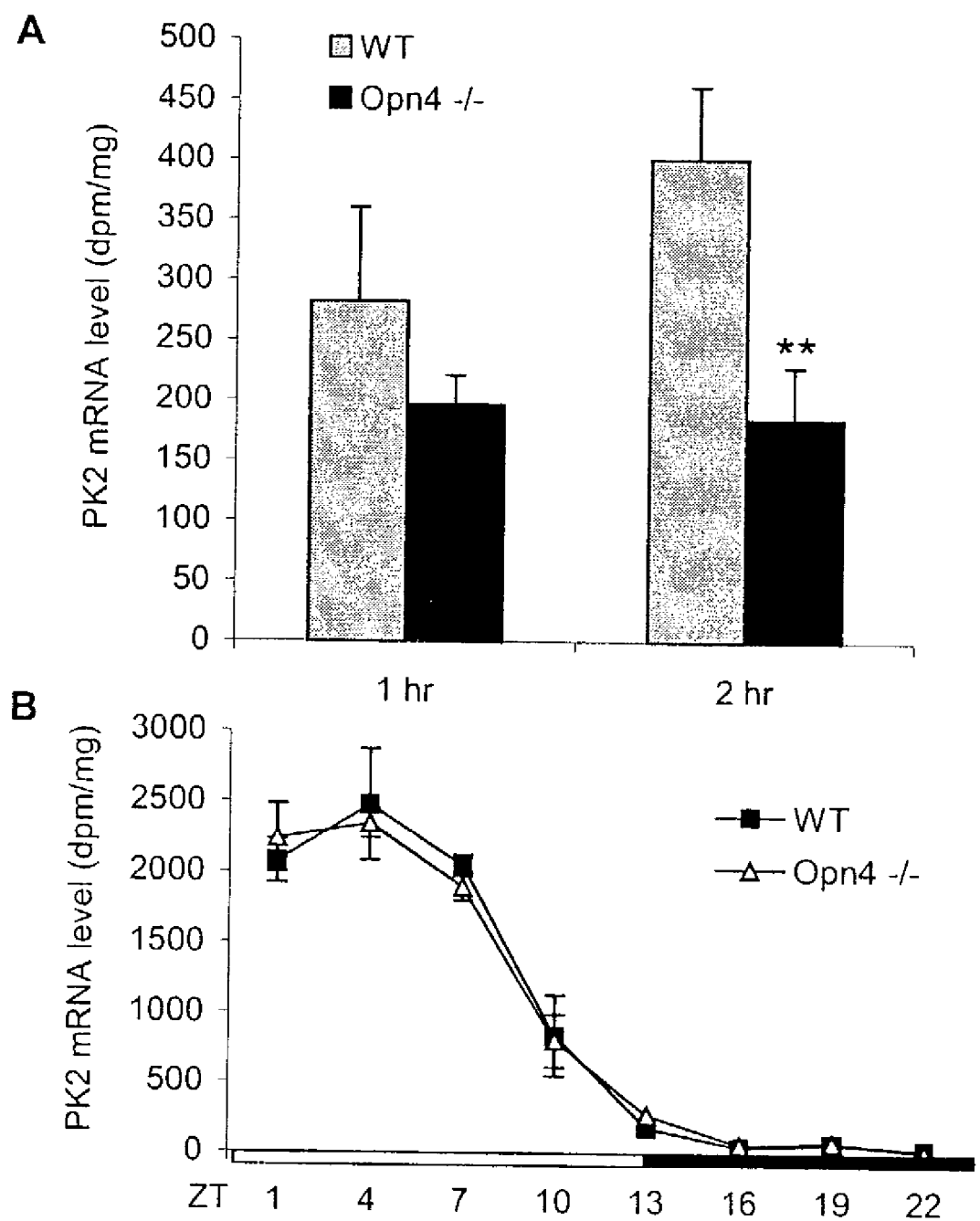
FIG. 16 shows that the light inducibility of PK2 mRNA in the SCN of Opn4-/- mice is reduced in comparison to wild type mice.

The results of these experiments are shown in FIG. 16A. Shaded and filled bars represent light pulse-induced PK2 mRNA in wildtype (WT) and Opn4−/− mice, respectively. As shown, light pulse-induced PK2 mRNA in Opn4−/− mice was reduced by about 30% and 50%, one and two hours after light pulse, respectively.

As shown in FIG. 16B, the temporal profile of PK2 mRNA in wildtype (filled squares) arid Opn4−/− mice (open triangles) under normal LD cycle also was examined. The oscillation profile of PK2 in the Opn4−/− mice was similar to that observed in the wild type mice, consistent with the normal locomotor behavior in Opn4−/− mice under light/dark cycle. In FIG. 16B, each value represents the mean±SEM of 4 animals. ** $p <0.01$, Student's t-tests.

These results indicate that melanopsin is an input mechanism for the light inducibility of PK2, but that one or more other light sensing mechanism of light entrainment are also involved.

EXAMPLE XI

The Role of PK2 Expression in Encoding Photoperiodic Information

This example shows the effect of photoperiod on PK2 mRNA rhythm in the SCN.

Figure 17:
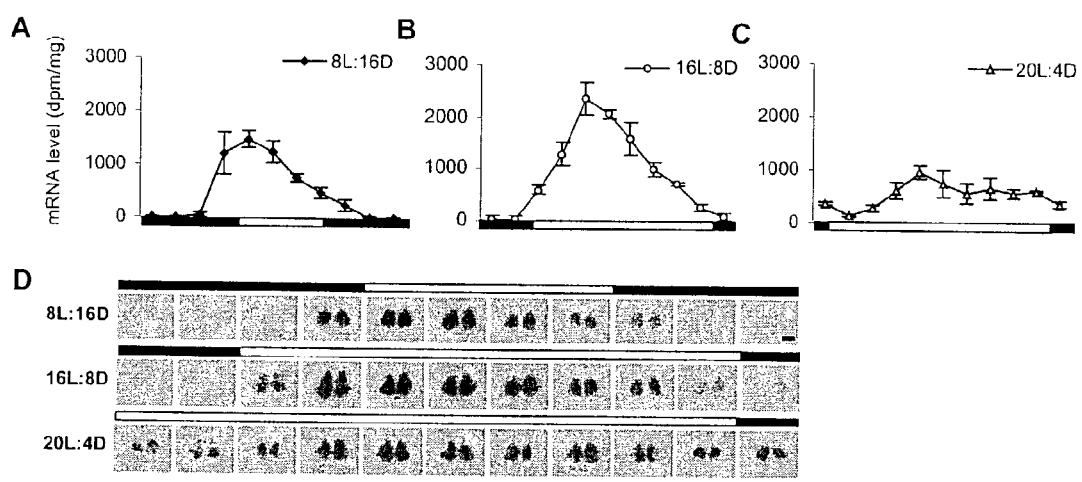
FIG. 17 shows the effect of photoperiod on PK2 mRNA rhythm in the SCN.

To determine if the molecular rhythm of PK2 in the SCN encodes photoperiodic information, animals were entrained under normal 12 hour light: 12 hour dark (LD) cycle, followed by placement in different photoperiod for four weeks: 8 hour light:16 hour dark (8L:16D), 16 hour light: 8 hour dark (16L:8D) or 20 hour light: 4 hour dark (20L:4D). For the 20 hour light: 4 hour dark (20L:4D), animals were first placed in 14L:10D for one week, transferred to 16L:8D for another week, followed by two weeks in 20L:4D. Samples used for determining PK2 mRNA levels in the SCN were taken every two hours throughout the 24 hour cycle. The results of this study are shown in FIG. 17. Open and filled bars indicate light and dark periods, respectively.

FIG. 17A shows PK2 mRNA levels under 8L:16D conditions. FIG. 17B shows PK2 mRNA levels under 16L:8D conditions. FIG. 17C shows PK2 levels under 20L:4D conditions. FIG. 17D shows representative autoradiograms of PK2 mRNA in the SCN under the different photoperiods described above. Scale bar=1 mm. Each value represents the mean±SEM of 3-4 animals.

As indicated in FIGS. 17C and D, when animals were entrained to an even longer light period (20L:4D), PK2 mRNA also followed the light period and was detected during the entire 20 hour light period. During the short photoperiod (8L:16D), however, PK2 mRNA rises before lights on and persists after lights off, as shown in FIG. 17A. The temporal profile of PK2 mRNA in the short photoperiod is similar to that observed in the normal LD or constant darkness (2DD). Thus, for shortened light periods, the circadian loops have dominant control over PK2 rhythms. Taken together, these results indicate that photoperiodic information likely is encoded by the duration of PK2 expression.

Interestingly, the peak of PK2 mRNA expression is higher in long day (16L:8D) than in short day (8L;16D) or normal LD. However, a further increase in light period (20L;4D) depressed the peak PK2 level (FIG. 17C).

As shown in FIG. 17B, with increased photoperiod length (16L:8D), PK2 mRNA expression expanded to the entire 16 hour light phase, in comparison to the results shown in FIG. 16B, which indicated that during normal LD cycle, PK2 mRNA was highly expressed during the 12-hour light phase with peak level at ZT4.

In summary, this example shows that PK2 mRNA expression is regulated by photoperiod.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention.

What is claimed is:

1. A method for identifying an agent that modulates output of a circadian pacemaker of a suprachiasmatic nucleus (SCN), comprising:

(a) contacting a sample comprising a prokineticin 2 (PK2) receptor as set forth in SEQ ID NO:2 with at least one test agent, under conditions suitable for the PK2 receptor to bind to the test agent; and (b) detecting circadian locomotor activity induced by the test agent as compared to the circadian locomotor activity induced by a known PK2 receptor modulating agent, wherein the known PK2 receptor modulating agent is human PK2, thereby identifying the test agent as an agent for modulating output of the circadian pacemaker of the suprachiasmatic nucleus (SCN).

2. The method of claim 1, wherein the test agent is administered to an animal having an observable circadian locomotor activity associated with the output of the SCN.

3. The method of claim 2, wherein the animal is a mammal.

4. The method of claim 3, wherein the animal is selected from human, non-human primate, rat and mouse.

5. The method of claim 2, wherein the activity is wheel-running activity.

6. The method of claim 1, further comprising contacting the PK2 receptor under conditions wherein the test agent promotes a signal as compared to the known PK2 modulating agent.

7. The method of claim 6, wherein the signal is calcium ion mobilization.

8. The method of claim 6, wherein the receptor is contacted with greater than about 100 candidate test agents.

9. The method of claim 6, wherein the receptor is contacted with greater than about $10^5$ test agents.

10. The method of claim 6, wherein the receptor is contained in a human cell preparation.

11. The method of claim 1, further comprising contacting the PK2 receptor under conditions wherein the binding of the test agent to the PK2 receptor is compared to the binding of the known PK2 receptor modulating agent, wherein similar binding to the PK2 receptor of the test agent and the known agent identifies the test agent as an agent that binds to and activates the PK2 receptor.

12. The method of claim 10 or 11, wherein the PK2 receptor is contacted with greater than about 100 candidate test agents.

13. The method of claim 10 or 11, wherein the receptor is contacted with greater than about $10^5$ test agents.

14. The method of claim 11, wherein the receptor is contained in a human cell preparation.

* * * * *

UNITED STATES PATENT AND TRADEMARK OFFICE
CERTIFICATE OF CORRECTION

PATENT NO.       : 7,598,048 B2                                       Page 1 of 1
APPLICATION NO. : 10/417426
DATED            : October 6, 2009
INVENTOR(S)      : Zhou et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 511 days.

Signed and Sealed this

Twenty-eighth Day of September, 2010

David J. Kappos
*Director of the United States Patent and Trademark Office*